(12) United States Patent
Lin et al.

(10) Patent No.: US 10,266,495 B2
(45) Date of Patent: *Apr. 23, 2019

(54) PHENYL QUINOLINONE DERIVATIVES AS MUTANT-ISOCITRATE DEHYDROGENASE INHIBITORS

(71) Applicant: FORMA TM2, Inc., Watertown, MA (US)

(72) Inventors: Jian Lin, Acton, MA (US); Anna Ericsson, Shrewsbury, MA (US); Ann-Marie Campbell, Monroe, CT (US); Gary Gustafson, Ridgefield, CT (US); Zhongguo Wang, Lexington, MA (US); R. Bruce Diebold, Waltham, MA (US); Susan Ashwell, Carlisle, MA (US); David R. Lancia, Jr., Boston, MA (US); Justin Andrew Caravella, Cambridge, MA (US); Wei Lu, Newton, MA (US)

(73) Assignee: FORMA TM2, INC., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/977,512

(22) Filed: May 11, 2018

(65) Prior Publication Data
US 2018/0327361 A1 Nov. 15, 2018

Related U.S. Application Data

(63) Continuation of application No. 14/858,174, filed on Sep. 18, 2015, now Pat. No. 10,005,734.

(60) Provisional application No. 62/206,631, filed on Aug. 18, 2015, provisional application No. 62/128,089, filed on Mar. 4, 2015, provisional application No. 62/053,006, filed on Sep. 19, 2014.

(51) Int. Cl.
| | |
|---|---|
| *C07D 215/227* | (2006.01) |
| *A61K 31/4709* | (2006.01) |
| *C07D 401/12* | (2006.01) |
| *C07D 405/12* | (2006.01) |
| *C07D 409/12* | (2006.01) |
| *C07D 471/04* | (2006.01) |

(52) U.S. Cl.
CPC ...... *C07D 215/227* (2013.01); *A61K 31/4709* (2013.01); *C07D 401/12* (2013.01); *C07D 405/12* (2013.01); *C07D 409/12* (2013.01); *C07D 471/04* (2013.01)

(58) Field of Classification Search
CPC .......... C07D 215/227; C07D 401/12; C07D 405/12; C07D 409/12; C07D 471/04; A61K 31/4705
See application file for complete search history.

(56) References Cited

U.S. PATENT DOCUMENTS

| | | | |
|---|---|---|---|
| 5,262,564 A | 11/1993 | Kun et al. | |
| 9,073,941 B2 | 7/2015 | Wong et al. | |
| 9,624,175 B2 | 4/2017 | Lin et al. | |
| 9,624,216 B2 | 4/2017 | Lin et al. | |
| 9,771,349 B2* | 9/2017 | Lin | C07D 401/12 |
| 9,815,817 B2 | 11/2017 | Lin et al. | |
| 9,834,539 B2 | 12/2017 | Lin et al. | |
| 10,005,734 B2* | 6/2018 | Lin | C07D 215/227 |
| 2014/0235620 A1 | 8/2014 | Caferro et al. | |
| 2016/0083349 A1 | 3/2016 | Lin et al. | |
| 2016/0083365 A1 | 3/2016 | Lin et al. | |
| 2016/0083366 A1 | 3/2016 | Lin et al. | |
| 2016/0083367 A1 | 3/2016 | Lin et al. | |
| 2016/0311774 A1 | 10/2016 | Lin et al. | |
| 2016/0311818 A1 | 10/2016 | Lin et al. | |
| 2017/0174658 A1 | 6/2017 | Lin et al. | |
| 2018/0086733 A1 | 3/2018 | Lin et al. | |
| 2018/0118732 A1 | 5/2018 | Lin et al. | |

(Continued)

FOREIGN PATENT DOCUMENTS

| | | |
|---|---|---|
| RU | 2284325 C2 | 9/2006 |
| WO | WO-2006/054912 A1 | 5/2006 |

(Continued)

OTHER PUBLICATIONS

U.S. Appl. No. 15/964,812, filed Apr. 2018, Lin.*

(Continued)

*Primary Examiner* — D Margaret M Seaman

(74) *Attorney, Agent, or Firm* — Choate, Hall & Stewart LLP; John P. Rearick; Christopher K. Haley

(57) ABSTRACT

The invention relates to inhibitors of mutant isocitrate dehydrogenase (mt-IDH) proteins with neomorphic activity useful in the treatment of cell-proliferation disorders and cancers, having the Formula:

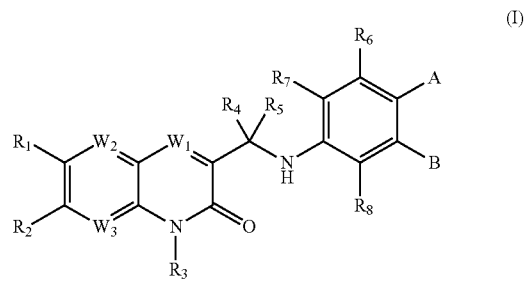

where A, B, $W_1$, $W_2$, $W_3$, and $R_1$-$R_8$ are described herein.

9 Claims, 3 Drawing Sheets

(56) References Cited

U.S. PATENT DOCUMENTS

| | | |
|---|---|---|
| 2018/0134682 A1 | 5/2018 | Lin et al. |
| 2018/0141910 A1 | 5/2018 | Lin et al. |
| 2018/0312487 A1 | 11/2018 | Lin et al. |
| 2018/0327382 A1 | 11/2018 | Lin et al. |

FOREIGN PATENT DOCUMENTS

| | | |
|---|---|---|
| WO | WO-2007/117778 A2 | 10/2007 |
| WO | WO-2008/069242 A1 | 6/2008 |
| WO | WO-2011/072174 A1 | 6/2011 |
| WO | WO-2012/129562 A2 | 9/2012 |
| WO | WO-2012/171506 A1 | 12/2012 |
| WO | WO-2013/102431 A1 | 7/2013 |
| WO | WO-2014/141153 A1 | 9/2014 |
| WO | WO-2015/003146 A1 | 1/2015 |
| WO | WO-2016/044781 A1 | 3/2016 |
| WO | WO-2016/044782 A1 | 3/2016 |
| WO | WO-2016/044787 A1 | 3/2016 |
| WO | WO-2016/044789 A1 | 3/2016 |
| WO | WO-2016/106331 A1 | 6/2016 |
| WO | WO-2016/108045 A2 | 7/2016 |
| WO | WO-2016/171755 A1 | 10/2016 |
| WO | WO-2016/171756 A1 | 10/2016 |
| WO | WO-2017/019429 A1 | 2/2017 |
| WO | WO-2017/146795 A1 | 8/2017 |
| WO | WO-2017/213910 A1 | 12/2017 |
| WO | WO-2017/223202 A1 | 12/2017 |
| WO | WO-2018/111707 A1 | 6/2018 |

OTHER PUBLICATIONS

U.S. Appl. No. 15/964,844, filed Apr. 2018, Lin.*
U.S. Appl. No. 15/964,844, filed Apr. 27, 2018, Lin et al.
U.S. Appl. No. 15/964,812, filed Apr. 27, 2018, Lin et al.
Badr, M.Z.A. et al., Reaction of Quinoxaline Derivatives with Nucleophilic Reagents, , Bull Chem Soc Jpn, 56(1): 326-330 (1983).
Balss, J. et al., Analysis of the IDH1 codon 132 mutation in brain tumors, Acta Neuropathol., 116: 597-602 (2008).
Cui, Z. et al., Structure and properties of N-heterocycle-containing benzotriazoles as UV absorbers, Journal of Molecular Structure, 1054: 94-99 (2013).
Dang, L. et al., Cancer-associated IDH1 mutations produce 2-hydroxyglutarate, Nature, 462: 739-744 (2009).
Dang, L. et al., IDH mutations in glioma and acute myeloid leukemia, Trends Mol. Med., 16(9): 387-397 (2010).
Database Caplus (Online) Chemical Abstracts Service, Columbus, Ohio, US; retrieved from STN Database accession No. 1987: 407040 abstract, Prostakov, N.S. et al., Synthesis of substituted 2-pyridones and 4-aza-3-fluorenones, Khimiya Geterotsiklicheskikh Soedinenii, 7: 939-942 (1986).
Database Registry (Online) Chemical Abstracts Service, Columbus, Ohio, US; Database accession No. 1434379-53-9 (Jun. 5, 2013).
Database Registry (Online) Chemical Abstracts Service, Columbus, Ohio, US; Database accession No. 1497653-96-9 (Dec. 18, 2013).
Database Registry (Online) Chemical Abstracts Service, Columbus, Ohio, US; Database accession No. 1567357-55-4 (Mar. 12, 2014).
Database Registry (Online) Chemical Abstracts Service, Columbus, Ohio, US; Database accession No. 1567456-94-3 (Mar. 12, 2014).
Dinardo, C.D. et al., Serum 2-hydroxyglutarate levels predict isocitrate dehydrogenase mutations and clinical outcome in acute myeloid leukemia, Blood, 121(24): 4917-1924 (2013).
Fatima, S., Molecular docking and 3D-QSAR studies on inhibitors of DNA damage signaling enzyme human PARP-1, J Receptors and Signal Transduction, 32(4) 214-224 (2012).
Gaal, J. et al., Isocitrate Dehydrogenase Mutations Are Rare in Pheochromocytomas and Paragangliomas, J. Clin. Endocrinol. Metab., 95(3): 1274-1278 (2010).
Gross, S. et al., Cancer-associated metabolite 2-hydroxyglutarate accumulates in acute myelogenous leukemia with isocitrate dehydrogenase 1 and 2 mutations, J. Exp. Med., 207(2): 339-344 (2010).
Hayden, J.T. et al., Frequent IDH1 mutations in supratentorial primitive neuroectodermal tumors (sPNET) of adults but not children, Cell Cycle, 8(11): 1806-1807 (2009).
International Search Report for PCT/US2015/051044, 4 pages (dated Nov. 23, 2015).
International Search Report for PCT/US2015/051046, 3 pages (dated Oct. 30, 2015).
International Search Report for PCT/US2015/051053, 4 pages (dated Oct. 28, 2015).
International Search Report for PCT/US2015/051055, 3 pages (dated Nov. 13, 2015).
International Search Report for PCT/US2015/051056, 4 pages (dated Nov. 20, 2015).
International Search Report for PCT/US2015/051059, 3 pages (dated Oct. 30, 2015).
Kombarov, R.V. et al., CA Accession No. 138:368869, abstract only of Chem of Het Compounds, 38(9): 1154-1155 (2002).
Losman, J-A. et al., (R)-2-Hydroxyglutarate is Sufficient to Promote Leukemogenesis and its Effects are Reversible, Science, 339(6127): 1-9 (2013).
Mohamed, E.A. et al., CA Accession No. 122:160601, abstract only of Indian J Chem, Sect B: Org Chem Inc Med Chem, 34B(1): 21-26 (1995).
Morshed, M.N. et al., Computational approach to the identification of novel Aurora-A inhibitors, Bioorg & Med Chem, 19: 907-916 (2011).
Schrader, F.C. et al., Novel Type II Fatty Acid Biosynthesis (FAS II) Inhibitors as Multistage Antimalarial Agents, Chem Med Chem, 8: 442-461 (2013).
Sellner, L. et al. Increased levels of 2-hydroxyglutarate in AML patients with IDH1-R132H and IDH2-R140Q mutations, Eur. J. Haematol., 85: 457-459 (2010).
Shibata, T. et al., Mutant IDH1 Confers an in Vivo Growth in a Melanoma Cell Line with BRAF Mutation, Am. J. Pathol., 178(3): 1395-1402 (2011).
Tintori, C. et al., Identification of Hck Inhibitors As Hits for the Development of Antileukemia and Anti-HIV Agents, Chem Med Chem, 8: 1353-1360 (2013).
Wang, F. et. al., Targeted Inhibition of Mutant IDH2 in Leukemia Cells Induces Cellular Differentiation, Science, 340: 622-626 (2013).
Wang, P. et al., Mutations in Isocitrate Dehydrogenase 1 and 2 Occur Frequently in Intrahepatic Cholangiocarcinomas and Share Hypermetylation Targets with Glioblastomas, Oncogene, 32(25): 3091-3100 (2013).
Ward, P.S. et al., The common feature of leukemia-associated IDH1 and IDH2 mutations is a neomorphic enzymatic activity that converts α-ketoglutarate to 2-hydroxyglutarate, Cancer Cell, 17(3): 225-234 (2010).
Zhao, S. et. al., Glioma-Derived Mutations in IDH1 Dominantly Inhibit IDH1 Catalytic Activity and Induce HIF-1α, Science, 324(5924): 261-265 (2009).
Zheng, B. et al., Crystallographic Investigation and Selective Inhibition of Mutant Isocitrate Dehydrogenase, ACS Medicinal Chemistry Letters, 4(6): 542-546 (2013).
Forma Therapeutics, Discovery and Optimization of a Novel Series ofInhibitors of mt-IDH1, 7th Annual Advances in Chemical Sciences Symposium, Presentation, 21 slides (May 4, 2018).
Prostakov, N.S. et al., Chemistry of Heterocyclic Compounds, CHCCAL, 22(7): 685-810 (1986).

* cited by examiner

Compound I-58

PHENYL QUINOLINONE DERIVATIVES AS MUTANT-ISOCITRATE DEHYDROGENASE INHIBITORS

CROSS-REFERENCE TO RELATED APPLICATIONS

This application is a continuation of U.S. application Ser. No. 14/858,174, filed Sep. 18, 2015, now U.S. patent Ser. No. 10/005,734, which claims the benefit of priority of U.S. Provisional Application No. 62/053,006, filed Sep. 19, 2014 and U.S. Provisional Application No. 62/128,089, filed Mar. 4, 2015, and U.S. Provisional Application No. 62/206,631, filed Aug. 18, 2015, all of which are incorporated herein by reference in their entireties.

FIELD OF INVENTION

The present invention is directed to inhibitors of mutant isocitrate dehydrogenase (mt-IDH) proteins with neomorphic activity useful in the treatment of diseases or disorders associated with such mutant IDH proteins including cell-proliferation disorders and cancers. Specifically, the invention is concerned with compounds and compositions inhibiting mt-IDH, methods of treating diseases or disorders associated with mt-IDH, and methods of synthesis of these compounds.

BACKGROUND OF THE INVENTION

Isocitrate dehydrogenases (IDHs) are enzymes that participate in the citric acid cycle (cellular metabolism). They catalyze the oxidative decarboxylation of isocitrate to 2-oxoglutarate (i.e., α-ketoglutarate, α-KG). There are three isoforms within the IDH family. IDH-1, expressed in the cytoplasm and peroxisome, IDH-2, localized in the mitochondria, both utilize NADP+ as the cofactor and exist as homodimers. IDH-3 is localized in mitochondrial matrix and utilizes NAD+ as a cofactor and exists as tetramer. Mutations in IDH-1 (cytosolic) and IDH-2 (mitochondrial) have been identified in various diseases or disorders including glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, and melanoma (L. Deng et al., Trends Mol. Med., 2010, 16, 387; T. Shibata et al., Am. J. Pathol., 2011, 178(3), 1395; Gaal et al., J. Clin. Endocrinol. Metab. 2010; Hayden et al., Cell Cycle, 2009; Balss et al., Acta Neuropathol., 2008). The mutations have been found at or near key residues in the active site: G97D, R100, R132, H133Q, and A134D for IDH1, and R140 and R172 for IDH2. (See L. Deng et al., Nature, 2009, 462, 739; L. Sellner et al., Eur. J. Haematol., 2011, 85, 457).

Mutant forms of IDH-1 and IDH-2 have been shown to lose wild type activity, and instead exhibit a neomorphic activity (also known as a gain of function activity), of reducing alpha-ketoglutarate to 2-hydroxyglutarate (2-HG). (See P. S. Ward et al., Cancer Cell, 2010, 17, 225; Zhao et. al., Science 324, 261(2009); Dang et. al Nature 462, 739 (2009)). In general, production of 2-HG is enantiospecific, resulting in generation of the D-enantiomer (also known as the R enantiomer or R-2-HG). Normal cells have low basal levels of 2-HG, whereas cells harboring mutations in IDH1 or IDH2 show significantly elevated levels of 2-HG. High levels of 2-HG have also been detected in tumors harboring the mutations. For example, high levels of 2-HG have been detected in the plasma of patients with mutant IDH containing AML. (See S. Gross et al., J. Exp. Med., 2010, 207(2), 339). High levels of 2-HG have been shown to block α-KG dependent DNA and histone demethylases, and ultimately to result in improper dedifferentiation of hematopoietic progenitor cells in AML patients (Wang et. al., Science 340, 622 (2013); Losman et al., Science 339, 1621 (2013)).

Furthermore, patients with Ollier Disease and Mafucci Syndrome (two rare disorders that predispose to cartilaginous tumors) have been shown to be somatically mosaic for IDH1 and 2 mutations and exhibit high levels of D-2-HG. (See Amary et al., Nature Genetics, 2011 and Pansuriya et al., Nature Genetics, 2011).

The inhibition of mt-IDHs and their neomorphic activity with small molecule inhibitors therefore has the potential to be a treatment for cancers and other disorders of cellular proliferation.

SUMMARY OF THE INVENTION

A first aspect of the invention relates to compounds of Formula I:

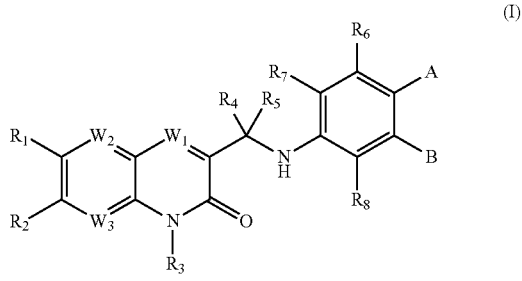

and pharmaceutically acceptable salts, enantiomers, hydrates, solvates, prodrugs, isomers, and tautomers thereof, wherein:

each $W_1$ and $W_2$ is independently CH, CF or N;
$W_3$ is independently $CR_2$, or N;
A is selected from the group consisting of H, D, halogen, CN, —CHO, —COOH, —COOR$_9$, —C(O)NH$_2$, —C(O)NHR$_9$, R$_{10}$S(O)$_2$—, —O(CH$_2$)$_n$C(O)R$_{10}$, —O(CH$_2$)$_n$C(O)NR$_{10}$R$_9$, R$_{10}$S(O)—, heteroaryl, —S(O)Me, —S(O)$_2$Me,

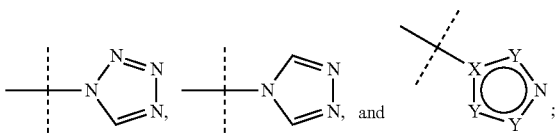

B is selected from the group consisting of:
H, D, OH, NO$_2$, NH$_2$, —NR$_{11}$R$_{12}$, CN, —(CH$_2$)CN, C$_1$-C$_6$ alkyl, C$_1$-C$_6$ haloalkyl, C$_3$-C$_8$ cycloalkyl, aryl, C$_1$-C$_6$ alkoxy, C$_1$-C$_6$ haloalkoxy, heteroaryl, —O(CH$_2$)$_n$R$_{10}$, —(CH$_2$)$_n$C(O)NHR$_9$, —C(O)NH$_2$, —SR$_9$, OR$_9$, —(CHR$_{10}$)$_n$S(O)R$_9$, —(CHR$_{10}$)$_n$S(O)$_2$R$_9$, —S(O)$_2$NR$_9$R$_{10}$, —COOR$_9$,

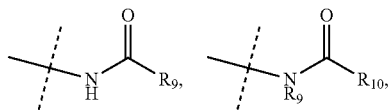

-continued

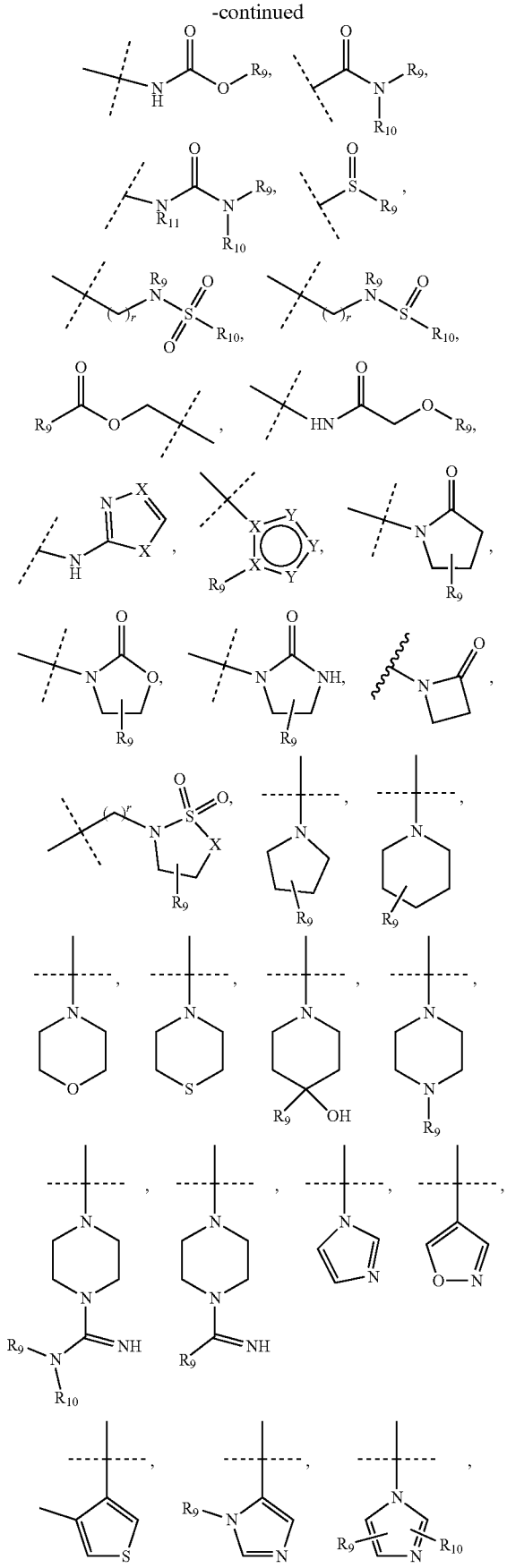

-continued

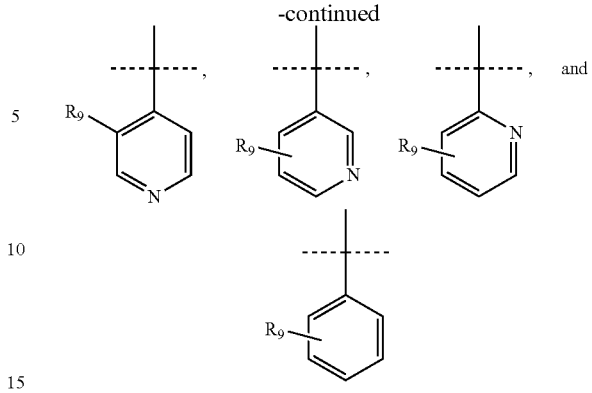

wherein X and Y are independently in each occurrence C, N, $NR_{10}$, S, and O, provided that the ring containing X and Y cannot have more than 4 N or NH atoms or more than one S or O atoms, and wherein the S and O are not contiguous;

$R_1$ is independently H, OH, CN, halogen, $CHF_2$, $CF_3$, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, 3- to 8-membered heterocyclyl, aryl, or heteroaryl, wherein each $C_1$-$C_6$ alkyl, $C_2$-$C_6$ alkenyl, $C_2$-$C_6$ alkynyl, $C_3$-$C_8$ cycloalkyl, 3- to 8-membered heterocyclyl, aryl, or heteroaryl is optionally substituted one or more times with substituents selected from the group consisting of halogen, OH, $NH_2$, CN, $C_1$-$C_6$ alkyl, and $C_1$-$C_6$ alkoxy;

$R_2$ is independently H, OH, CN, halogen, $CF_3$, $CHF_2$, benzyl, $C_1$-$C_6$ alkyl, $C_1$-$C_6$ alkoxy, $NH_2$, —$O(CH_2)_nR_{10}$, —$O(CHR_9)_nR_{10}$, —$O(CH_2)_n$—O—$(CH_2)_mR_{10}$, —$O(CH_2)_nC(O)NHR_{10}$, —$O(CH_2)_nC(O)R_{10}$, $NHR_{11}$, —$N(R_{11})(R_{12})$, $NHC(O)R_{11}$, $NHS(O)R_{11}$, $NHS(O)_2R_{11}$, $NHC(O)OR_{11}$, $NHC(O)NHR_{11}$, —$S(O)_2NHR_{11}$, —$NHC(O)N(R_{12})R_{11}$, $OCH_2R_{11}$, $CHR_9R_{10}$, or $OCHR_{10}R_{11}$, wherein $C_1$-$C_6$ alkyl, $C_1$-$C_6$ alkoxy, or benzyl is optionally substituted with one or more substituents selected from the group consisting of $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkyl substituted with one or more halogen, 3- to 8-membered heterocyclyl, aryl, -heteroaryl-$C(O)NH_2$, and heteroaryl;

$R_3$ is H, $C_1$-$C_6$ alkyl, or —OH, $R_4$ and $R_5$ are independently H, halogen, $CH_2OH$, $C_1$-$C_3$ alkyl, or $C_1$-$C_3$ alkyl substituted with halogen, or $R_4$ and $R_5$ when combined can form a $C_3$-$C_6$ cycloalkyl or $C_3$-$C_8$ heterocyclyl;

$R_6$, $R_7$, and $R_8$ are independently H, halogen, $C_1$-$C_6$ alkyl, $C_1$-$C_6$ alkyl substituted with halogen, $C_1$-$C_6$ alkoxy, $C_1$-$C_6$ alkoxy substituted with one or more halogen, $C_2$-$C_6$ alkenyl, $C_2$-$C_6$ alkynyl, $C_3$-$C_8$ cycloalkyl, 3- to 8-membered heterocyclyl, aryl, heteroaryl, —$(CHR_{11})_nS(O)_2R_{12}$, $OR_{11}$, —$NR_{11}C(O)R_{12}$, $S(O)_2NR_{11}R_{12}$, or —$C(O)NR_{11}R_{12}$;

$R_9$ and $R_{10}$ at each occurrence are independently selected from the group consisting of H, CN, —$CH_2CN$, halogen, —$NR_{11}R_{12}$, —$C(O)NR_{11}R_{12}$, —$NR_{11}C(O)R_{12}$, $CHCF_2$, $CF_3$, $C_1$-$C_6$ alkyl, $R_{11}S(O)_2$—, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, 3- to 8-membered heterocyclyl, aryl, and heteroaryl, wherein each $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, 3- to 8-membered heterocyclyl, aryl, and heteroaryl, is optionally substituted with one or more substituents selected from the group consisting of OH, oxo, halogen, $C_1$-$C_6$ alkyl, $C_1$-$C_6$ alkoxy, $NH_2$, $R_{13}S(O)_2$—, CN, $C_3$-$C_8$ cycloalkyl, 3- to 8-membered heterocyclyl, aryl, heteroaryl, and $R_{13}S(O)_2$—;

$R_{11}$ and $R_{12}$ are independently H, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, 3- to 8-membered heterocyclyl, aryl, and heteroaryl; or when combined $R_{11}$ and $R_{12}$ can form a 3- to 8-membered heterocyclyl or heteroaryl ring;

$R_{13}$ is independently H, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, 3- to 8-membered heterocyclyl, aryl, or heteroaryl;

m is 0, 1, or 2;
n is 0, 1, or 2; and
r is 0, 1, or 2;

provided that:
(1) when $R_1$ is H, then A is CN or tetrazole;
(2) when $R_1$ is H and A is tetrazole, then $R_2$ is not hydrogen, methyl or ethoxy;
(3) when $R_1$ and $R_2$ are H and A is tetrazole, then B and $R_6$ are H;
(4) when $R_1$ is H and $R_2$ is methyl, then neither B nor $R_6$ is methyl
(5) when $R_1$ is H and A is CN, then either B or $R_6$ is not H;
(6) when $R_1$ is $C_1$-$C_6$ alkoxy, then A is CN or imidazole;
(7) when $R_1$ is $C_1$-$C_6$ alkyl, then A is CN, tetrazole, or imidazole;
(8) when $R_1$ is methyl and A is tetrazole, then B and $R_6$ are H;
(9) when $R_1$ is $C_1$-$C_6$ alkyl and A is H, then B is —S(O)$_2$NR$_9$R$_{10}$;
(10) when $R_1$ is tert-butyl, then A is CN; or
(11) when $R_2$ is $C_1$-$C_6$ alkyl, then A is not H, halogen, or benzimidazole.

Another aspect of the invention relates to pharmaceutical compositions of Formula (I')

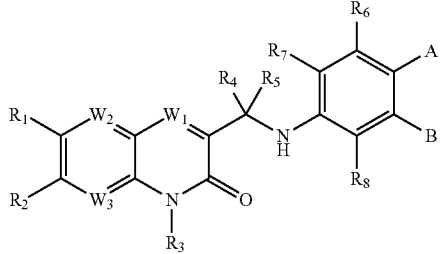

(I')

and pharmaceutically acceptable salts, enantiomers, hydrates, solvates, prodrugs, isomers, and tautomers thereof, wherein:

each $W_1$ and $W_2$ is independently CH, CF or N;
$W_3$ is independently CR$_2$, or N;
A is selected from the group consisting of H, D, halogen, CN, —CHO, —COOH, —COOR$_9$, —C(O)NH$_2$, —C(O)NHR$_9$, R$_{10}$S(O)$_2$—, —O(CH$_2$)$_n$C(O)R$_{10}$, —O(CH$_2$)$_n$C(O)NR$_{10}$R$_9$, R$_{10}$S(O)—, heteroaryl, —S(O)Me, —S(O)$_2$Me,

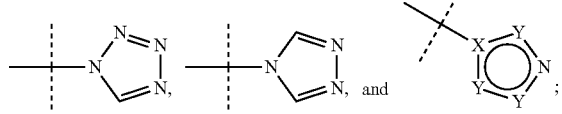

B is selected from the group consisting of:

H, D, OH, NO$_2$, NH$_2$, —NR$_{11}$R$_{12}$, CN, —(CH$_2$)$_n$CN, $C_1$-$C_6$ alkyl, $C_1$-$C_6$ haloalkyl, $C_3$-$C_8$ cycloalkyl, aryl, $C_1$-$C_6$ alkoxy, $C_1$-$C_6$ haloalkoxy, heteroaryl, —O(CH$_2$)$_n$R$_{10}$, —(CH$_2$)$_n$C(O)NHR$_9$, —C(O)NH$_2$, —SR$_9$, OR$_9$, —(CHR$_{10}$)$_n$S(O)R$_9$, —(CHR$_{10}$)$_n$S(O)$_2$R$_9$, —S(O)$_2$NR$_9$R$_{10}$, —COOR$_9$,

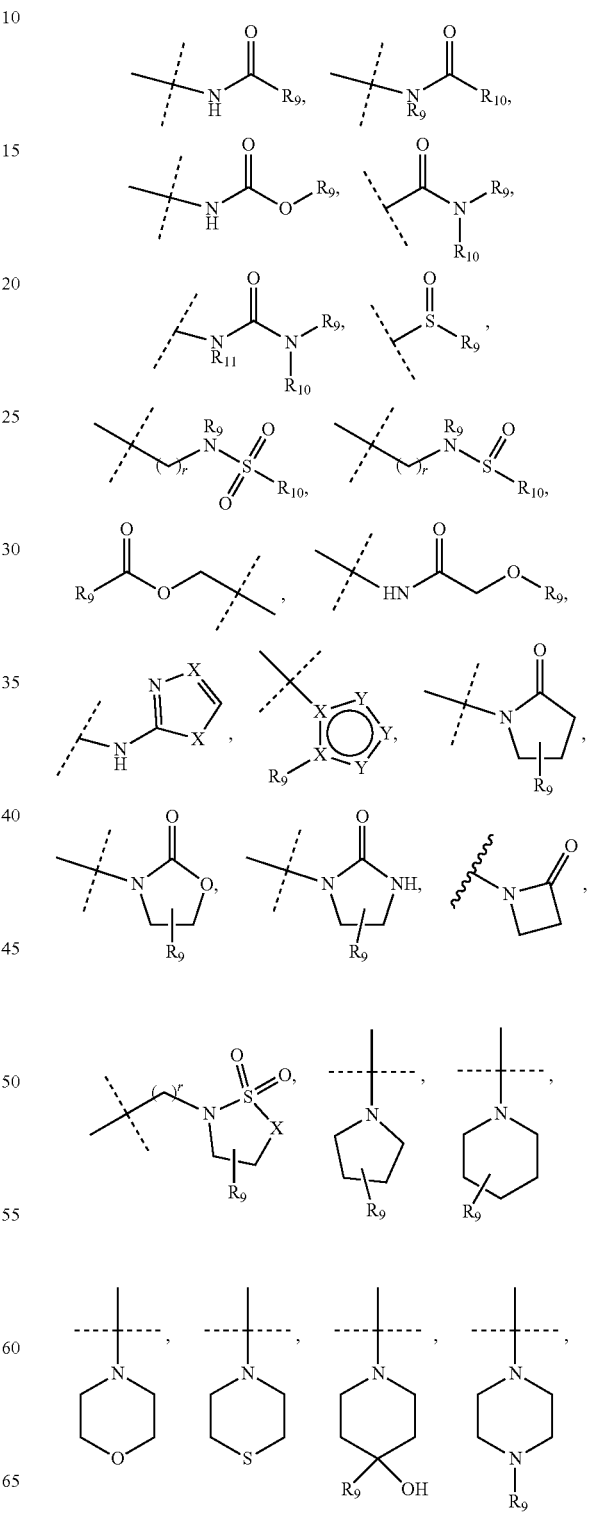

-continued

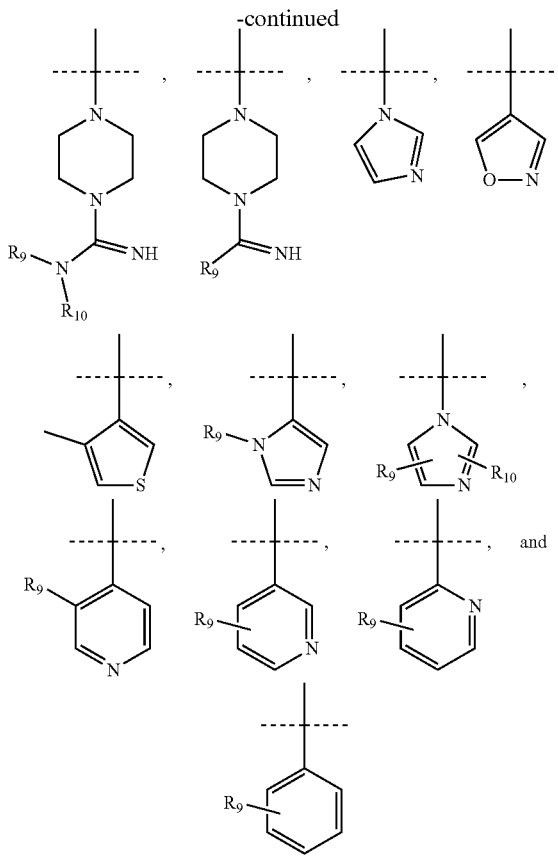

wherein X and Y are independently in each occurrence C, N, NR$_{10}$, S, and O, provided that the ring containing X and Y cannot have more than 4 N or NH atoms or more than one S or O atoms, and wherein the S and O are not contiguous;

R$_1$ is independently H, OH, CN, halogen, CHF$_2$, CF$_3$, C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, 3- to 8-membered heterocyclyl, aryl, or heteroaryl, wherein each C$_1$-C$_6$ alkyl, C$_2$-C$_6$ alkenyl, C$_2$-C$_6$ alkynyl, C$_3$-C$_8$ cycloalkyl, 3- to 8-membered heterocyclyl, aryl, or heteroaryl is optionally substituted one or more times with substituents selected from the group consisting of halogen, OH, NH$_2$, CN, C$_1$-C$_6$ alkyl, and C$_1$-C$_6$ alkoxy;

R$_2$ is independently H, OH, CN, halogen, CF$_3$, CHF$_2$, benzyl, C$_1$-C$_6$ alkyl, C$_1$-C$_6$ alkoxy, NH$_2$, —O(CH$_2$)$_n$R$_{10}$, —O(CHR$_9$)$_n$R$_{10}$, —O(CH$_2$)$_n$—O—(CH$_2$)$_m$R$_{10}$, —O(CH$_2$)$_n$C(O)NHR$_{10}$, —O(CH$_2$)$_n$C(O)R$_{10}$, NHR$_{11}$, —N(R$_{11}$)(R$_{12}$), —NHC(O)R$_{11}$, —NHS(O)R$_{11}$, —NHS(O)$_2$R$_{11}$, —NHC(O)OR$_{11}$, —NHC(O)NHR$_{11}$, —S(O)$_2$NHR$_{11}$, —NHC(O)N(R$_{12}$)R$_{11}$, OCH$_2$R$_{11}$, CHR$_9$R$_{10}$, or OCHR$_{10}$R$_{11}$, wherein C$_1$-C$_6$ alkyl, C$_1$-C$_6$ alkoxy, or benzyl is optionally substituted with one or more substituents selected from the group consisting of C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, C$_3$-C$_8$ cycloalkyl substituted with one or more halogen, 3- to 8-membered heterocyclyl, aryl, -heteroaryl-C(O)NH$_2$, and heteroaryl;

R$_3$ is H, C$_1$-C$_6$ alkyl, or —OH,

R$_4$ and R$_5$ are independently H, halogen, CH$_2$OH, C$_1$-C$_3$ alkyl, or C$_1$-C$_3$ alkyl substituted with halogen, or R$_4$ and R$_5$ when combined can form a C$_3$-C$_6$ cycloalkyl or C$_3$-C$_5$ heterocyclyl;

R$_6$, R$_7$, and R$_8$ are independently H, halogen, C$_1$-C$_6$ alkyl, C$_1$-C$_6$ alkyl substituted with halogen, C$_1$-C$_6$ alkoxy, C$_1$-C$_6$ alkoxy substituted with one or more halogen, C$_2$-C$_6$ alkenyl, C$_2$-C$_6$ alkynyl, C$_3$-C$_8$ cycloalkyl, 3- to 8-membered heterocyclyl, aryl, heteroaryl, —(CHR$_{11}$)$_n$S(O)$_2$R$_{12}$, OR$_{11}$, —NR$_{11}$C(O)R$_{12}$, S(O)$_2$NR$_{11}$R$_{12}$, or —C(O)NR$_{11}$R$_{12}$;

R$_9$ and R$_{10}$ at each occurrence are independently selected from the group consisting of H, CN, —CH$_2$CN, halogen, —NR$_{11}$R$_{12}$, —C(O)NR$_{11}$R$_{12}$, —NR$_{11}$C(O)R$_{12}$, CHCF$_2$, CF$_3$, C$_1$-C$_6$ alkyl, R$_{11}$S(O)$_2$—, C$_1$-C$_6$ alkoxy, C$_2$-C$_6$ alkenyl, C$_2$-C$_6$ alkynyl, C$_3$-C$_8$ cycloalkyl, C$_3$-C$_8$ cycloalkylalkyl, 3- to 8-membered heterocyclyl, aryl, and heteroaryl, wherein each C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, C$_3$-C$_8$ cycloalkylalkyl, 3- to 8-membered heterocyclyl, aryl, and heteroaryl, is optionally substituted with one or more substituents selected from the group consisting of OH, oxo, halogen, C$_1$-C$_6$ alkyl, C$_1$-C$_6$ alkoxy, NH$_2$, R$_{13}$S(O)$_2$—, CN, C$_3$-C$_8$ cycloalkyl, 3- to 8-membered heterocyclyl, aryl, heteroaryl, and R$_{13}$S(O)$_2$—;

R$_{11}$ and R$_{12}$ are independently H, C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, 3- to 8-membered heterocyclyl, aryl, and heteroaryl; or when combined R$_{11}$ and R$_{12}$ can form a 3- to 8-membered heterocyclyl or heteroaryl ring;

R$_{13}$ is independently H, C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, 3- to 8-membered heterocyclyl, aryl, or heteroaryl;

m is 0, 1, or 2;

n is 0, 1, or 2; and r is 0, 1, or 2.

Another aspect of the invention relates to pharmaceutical compositions of the Formula I:

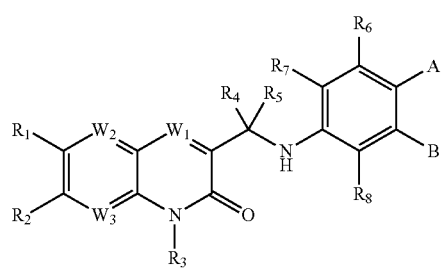

(I)

and pharmaceutically acceptable salts, enantiomers, hydrates, solvates, prodrugs, isomers, and tautomers thereof, wherein:

each W$_1$ and W$_2$ is independently CH, CF or N;

W$_3$ is independently CR$_2$, or N;

A is selected from the group consisting of H, D, halogen, CN, —CHO, —COOH, —COOR$_9$, —C(O)NH$_2$, —C(O)NHR$_9$, R$_{10}$S(O)$_2$—, —O(CH$_2$)$_n$C(O)R$_{10}$, —O(CH$_2$)C(O)NR$_{10}$R$_9$, R$_{10}$S(O)—, heteroaryl, —S(O)Me, —S(O)$_2$Me,

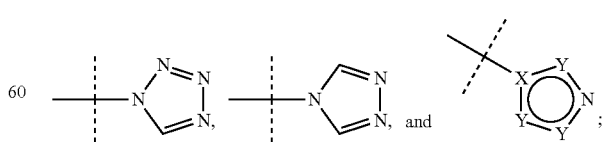

B is selected from the group consisting of:

H, D, OH, NO$_2$, NH$_2$, —NR$_{11}$R$_{12}$, CN, —(CH$_2$)$_n$CN, C$_1$-C$_6$ alkyl, C$_1$-C$_6$ haloalkyl, C$_3$-C$_8$ cycloalkyl, aryl, C$_1$-C$_6$ alkoxy, C$_1$-C$_6$ haloalkoxy, heteroaryl, —O(CH$_2$)$_n$R$_{10}$, —(CH$_2$)$_n$C(O)NHR$_9$, —C(O)NH$_2$, —SR$_9$, OR$_9$,
—(CHR$_{10}$)$_n$S(O)R$_9$, —(CHR$_{10}$)$_n$S(O)$_2$R$_9$, —S(O)$_2$NR$_9$R$_{10}$,
—COOR$_9$,

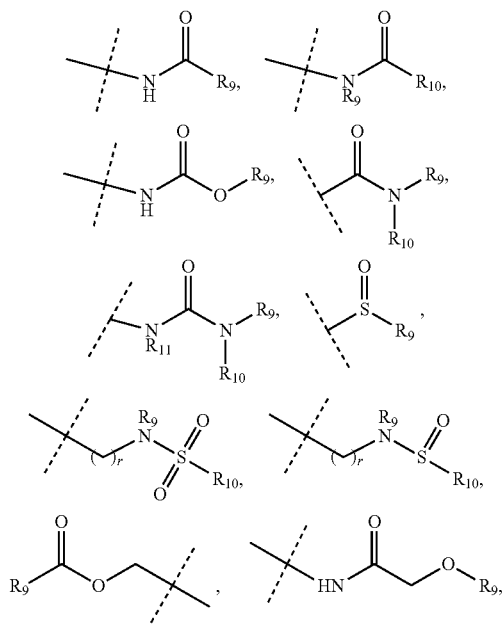

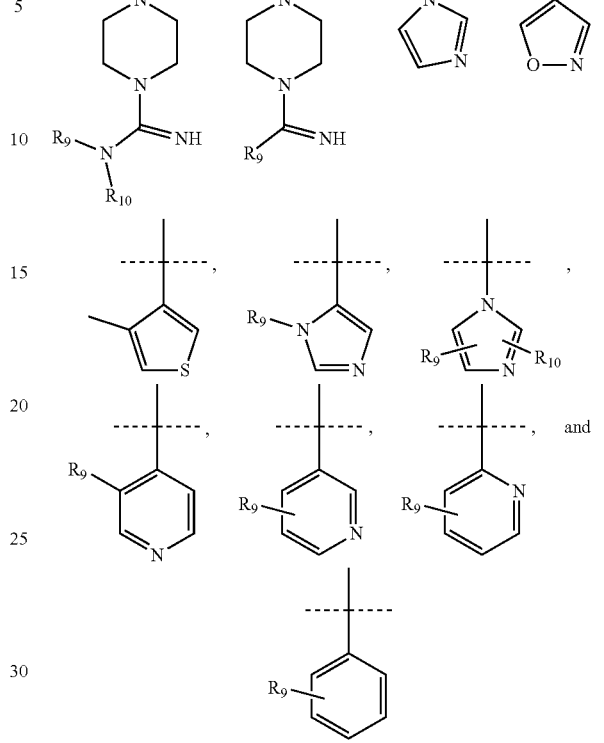

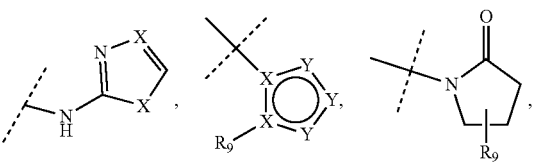

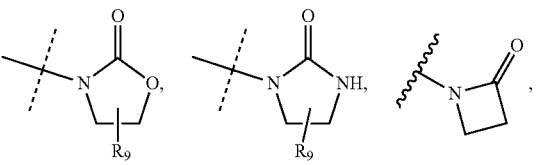

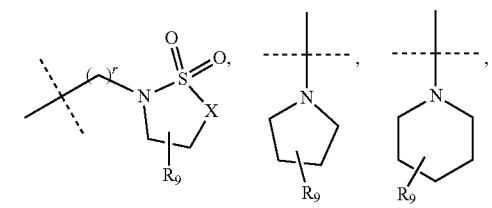

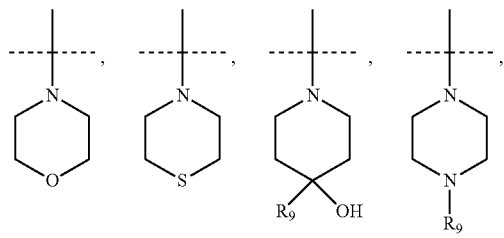

wherein X and Y are independently in each occurrence C, N, NR$_{10}$, S, and O, provided that the ring containing X and Y cannot have more than 4 N or NH atoms or more than one S or O atoms, and wherein the S and O are not contiguous;

R$_1$ is independently H, OH, CN, halogen, CHF$_2$, CF$_3$, C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, 3- to 8-membered heterocyclyl, aryl, or heteroaryl, wherein each C$_1$-C$_6$ alkyl, C$_2$-C$_6$ alkenyl, C$_2$-C$_6$ alkynyl, C$_3$-C$_8$ cycloalkyl, 3- to 8-membered heterocyclyl, aryl, or heteroaryl is optionally substituted one or more times with substituents selected from the group consisting of halogen, OH, NH$_2$, CN, C$_1$-C$_6$ alkyl, and C$_1$-C$_6$ alkoxy;

R$_2$ is independently H, OH, CN, halogen, CF$_3$, CHF$_2$, benzyl, C$_1$-C$_6$ alkyl, C$_1$-C$_6$ alkoxy, NH$_2$, —O(CH$_2$)$_n$R$_{10}$, —O(CHR$_9$)$_n$R$_{10}$, —O(CH$_2$)$_n$—O—(CH$_2$)$_m$R$_{10}$, —O(CH$_2$)$_n$C(O)NHR$_{10}$, —O(CH$_2$)C(O)R$_{10}$, NHR$_{11}$, —N(R$_{11}$)(R$_{12}$), NHC(O)R$_{11}$, NHS(O)R$_{11}$, NHS(O)$_2$R$_{11}$, NHC(O)OR$_{11}$, NHC(O)NHR$_{11}$, —S(O)$_2$NHR$_{11}$, NHC(O)N(R$_{12}$)R$_{11}$, OCH$_2$R$_{11}$, CHR$_9$R$_{10}$, or OCHR$_{10}$R$_{11}$, wherein C$_1$-C$_6$ alkyl, C$_1$-C$_6$ alkoxy, or benzyl is optionally substituted with one or more substituents selected from the group consisting of C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, C$_3$-C$_8$ cycloalkyl substituted with one or more halogen, 3- to 8-membered heterocyclyl, aryl, -heteroaryl-C(O)NH$_2$, and heteroaryl;

R$_3$ is H, C$_1$-C$_6$ alkyl, or —OH,

R$_4$ and R$_5$ are independently H, halogen, CH$_2$OH, C$_1$-C$_3$ alkyl, or C$_1$-C$_3$ alkyl substituted with halogen, or R$_4$ and R$_5$ when combined can form a C$_3$-C$_5$ cycloalkyl or C$_3$-C$_5$ heterocyclyl;

R$_6$, R$_7$, and R$_8$ are independently H, halogen, C$_1$-C$_6$ alkyl, C$_1$-C$_6$ alkyl substituted with halogen, C$_1$-C$_6$ alkoxy, C$_1$-C$_6$ alkoxy substituted with one or more halogen, C$_2$-C$_6$ alkenyl, $C_2$-$C_6$ alkynyl, $C_3$-$C_8$ cycloalkyl, 3- to 8-membered heterocyclyl, aryl, heteroaryl, —(CHR$_{11}$)$_n$S(O)$_2$R$_{12}$, OR$_{11}$—NR$_{11}$C(O)R$_{12}$, S(O)$_2$NR$_{11}$R$_{12}$, or —C(O)NR$_{11}$R$_{12}$;

R$_9$ and R$_{10}$ at each occurrence are independently selected from the group consisting of H, CN, —CH$_2$CN, halogen, —NR$_{11}$R$_{12}$, —C(O)NR$_{11}$R$_{12}$, —NR$_{11}$C(O)R$_{12}$, CHCF$_2$, CF$_3$, C$_1$-C$_6$ alkyl, R$_{11}$S(O)$_2$—, C$_1$-C$_6$ alkoxy, C$_2$-C$_6$ alkenyl, C$_2$-C$_6$ alkynyl, C$_3$-C$_8$ cycloalkyl, C$_3$-C$_8$ cycloalkylalkyl, 3- to 8-membered heterocyclyl, aryl, and heteroaryl, wherein each C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, C$_3$-C$_8$ cycloalkylalkyl, 3- to 8-membered heterocyclyl, aryl, and heteroaryl, is optionally substituted with one or more substituents selected from the group consisting of OH, oxo, halogen, C$_1$-C$_6$ alkyl, C$_1$-C$_6$ alkoxy, NH$_2$, R$_{13}$S(O)$_2$—, CN, C$_3$-C$_8$ cycloalkyl, 3- to 8-membered heterocyclyl, aryl, heteroaryl, and R$_{13}$S(O)$_2$—;

R$_{11}$ and R$_{12}$ are independently H, C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, 3- to 8-membered heterocyclyl, aryl, and heteroaryl; or when combined R$_{11}$ and R$_{12}$ can form a 3- to 8-membered heterocyclyl or heteroaryl ring;

R$_{13}$ is independently H, C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, 3- to 8-membered heterocyclyl, aryl, or heteroaryl;

m is 0, 1, or 2;
n is 0, 1, or 2; and
r is 0, 1, or 2;
provided that:
(1) when R$_1$ is H, then A is CN or tetrazole;
(2) when R$_1$ is H and A is tetrazole, then R$_2$ is not hydrogen, methyl or ethoxy;
(3) when R$_1$ and R$_2$ are H and A is tetrazole, then B and R$_6$ are H;
(4) when R$_1$ is H and R$_2$ is methyl, then neither B nor R$_6$ is methyl
(5) when R$_1$ is H and A is CN, then either B or R$_6$ is not H;
(6) when R$_1$ is C$_1$-C$_6$ alkoxy, then A is CN or imidazole;
(7) when R$_1$ is C$_1$-C$_6$ alkyl, then A is CN, tetrazole, or imidazole;
(8) when R$_1$ is methyl and A is tetrazole, then B and R$_6$ are H;
(9) when R$_1$ is C$_1$-C$_6$ alkyl and A is H, then B is —S(O)$_2$NR$_9$R$_{10}$;
(10) when R$_1$ is tert-butyl, then A is CN; or
(11) when R$_2$ is C$_1$-C$_6$ alkyl, then A is not H, halogen, or benzimidazole.

Another aspect of the invention relates to a method of treating a disease or disorder associated with mutant isocitrate dehydrogenase. The method involves administering to a patient in need of a treatment for diseases or disorders associated with mutant isocitrate dehydrogenase an effective amount of a compound of Formula I or composition of Formula I'.

Another aspect of the invention is directed to a method inhibiting mutant isocitrate dehydrogenase. The method involves administering to a patient in need thereof an effective amount of the compound of Formula I or composition of Formula I'.

Another aspect of the invention relates to method of reducing 2-hydroxyglutarate, comprising administering to a patient in need thereof an effective amount of the compound of Formula I or composition of Formula I'.

Another aspect of the invention is directed to pharmaceutical compositions comprising a compound of Formula I or I' and a pharmaceutically acceptable carrier. The pharmaceutical acceptable carrier may further include an excipient, diluent, or surfactant.

The present invention further provides methods of treating cell proliferative diseases and cancers including, without limitation, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), myeloproliferative disease (MPD), and other solid tumors.

The present invention also provides potent mt-IDH inhibitors with excellent drug-like properties to cancers and other cell proliferative disorders. The inhibitors of the present invention may target mutated IDH1 or IDH2.

The present invention further provides development of potent, orally active, and selective IDH inhibitors as therapeutic agents for various diseases or disorders including cancers. The invention also provides treatment for solid and hematologic cancers for which there are no currently targeted therapies available for patients suffering from these conditions or disorders.

BRIEF DESCRIPTION OF THE DRAWINGS OF THE INVENTION

DETAILED DESCRIPTION OF THE INVENTION

Figure 1:
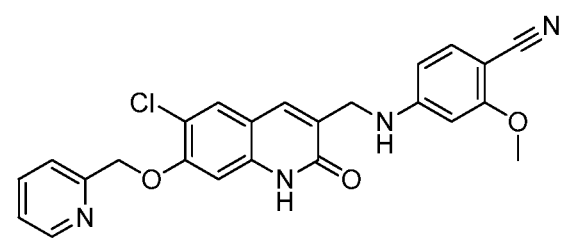
FIG. 1 illustrates the structure of compound I-58.
Figure 2:
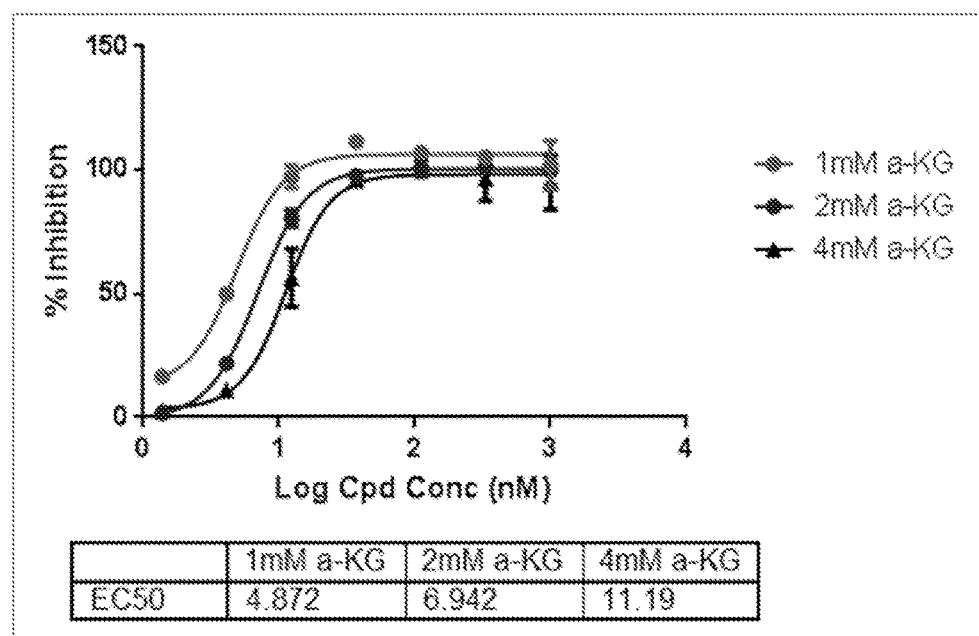
FIG. 2 illustrates a graph showing α-KG competition for the representative compound I-58 at varying concentrations of α-KG.
Figure 3:
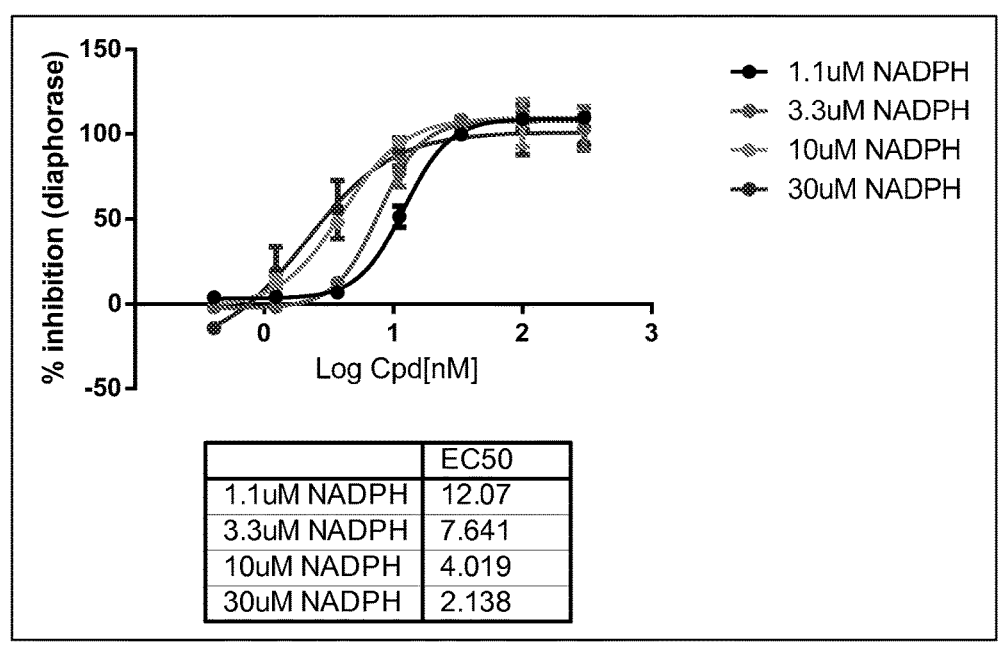
FIG. 3 illustrates a graph showing NADPH competition for the representative compound I-58 at varying concentrations of NADPH.

IDH1 or IDH2 mutations are a genetically validated target in many solid and hematologic cancers, but there are currently no targeted therapies available for patients in need of treatment for specific conditions associated with mt-IDH activity. Non-mutant IDH (e.g., wild-type) catalyze the oxidative decarboxylation of isocitrate to α-ketoglutarate thereby reducing NAD$^+$ (NADP$^+$) to NADH (NADPH) (WO 2013/102431 to Cianchetta et al., hereby incorporated by reference in its entirety). Mutations of IDH present in certain cancer cells result in a new ability of the enzyme to catalyze the NADPH-dependent reduction of α-ketoglutarate R(-)-2-hydroxyglutarate (2HG). 2HG is not formed by wild-type IDH. The production of 2HG contributes to the formation and progression of cancer (Dang, L et al., Nature, 2009, 462:739-44, hereby incorporated by reference in its entirety). The present invention provides inhibitors of mt-IDH, and prophylactic measures to reduce the formation and progression of 2HG in cells.

In a first aspect of the invention, are described the compounds of Formula I:

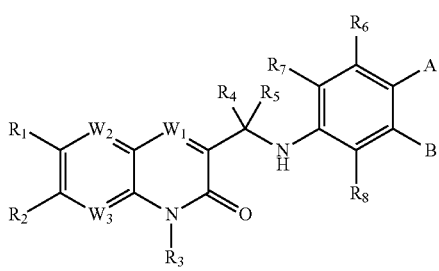

(I)

and pharmaceutically acceptable salts, enantiomers, hydrates, solvates, prodrugs, isomers, and tautomers thereof, where A, B, $W_1$, $W_2$, $W_3$, and $R_1$-$R_8$ are described as above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, CN, —COOH, —CH$_2$CN, —O—C$_1$-C$_6$alkyl, C$_1$-C$_6$alkyl, —OC$_1$-C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —NHC(O)C$_1$-C$_6$alkyl, —C(O)NHC$_1$-C$_6$alkyl, —S(O)$_2$—C$_1$-C$_6$alkyl, —S(O)NHC$_1$-C$_6$alkyl, and S(O)N(C$_1$-C$_6$alkyl)$_2$ Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—C$_1$-C$_6$alkyl, C$_1$-C$_6$alkyl, —OC$_1$-C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —S(O)$_2$—C$_1$-C$_6$alkyl, —S(O)NHC$_1$-C$_6$alkyl, and S(O)N(C$_1$-C$_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 10 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

Halogen or "halo" refers to fluorine, chlorine, bromine and iodine.

Alkyl refers to a straight or branched chain saturated hydrocarbon containing 1-12 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain. Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. Examples of alkenyl groups include ethenyl, propenyl, n-butenyl, iso-butenyl, pentenyl, or hexenyl.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2] octenyl.

"Cycloalkylalkyl" means monocyclic saturated carbon rings containing 3-18 carbon atoms further substituted with $C_1$-$C_6$ alkyl groups. In general cycloalkylalkyl groups herein described display the following formula

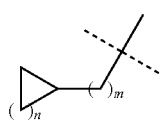

where m is an integer from 1 to 6 and n is an integer from 1 to 16.

"Heterocyclyl" or "heterocycloalkyl" monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. In accordance with the present invention, 3- to 8-membered heterocyclyl refers to saturated or partially saturated non aromatic rings structures containing between 3 and 8 atoms in which there is at least one heteroatoms selected from the group N, O, or S.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

In one embodiment of the invention, A is CN. In this embodiment, B may further be $C_1$-$C_6$ alkoxy or $C_1$-$C_6$ alkyl. In another embodiment, B may also be methoxy.

In another embodiment of the invention, A is CN and B is methyl.

In another embodiment, of the compounds of Formula I, B may be

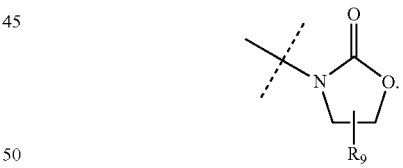

In this embodiment A may also be H or F. In this embodiment, $R_9$ may also be methyl, ethyl, or cyclopropyl.

In another embodiment of the compounds of Formula I, B is

In this embodiment, A may also be H or F. In this embodiment, $R_9$ may also be methyl, ethyl, or cyclopropyl.

In another embodiment of the compounds of Formula I, B is

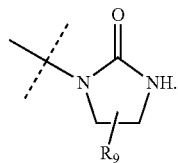

In this embodiment, A may also be H or F. In this embodiment, $R_9$ may also be methyl, ethyl, cyclopropyl, or $NR_{11}R_{12}$.

In another embodiment of the invention, A may be

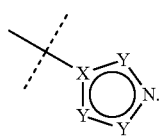

In this embodiment, B may also be H, $C_1$-$C_6$ alkoxy, or $C_1$-$C_6$ alkyl.

Yet another embodiment of the invention relates to compounds of Formula I where B is

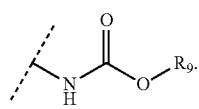

This embodiment also optionally provides for compounds of Formula I where A is H or F.

In another embodiment of the compounds of Formula I, B is

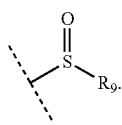

This embodiment may further provide for compounds of Formula I where A is H, or F, In another embodiment of the invention, B is

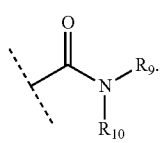

In this embodiment, A may also further be H, or F.

Another embodiment of the invention pertains to compounds of Formula I where $R_4$ and $R_5$ are H.

In another embodiment of the compounds of Formula I, $R_4$ is H and $R_5$ is methyl.

In yet another embodiment of the invention, $R_4$ is H and $R_5$ is (S)-methyl.

In another embodiment, $R_4$ and $R_5$ are halogen.

In another embodiment of the compounds of Formula I, $R_4$ is F and $R_5$ is methyl.

In another embodiment, $R_4$ and $R_5$ can combine to form a $C_3$-$C_5$ cycloalkyl.

In one embodiment of the compounds of Formula I, $W_1$, $W_2$, and $W_3$ are all CH.

In one embodiment of the compounds of Formula I, $W_1$, $W_2$, or $W_3$ is CF.

In one embodiment, $W_1$ or $W_3$ is CH, N.

In one embodiment, $W_3$ is $CR_2$.

In another embodiment of the invention, $R_1$ can be halogen. In another embodiment, $R_1$ is chloro.

In one embodiment, the compounds of the invention have the Formula Ia:

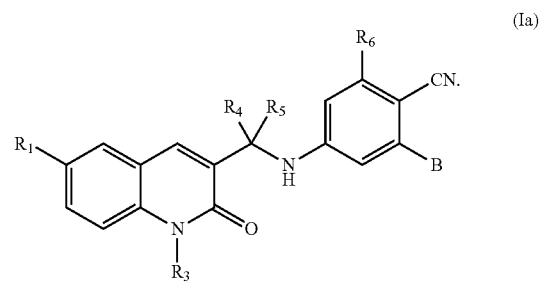

(Ia)

In one embodiment, the compounds of the invention have the Formula Ib:

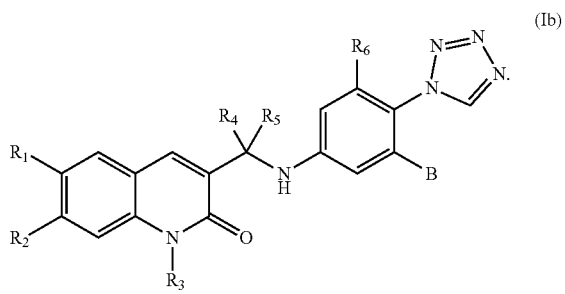

(Ib)

In one embodiment, the compounds of the invention have the Formula Ic:

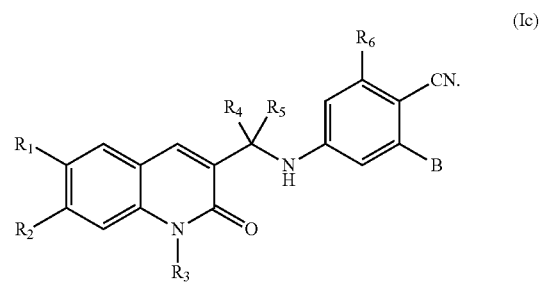

(Ic)

In one embodiment, the compounds of the invention have the Formula Id:

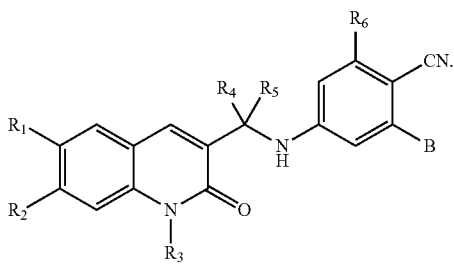

In one embodiment, the compounds of the invention have the Formula Ie:

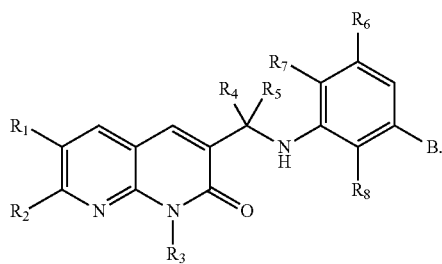

In one embodiment, the compounds of the invention have the Formula If:

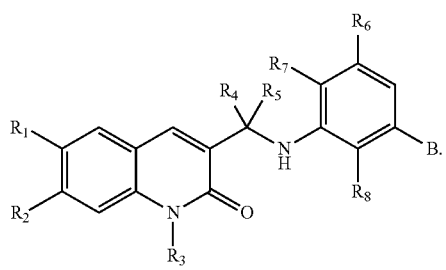

In one embodiment of the invention $R_2$ can be H, halogen, or $C_1$-$C_6$ alkoxy. In another embodiment, $R_2$ can also be $C_1$-$C_6$ alkoxy substituted with heteroaryl or 3- to 8-membered heterocyclyl.

In another embodiment, illustrative compounds of Formula I are:

4-{[(1S)-1-(6-chloro-2-oxo-1,2-dihydroquinolin-3-yl)ethyl]amino}-2-methoxybenzonitrile;
4-{[(1R)-1-(6-chloro-2-oxo-1,2-dihydroquinolin-3-yl)ethyl]amino}-2-methoxybenzonitrile;
4-{[(1S)-1-(6-chloro-2-oxo-1,2-dihydroquinolin-3-yl)ethyl]amino}-3-methanesulfonylbenzonitrile;
4-{[1-(6-chloro-2-oxo-1,2-dihydroquinolin-3-yl)ethyl]amino}-2-methoxybenzonitrile;
4-({1-[6-chloro-2-oxo-7-(pyridin-2-ylmethoxy)-1,2-dihydroquinolin-3-yl]ethyl}amino)-2-methoxybenzonitrile;
6-chloro-3-[(1S)-1-[(4-methanesulfonyl-3-methoxyphenyl)amino]ethyl]-1,2-dihydroquinolin-2-one;
4-{[(6-chloro-2-oxo-1,2-dihydroquinolin-3-yl)methyl]amino}-2-methoxybenzonitrile;
4-{[(6-chloro-2-oxo-1,2-dihydroquinolin-3-yl)methyl]amino}-2-hydroxybenzonitrile;
4-{[(6-chloro-2-oxo-1,2-dihydroquinolin-3-yl)methyl]amino}-2,6-dimethoxybenzonitrile;
4-{[(6-chloro-2-oxo-1,2-dihydroquinolin-3-yl)methyl]amino}-2-(trifluoromethoxy)benzonitrile;
4-{[(6-chloro-2-oxo-1,2-dihydroquinolin-3-yl)methyl]amino}-2-(2-hydroxyethoxy)benzonitrile;
6-chloro-3-({[4-(1H-imidazol-1-yl)-3-methoxyphenyl]amino}methyl)-1,2-dihydroquinolin-2-one;
4-{[(6-chloro-2-oxo-1,2-dihydroquinolin-3-yl)methyl]amino}-2-ethoxybenzonitrile;
2-(5-{[(6-chloro-2-oxo-1,2-dihydroquinolin-3-yl)methyl]amino}-2-cyanophenoxy)acetamide;
6-chloro-3-{[(4-methanesulfonyl-3-methoxyphenyl)amino]methyl}-1,2-dihydroquinolin-2-one;
6-chloro-3-({[3-methoxy-4-(1H-1,2,3,4-tetrazol-1-yl)phenyl]amino}methyl)-1,2-dihydroquinolin-2-one;
4-{[(6-chloro-2-oxo-1,2-dihydroquinolin-3-yl)methyl]amino}-3-methoxybenzonitrile;
4-{[(6-chloro-2-oxo-1,2-dihydroquinolin-3-yl)methyl]amino}-2-(trifluoromethyl)benzonitrile;
4-{[(6-chloro-2-oxo-1,2-dihydroquinolin-3-yl)methyl]amino}-2-methylbenzonitrile;
4-{[(6-chloro-2-oxo-1,2-dihydroquinolin-3-yl)methyl]amino}benzonitrile;
4-{[(6-chloro-2-oxo-1,2-dihydroquinolin-3-yl)methyl]amino}-2-fluorobenzonitrile;
6-chloro-3-({[4-(5-methyl-1H-1,2,3,4-tetrazol-1-yl)phenyl]amino}methyl)-1,2-dihydroquinolin-2-one;
6-chloro-3-({[4-(1H-imidazol-1-yl)phenyl]amino}methyl)-1,2-dihydroquinolin-2-one;
2-{[(6-chloro-2-oxo-1,2-dihydroquinolin-3-yl)methyl]amino}benzamide;
6-chloro-3-{[(4-fluoro-3-methoxyphenyl)amino]methyl}-1,2-dihydroquinolin-2-one;
4-{[(6-chloro-2-oxo-1,2-dihydroquinolin-3-yl)methyl]amino}-N-methylbenzamide;
2-(4-{[(6-chloro-2-oxo-1,2-dihydroquinolin-3-yl)methyl]amino}phenoxy)acetamide;
6-chloro-3-{[(4-chloro-3-methoxyphenyl)amino]methyl}-1,2-dihydroquinolin-2-one;
2-(3-{[(6-chloro-2-oxo-1,2-dihydroquinolin-3-yl)methyl]amino}phenyl)acetonitrile;
6-chloro-3-{[(2-fluorophenyl)amino]methyl}-1,2-dihydroquinolin-2-one;
3-({[3-methoxy-4-(1H-1,2,3,4-tetrazol-1-yl)phenyl]amino}methyl)-6-methyl-1,2-dihydroquinolin-2-one;
2-methoxy-4-{[(2-oxo-1,2-dihydroquinolin-3-yl)methyl]amino}benzonitrile;
3-({[3-methoxy-4-(1H-1,2,3,4-tetrazol-1-yl)phenyl]amino}methyl)-1,2-dihydroquinolin-2-one;
3-({[4-(1H-1,2,3,4-tetrazol-1-yl)phenyl]amino}methyl)-1,2-dihydroquinolin-2-one;
2-methoxy-4-{[(6-methyl-2-oxo-1,2-dihydroquinolin-3-yl)methyl]amino}benzonitrile;
4-{[(6,7-dimethyl-2-oxo-1,2-dihydroquinolin-3-yl)methyl]amino}-2-methoxybenzonitrile;
3-({[3-methoxy-4-(4-methyl-1H-imidazol-1-yl)phenyl]amino}methyl)-6-methyl-1,2-dihydroquinolin-2-one;
6,7-dimethyl-3-({[4-(1H-1,2,3,4-tetrazol-1-yl)phenyl]amino}methyl)-1,2-dihydroquinolin-2-one;
N-(3,4-dihydro-2H-pyrrol-5-yl)-3-{[(6,7-dimethyl-2-oxo-1,2-dihydroquinolin-3-yl)methyl]amino}benzene-1-sulfonamide;
3-({[3-methoxy-4-(1H-1,2,3,4-tetrazol-1-yl)phenyl]amino}methyl)-6,7-dimethyl-1,2-dihydroquinolin-2-one;
2-methoxy-4-{[(6-methoxy-2-oxo-1,2-dihydroquinolin-3-yl)methyl]amino}benzonitrile;

3-({[4-(1H-imidazol-1-yl)phenyl]amino}methyl)-6-methoxy-1,2-dihydroquinolin-2-one;
4-{[(6-chloro-7-methoxy-2-oxo-1,2-dihydroquinolin-3-yl)methyl]amino}-2-methoxybenzonitrile;
2-methoxy-4-{[(7-methyl-2-oxo-1,2-dihydroquinolin-3-yl)methyl]amino}benzonitrile;
3-({[3-methoxy-4-(1H-1,2,3,4-tetrazol-1-yl)phenyl]amino}methyl)-7-methyl-1,2-dihydroquinolin-2-one;
4-{[(6-bromo-2-oxo-1,2-dihydroquinolin-3-yl)methyl]amino}-2-methoxybenzonitrile;
4-{[(6-tert-butyl-2-oxo-1,2-dihydroquinolin-3-yl)methyl]amino}-2-methoxybenzonitrile;
2-methoxy-4-({[2-oxo-6-(trifluoromethyl)-1,2-dihydroquinolin-3-yl]methyl}amino)benzonitrile;
4-{[(6-fluoro-7-methoxy-2-oxo-1,2-dihydroquinolin-3-yl)methyl]amino}-2-methoxybenzonitrile;
4-{[(6-fluoro-2-oxo-1,2-dihydroquinolin-3-yl)methyl]amino}-2-methoxybenzonitrile;
4-{[(6-iodo-2-oxo-1,2-dihydroquinolin-3-yl)methyl]amino}-2-methoxybenzonitrile;
4-{[(6-ethoxy-2-oxo-1,2-dihydroquinolin-3-yl)methyl]amino}-2-methoxybenzonitrile;
4-{[(7-chloro-2-oxo-1,2-dihydroquinolin-3-yl)methyl]amino}-2-methoxybenzonitrile;
4-{[(7-hydroxy-2-oxo-1,2-dihydroquinolin-3-yl)methyl]amino}-2-methoxybenzonitrile;
2-methoxy-4-{[(7-methoxy-2-oxo-1,2-dihydroquinolin-3-yl)methyl]amino}benzonitrile;
4-{[(6-chloro-7-hydroxy-2-oxo-1,2-dihydroquinolin-3-yl)methyl]amino}-2-methoxybenzonitrile;
4-({[6-chloro-2-oxo-7-(pyridin-2-ylmethoxy)-1,2-dihydroquinolin-3-yl]methyl}amino)-2-methoxybenzonitrile;
4-{[(6-chloro-7-{[(2S)-1-methylpyrrolidin-2-yl]methoxy}-2-oxo-1,2-dihydroquinolin-3-yl)methyl]amino}-2-methoxybenzonitrile;
4-[({6-chloro-7-[2-hydroxy-3-(morpholin-4-yl)propoxy]-2-oxo-1,2-dihydroquinolin-3-yl}methyl)amino]-2-methoxybenzonitrile;
4-[({6-chloro-7-[2-(morpholin-4-yl)ethoxy]-2-oxo-1,2-dihydroquinolin-3-yl}methyl)amino]-2-methoxybenzonitrile;
4-({[6-chloro-2-oxo-7-(pyridin-3-ylmethoxy)-1,2-dihydroquinolin-3-yl]methyl}amino)-2-methoxybenzonitrile;
4-({[6-chloro-7-(oxan-4-ylmethoxy)-2-oxo-1,2-dihydroquinolin-3-yl]methyl}amino)-2-methoxybenzonitrile;
4-[({6-chloro-7-[2-(dimethylamino)ethoxy]-2-oxo-1,2-dihydroquinolin-3-yl}methyl)amino]-2-methoxybenzonitrile;
4-[({6-chloro-7-[2-(4-methanesulfonylpiperazin-1-yl)ethoxy]-2-oxo-1,2-dihydroquinolin-3-yl}methyl)amino]-2-methoxybenzonitrile;
4-({[6-chloro-2-oxo-7-(oxolan-3-ylmethoxy)-1,2-dihydroquinolin-3-yl]methyl}amino)-2-methoxybenzonitrile;
4-[({6-chloro-7-[(1-methylpiperidin-4-yl)oxy]-2-oxo-1,2-dihydroquinolin-3-yl}methyl)amino]-2-methoxybenzonitrile;
2-[(6-chloro-3-{[(4-cyano-3-methoxyphenyl)amino]methyl}-2-oxo-1,2-dihydroquinolin-7-yl)oxy]-N,N-dimethylacetamide;
2-[(6-chloro-3-{[(4-cyano-3-methoxyphenyl)amino]methyl}-2-oxo-1,2-dihydroquinolin-7-yl)oxy]acetamide;
4-({[6-chloro-7-[2-(morpholin-4-yl)-2-oxoethoxy]-2-oxo-1,2-dihydroquinolin-3-yl]methyl}amino)-2-methoxybenzonitrile;
4-[({6-chloro-7-[(1,5-dimethyl-1H-pyrazol-3-yl)methoxy]-2-oxo-1,2-dihydroquinolin-3-yl}methyl)amino]-2-methoxybenzonitrile;
4-({[7-(benzyloxy)-6-chloro-2-oxo-1,2-dihydroquinolin-3-yl]methyl}amino)-2-methoxybenzonitrile;
4-[({6-chloro-7-[(1-methylpiperidin-2-yl)methoxy]-2-oxo-1,2-dihydroquinolin-3-yl}methyl)amino]-2-methoxybenzonitrile;
4-[({6-chloro-7-[(2-methylpyridin-4-yl)methoxy]-2-oxo-1,2-dihydroquinolin-3-yl}methyl)amino]-2-methoxybenzonitrile;
4-({[6-chloro-2-oxo-7-(pyridin-4-ylmethoxy)-1,2-dihydroquinolin-3-yl]methyl}amino)-2-methoxybenzonitrile;
4-[({6-chloro-7-[(1,1-dioxo-1$\lambda^6$-thian-4-yl)methoxy]-2-oxo-1,2-dihydroquinolin-3-yl}methyl)amino]-2-methoxybenzonitrile;
4-({[6-chloro-2-oxo-7-(pyrazin-2-ylmethoxy)-1,2-dihydroquinolin-3-yl]methyl}amino)-2-methoxybenzonitrile;
4-[({6-chloro-7-[(1-methyl-1H-imidazol-5-yl)methoxy]-2-oxo-1,2-dihydroquinolin-3-yl}methyl)amino]-2-methoxybenzonitrile;
4-[({6-chloro-7-[(1-methyl-1H-imidazol-2-yl)methoxy]-2-oxo-1,2-dihydroquinolin-3-yl}methyl)amino]-2-methoxybenzonitrile;
5-{[(6-chloro-3-{[(4-cyano-3-methoxyphenyl)amino]methyl}-2-oxo-1,2-dihydroquinolin-7-yl)oxy]methyl}-1,2,4-oxadiazole-3-carboxamide;
4-[({6-chloro-2-oxo-7-[2-(pyridin-2-yl)ethoxy]-1,2-dihydroquinolin-3-yl}methyl)amino]-2-methoxybenzonitrile;
4-[({6-chloro-2-oxo-7-[2-(pyridin-4-yl)ethoxy]-1,2-dihydroquinolin-3-yl}methyl)amino]-2-methoxybenzonitrile;
4-[({6-chloro-7-[3-(dimethylamino)propoxy]-2-oxo-1,2-dihydroquinolin-3-yl}methyl)amino]-2-methoxybenzonitrile;
4-[({6-chloro-2-oxo-7-[3-(pyrrolidin-1-yl)propoxy]-1,2-dihydroquinolin-3-yl}methyl)amino]-2-methoxybenzonitrile;
4-[({6-chloro-2-oxo-7-[3-(piperidin-1-yl)propoxy]-1,2-dihydroquinolin-3-yl}methyl)amino]-2-methoxybenzonitrile;
4-[({6-chloro-2-oxo-7-[2-(pyrrolidin-1-yl)ethoxy]-1,2-dihydroquinolin-3-yl}methyl)amino]-2-methoxybenzonitrile;
4-[({6-chloro-2-oxo-7-[2-(2-oxopyrrolidin-1-yl)ethoxy]-1,2-dihydroquinolin-3-yl}methyl)amino]-2-methoxybenzonitrile;
4-[({6-chloro-2-oxo-7-[2-(piperidin-1-yl)ethoxy]-1,2-dihydroquinolin-3-yl}methyl)amino]-2-methoxybenzonitrile;
4-[({6-chloro-7-[2-(4-methylpiperazin-1-yl)ethoxy]-2-oxo-1,2-dihydroquinolin-3-yl}methyl)amino]-2-methoxybenzonitrile;
4-[({6-chloro-7-[2-(1H-imidazol-1-yl)ethoxy]-2-oxo-1,2-dihydroquinolin-3-yl}methyl)amino]-2-methoxybenzonitrile;
4-[({6-chloro-7-[2-(2-methyl-1H-imidazol-1-yl)ethoxy]-2-oxo-1,2-dihydroquinolin-3-yl}methyl)amino]-2-methoxybenzonitrile;
4-[({6-chloro-7-[2-(1,1-dioxo-1$\lambda^6$-thiomorpholin-4-yl)ethoxy]-2-oxo-1,2-dihydroquinolin-3-yl}methyl)amino]-2-methoxybenzonitrile;
4-[({6-chloro-7-[2-(3,5-dimethyl-1H-pyrazol-1-yl)ethoxy]-2-oxo-1,2-dihydroquinolin-3-yl}methyl)amino]-2-methoxybenzonitrile;
4-({[6-chloro-7-(2-ethoxyethoxy)-2-oxo-1,2-dihydroquinolin-3-yl]methyl}amino)-2-methoxybenzonitrile;
4-{[(6-chloro-8-methyl-2-oxo-1,2-dihydroquinolin-3-yl)methyl]amino}-2-methoxybenzonitrile;
4-{[(6-chloro-8-hydroxy-2-oxo-1,2-dihydroquinolin-3-yl)methyl]amino}-2-methoxybenzonitrile;

4-{[(6-chloro-8-methoxy-2-oxo-1,2-dihydroquinolin-3-yl)methyl]amino}-2-methoxybenzonitrile;
4-({[6-chloro-2-oxo-8-(pyridin-2-ylmethoxy)-1,2-dihydroquinolin-3-yl]methyl}amino)-2-methoxybenzonitrile;
4-[({6-chloro-8-[2-(morpholin-4-yl)ethoxy]-2-oxo-1,2-dihydroquinolin-3-yl}methyl)amino]-2-methoxybenzonitrile;
4-[({6-chloro-2-oxo-8-[2-(pyrrolidin-1-yl)ethoxy]-1,2-dihydroquinolin-3-yl}methyl)amino]-2-methoxybenzonitrile; and
2-methoxy-4-{[(2-oxo-1,2-dihydro-1,8-naphthyridin-3-yl)methyl]amino}benzonitrile.

In another embodiment, illustrative compounds of Formula I include:

4-{[(1S)-1-{6-chloro-2-oxo-7-[(pyridin-2-yl)methoxy]-1,2-dihydroquinolin-3-yl}ethyl]amino}-2-methoxybenzonitrile;
4-{[(1S)-1-(6-chloro-7-methoxy-2-oxo-1,2-dihydroquinolin-3-yl)ethyl]amino}-2-methoxybenzonitrile;
4-{[(1S)-1-[6-chloro-2-oxo-7-(propan-2-yloxy)-1,2-dihydroquinolin-3-yl]ethyl]amino}-2-methoxybenzonitrile;
4-{[(1S)-1-[6-chloro-7-(cyclopropylmethoxy)-2-oxo-1,2-dihydroquinolin-3-yl]ethyl]amino}-2-methoxybenzonitrile;
4-{[(1S)-1-(6-chloro-7-fluoro-2-oxo-1,2-dihydroquinolin-3-yl)ethyl]amino}-2-methoxybenzonitrile;
4-{[(1S)-1-(6-chloro-8-fluoro-2-oxo-1,2-dihydroquinolin-3-yl)ethyl]amino}-2-methoxybenzonitrile;
4-{[(1S)-1-(6-chloro-2-oxo-1,2-dihydro-1,8-naphthyridin-3-yl)ethyl]amino}-2-methoxybenzonitrile;
6-chloro-3-[(1S)-1-{[3-methoxy-4-(1H-1,2,3,4-tetrazol-1-yl)phenyl]amino}ethyl]-1,2-dihydro-1,8-naphthyridin-2-one;
4-{[(1S)-1-(7-chloro-3-oxo-3,4-dihydroquinoxalin-2-yl)ethyl]amino}-2-methoxybenzonitrile;
methyl N-(3-{[(1S)-1-(6-chloro-2-oxo-1,2-dihydroquinolin-3-yl)ethyl]amino}phenyl)carbamate
3-{[(1S)-1-(6-chloro-2-oxo-1,2-dihydroquinolin-3-yl)ethyl]amino}benzamide;
6-chloro-3-[(1S)-1-{[3-(5-methyl-1H-1,2,3,4-tetrazol-1-yl)phenyl]amino}ethyl]-1,2-dihydroquinolin-2-one;
N-(3-{[(1S)-1-(6-chloro-2-oxo-1,2-dihydroquinolin-3-yl)ethyl]amino}phenyl)acetamide;
6-chloro-3-[(1S)-1-{[3-(1H-imidazol-1-yl)phenyl]amino}ethyl]-1,2-dihydroquinolin-2-one;
6-chloro-3-[(1S)-1-{[3-(1,2-oxazol-4-yl)phenyl]amino}ethyl]-1,2-dihydroquinolin-2-one;
3-[(1S)-1-{[3-(1-benzyl-1H-imidazol-5-yl)phenyl]amino}ethyl]-6-chloro-1,2-dihydroquinolin-2-one;
6-chloro-3-[(1S)-1-{[3-(1-methyl-1H-imidazol-5-yl)phenyl]amino}ethyl]-1,2-dihydroquinolin-2-one;
6-chloro-3-[(1S)-1-{[3-(3-methylpyridin-4-yl)phenyl]amino}ethyl]-1,2-dihydroquinolin-2-one;
N-(3-{[(1S)-1-(6-chloro-2-oxo-1,2-dihydroquinolin-3-yl)ethyl]amino}phenyl)-N-(2-methylpropyl)methanesulfonamide;
methyl N-(3-{[(1S)-1-{6-chloro-2-oxo-7-[(pyridin-2-yl)methoxy]-1,2-dihydroquinolin-3-yl}ethyl]amino}phenyl)carbamate;
3-{[(1S)-1-{6-chloro-2-oxo-7-[(pyridin-2-yl)methoxy]-1,2-dihydroquinolin-3-yl}ethyl]amino}benzamide;
6-chloro-3-[(1S)-1-{[2-fluoro-3-(2-oxo-1,3-oxazolidin-3-yl)phenyl]amino}ethyl]-7-[(pyridin-2-yl)methoxy]-1,2-dihydroquinolin-2-one;
6-chloro-3-[(1S)-1-{[3-(5-methyl-1H-1,2,3,4-tetrazol-1-yl)phenyl]amino}ethyl]-7-[(pyridin-2-yl)methoxy]-1,2-dihydroquinolin-2-one;
N-(3-{[(1S)-1-{6-chloro-2-oxo-7-[(pyridin-2-yl)methoxy]-1,2-dihydroquinolin-3-yl}ethyl]amino}phenyl)acetamide;
6-chloro-3-[(1S)-1-{[3-(1H-imidazol-1-yl)phenyl]amino}ethyl]-7-[(pyridin-2-yl)methoxy]-1,2-dihydroquinolin-2-one;
6-chloro-3-[(1S)-1-{[3-(1,2-oxazol-4-yl)phenyl]amino}ethyl]-7-[(pyridin-2-yl)methoxy]-1,2-dihydroquinolin-2-one;
6-chloro-3-[(1S)-1-{[3-(4-methylthiophen-3-yl)phenyl]amino}ethyl]-7-[(pyridin-2-yl)methoxy]-1,2-dihydroquinolin-2-one;
3-[(1S)-1-{[3-(1-benzyl-1H-imidazol-5-yl)phenyl]amino}ethyl]-6-chloro-7-[(pyridin-2-yl)methoxy]-1,2-dihydroquinolin-2-one;
6-chloro-3-[(1S)-1-{[3-(1-methyl-1H-imidazol-5-yl)phenyl]amino}ethyl]-7-[(pyridin-2-yl)methoxy]-1,2-dihydroquinolin-2-one;
6-chloro-3-[(1S)-1-{[3-(3-methylpyridin-4-yl)phenyl]amino}ethyl]-7-[(pyridin-2-yl)methoxy]-1,2-dihydroquinolin-2-one;
N-(3-{[(1S)-1-{6-chloro-2-oxo-7-[(pyridin-2-yl)methoxy]-1,2-dihydroquinolin-3-yl}ethyl]amino}phenyl)-N-(2-methylpropyl)methanesulfonamide;
4-{[(1S)-1-(6-chloro-7-methoxy-2-oxo-1,2-dihydroquinolin-3-yl)ethyl]amino}-2-methylbenzonitrile;
methyl N-(3-{[(1S)-1-(6-chloro-7-methoxy-2-oxo-1,2-dihydroquinolin-3-yl)ethyl]amino}phenyl)carbamate;
3-{[(1S)-1-(6-chloro-7-methoxy-2-oxo-1,2-dihydroquinolin-3-yl)ethyl]amino}benzamide;
6-chloro-3-[(1S)-1-{[2-fluoro-3-(2-oxo-1,3-oxazolidin-3-yl)phenyl]amino}ethyl]-7-methoxy-1,2-dihydroquinolin-2-one;
6-chloro-7-methoxy-3-[(1S)-1-{[3-(5-methyl-1H-1,2,3,4-tetrazol-1-yl)phenyl]amino}ethyl]-1,2-dihydroquinolin-2-one;
N-(3-{[(1S)-1-(6-chloro-7-methoxy-2-oxo-1,2-dihydroquinolin-3-yl)ethyl]amino}phenyl)acetamide;
6-chloro-3-[(1S)-1-{[3-(1H-imidazol-1-yl)phenyl]amino}ethyl]-7-methoxy-1,2-dihydroquinolin-2-one;
6-chloro-7-methoxy-3-[(1S)-1-{[3-(1,2-oxazol-4-yl)phenyl]amino}ethyl]-1,2-dihydroquinolin-2-one;
6-chloro-7-methoxy-3-[(1S)-1-{[3-(4-methylthiophen-3-yl)phenyl]amino}ethyl]-1,2-dihydroquinolin-2-one;
3-[(1S)-1-{[3-(1-benzyl-1H-imidazol-5-yl)phenyl]amino}ethyl]-6-chloro-7-methoxy-1,2-dihydroquinolin-2-one;
6-chloro-7-methoxy-3-[(1S)-1-{[3-(1-methyl-1H-imidazol-5-yl)phenyl]amino}ethyl]-1,2-dihydroquinolin-2-one;
6-chloro-7-methoxy-3-[(1S)-1-{[3-(3-methylpyridin-4-yl)phenyl]amino}ethyl]-1,2-dihydroquinolin-2-one;
N-(3-{[(1S)-1-(6-chloro-7-methoxy-2-oxo-1,2-dihydroquinolin-3-yl)ethyl]amino}phenyl)-N-(2-methylpropyl)methanesulfonamide;
methyl N-(3-{[(1S)-1-[6-chloro-2-oxo-7-(propan-2-yloxy)-1,2-dihydroquinolin-3-yl]ethyl]amino}phenyl)carbamate;
3-{[(1S)-1-[6-chloro-2-oxo-7-(propan-2-yloxy)-1,2-dihydroquinolin-3-yl]ethyl]amino}benzamide;
6-chloro-3-[(1S)-1-{[2-fluoro-3-(2-oxo-1,3-oxazolidin-3-yl)phenyl]amino}ethyl]-7-(propan-2-yloxy)-1,2-dihydroquinolin-2-one;
6-chloro-3-[(1S)-1-{[3-(5-methyl-1H-1,2,3,4-tetrazol-1-yl)phenyl]amino}ethyl]-7-(propan-2-yloxy)-1,2-dihydroquinolin-2-one;
N-(3-{[(1S)-1-[6-chloro-2-oxo-7-(propan-2-yloxy)-1,2-dihydroquinolin-3-yl]ethyl]amino}phenyl)acetamide;

3-[(1S)-1-{[3-(1-benzyl-1H-imidazol-5-yl)phenyl]amino}ethyl]-6-chloro-7-(propan-2-yloxy)-1,2-dihydroquinolin-2-one;
6-chloro-3-[(1S)-1-{[3-(1-methyl-1H-imidazol-5-yl)phenyl]amino}ethyl]-7-(propan-2-yloxy)-1,2-dihydroquinolin-2-one;
6-{[(1S)-1-[6-chloro-7-(cyclopropylmethoxy)-2-oxo-1,2-dihydroquinolin-3-yl]ethyl]amino}-2-methylpyridine-3-carbonitrile;
methyl N-(3-{[(1S)-1-[6-chloro-7-(cyclopropylmethoxy)-2-oxo-1,2-dihydroquinolin-3-yl]ethyl]amino}phenyl)carbamate;
3-{[(1S)-1-[6-chloro-7-(cyclopropylmethoxy)-2-oxo-1,2-dihydroquinolin-3-yl]ethyl]amino}benzamide;
6-chloro-7-(cyclopropylmethoxy)-3-[(1S)-1-{[2-fluoro-3-(2-oxo-1,3-oxazolidin-3-yl)phenyl]amino}ethyl]-1,2-dihydroquinolin-2-one;
6-chloro-7-(cyclopropylmethoxy)-3-[(1S)-1-{[3-(5-methyl-1H-1,2,3,4-tetrazol-1-yl)phenyl]amino}ethyl]-1,2-dihydroquinolin-2-one;
N-(3-{[(1S)-1-[6-chloro-7-(cyclopropylmethoxy)-2-oxo-1,2-dihydroquinolin-3-yl]ethyl]amino}phenyl)acetamide;
6-chloro-7-(cyclopropylmethoxy)-3-[(1S)-1-{[3-(1H-imidazol-1-yl)phenyl]amino}ethyl]-1,2-dihydroquinolin-2-one;
N-(3-{[(1S)-1-[6-chloro-7-(cyclopropylmethoxy)-2-oxo-1,2-dihydroquinolin-3-yl]ethyl]amino}phenyl)-N-(2-methylpropyl)methanesulfonamide;
6-chloro-7-fluoro-3-[(1S)-1-{[3-methoxy-4-(1H-1,2,3,4-tetrazol-1-yl)phenyl]amino}ethyl]-1,2-dihydroquinolin-2-one;
methyl N-(3-{[(1S)-1-(6-chloro-7-fluoro-2-oxo-1,2-dihydroquinolin-3-yl)ethyl]amino}phenyl)carbamate;
3-{[(1S)-1-(6-chloro-7-fluoro-2-oxo-1,2-dihydroquinolin-3-yl)ethyl]amino}benzamide;
6-chloro-7-fluoro-3-[(1S)-1-{[2-fluoro-3-(2-oxo-1,3-oxazolidin-3-yl)phenyl]amino}ethyl]-1,2-dihydroquinolin-2-one;
6-chloro-7-fluoro-3-[(1S)-1-{[3-(5-methyl-1H-1,2,3,4-tetrazol-1-yl)phenyl]amino}ethyl]-1,2-dihydroquinolin-2-one;
N-(3-{[(1S)-1-(6-chloro-7-fluoro-2-oxo-1,2-dihydroquinolin-3-yl)ethyl]amino}phenyl)acetamide;
6-chloro-7-fluoro-3-[(1S)-1-{[3-(1H-imidazol-1-yl)phenyl]amino}ethyl]-1,2-dihydroquinolin-2-one;
6-chloro-7-fluoro-3-[(1S)-1-{[3-(1,2-oxazol-4-yl)phenyl]amino}ethyl]-1,2-dihydroquinolin-2-one;
6-chloro-7-fluoro-3-[(1S)-1-{[3-(4-methylthiophen-3-yl)phenyl]amino}ethyl]-1,2-dihydroquinolin-2-one;
3-[(1S)-1-{[3-(1-benzyl-1H-imidazol-5-yl)phenyl]amino}ethyl]-6-chloro-7-fluoro-1,2-dihydroquinolin-2-one;
6-chloro-7-fluoro-3-[(1S)-1-{[3-(1-methyl-1H-imidazol-5-yl)phenyl]amino}ethyl]-1,2-dihydroquinolin-2-one;
6-chloro-7-fluoro-3-[(1S)-1-{[3-(3-methylpyridin-4-yl)phenyl]amino}ethyl]-1,2-dihydroquinolin-2-one;
N-(3-{[(1S)-1-(6-chloro-7-fluoro-2-oxo-1,2-dihydroquinolin-3-yl)ethyl]amino}phenyl)-N-(2-methylpropyl)methanesulfonamide;
methyl N-(3-{[(1S)-1-(6-chloro-8-fluoro-2-oxo-1,2-dihydroquinolin-3-yl)ethyl]amino}phenyl)carbamate;
3-{[(1S)-1-(6-chloro-8-fluoro-2-oxo-1,2-dihydroquinolin-3-yl)ethyl]amino}benzamide;
6-chloro-8-fluoro-3-[(1S)-1-{[2-fluoro-3-(2-oxo-1,3-oxazolidin-3-yl)phenyl]amino}ethyl]-1,2-dihydroquinolin-2-one;
6-chloro-8-fluoro-3-[(1S)-1-{[3-(5-methyl-1H-1,2,3,4-tetrazol-1-yl)phenyl]amino}ethyl]-1,2-dihydroquinolin-2-one;
N-(3-{[(1S)-1-(6-chloro-8-fluoro-2-oxo-1,2-dihydroquinolin-3-yl)ethyl]amino}phenyl)acetamide;
6-chloro-8-fluoro-3-[(1S)-1-{[3-(1H-imidazol-1-yl)phenyl]amino}ethyl]-1,2-dihydroquinolin-2-one;
6-chloro-8-fluoro-3-[(1S)-1-{[3-(1,2-oxazol-4-yl)phenyl]amino}ethyl]-1,2-dihydroquinolin-2-one;
6-chloro-8-fluoro-3-[(1S)-1-{[3-(4-methylthiophen-3-yl)phenyl]amino}ethyl]-1,2-dihydroquinolin-2-one;
6-chloro-3-[(1S)-1-{[6-methoxy-5-(1H-1,2,3,4-tetrazol-1-yl)pyridin-2-yl]amino}ethyl]-1,2-dihydro-1,8-naphthyridin-2-one;
methyl N-(3-{[(1S)-1-(6-chloro-2-oxo-1,2-dihydro-1,8-naphthyridin-3-yl)ethyl]amino}phenyl)carbamate;
3-{[(1S)-1-(6-chloro-2-oxo-1,2-dihydro-1,8-naphthyridin-3-yl)ethyl]amino}benzamide;
6-chloro-3-[(1S)-1-{[2-fluoro-3-(2-oxo-1,3-oxazolidin-3-yl)phenyl]amino}ethyl]-1,2-dihydro-1,8-naphthyridin-2-one;
6-chloro-3-[(1S)-1-{[3-(5-methyl-1H-1,2,3,4-tetrazol-1-yl)phenyl]amino}ethyl]-1,2-dihydro-1,8-naphthyridin-2-one;
N-(3-{[(1S)-1-(6-chloro-2-oxo-1,2-dihydro-1,8-naphthyridin-3-yl)ethyl]amino}phenyl)acetamide;
6-chloro-3-[(1S)-1-{[3-(1H-imidazol-1-yl)phenyl]amino}ethyl]-1,2-dihydro-1,8-naphthyridin-2-one;
6-chloro-3-[(1S)-1-{[3-(1,2-oxazol-4-yl)phenyl]amino}ethyl]-1,2-dihydro-1,8-naphthyridin-2-one;
6-chloro-3-[(1S)-1-{[3-(4-methylthiophen-3-yl)phenyl]amino}ethyl]-1,2-dihydro-1,8-naphthyridin-2-one;
3-[(1S)-1-{[3-(1-benzyl-1H-imidazol-5-yl)phenyl]amino}ethyl]-6-chloro-1,2-dihydro-1,8-naphthyridin-2-one;
6-chloro-3-[(1S)-1-{[3-(1-methyl-1H-imidazol-5-yl)phenyl]amino}ethyl]-1,2-dihydro-1,8-naphthyridin-2-one;
6-chloro-3-[(1S)-1-{[3-(3-methylpyridin-4-yl)phenyl]amino}ethyl]-1,2-dihydro-1,8-naphthyridin-2-one;
N-(3-{[(1S)-1-(6-chloro-2-oxo-1,2-dihydro-1,8-naphthyridin-3-yl)ethyl]amino}phenyl)-N-(2-methylpropyl)methanesulfonamide;
6-chloro-3-[(1S)-1-{[6-methoxy-5-(1H-1,2,3,4-tetrazol-1-yl)pyridin-2-yl]amino}ethyl]-1,2-dihydroquinoxalin-2-one;
methyl N-(3-{[(1S)-1-(7-chloro-3-oxo-3,4-dihydroquinoxalin-2-yl)ethyl]amino}phenyl)carbamate;
6-chloro-3-[(1S)-1-{[2-fluoro-3-(2-oxo-1,3-oxazolidin-3-yl)phenyl]amino}ethyl]-1,2-dihydroquinoxalin-2-one;
6-chloro-3-[(1S)-1-{[3-(5-methyl-1H-1,2,3,4-tetrazol-1-yl)phenyl]amino}ethyl]-1,2-dihydroquinoxalin-2-one;
N-(3-{[(1S)-1-(7-chloro-3-oxo-3,4-dihydroquinoxalin-2-yl)ethyl]amino}phenyl)acetamide;
6-chloro-3-[(1S)-1-{[3-(1H-imidazol-1-yl)phenyl]amino}ethyl]-1,2-dihydroquinoxalin-2-one; and
6-chloro-3-[(1S)-1-{[3-(1,2-oxazol-4-yl)phenyl]amino}ethyl]-1,2-dihydroquinoxalin-2-one.

In another embodiment of the invention, the compounds of Formula I are enantiomers. In some embodiments the compounds are (S)-enantiomer. In other embodiments the compounds may also be (R)-enantiomer. In yet other embodiments, the compounds of Formula I may be (+) or (−) enantiomers.

In another embodiment of the invention, the compounds of Formula I contain isotopes of atoms forming the structure of Formula I. Isotopes herein means, each of two or more forms of the same element (e.g., H and D; $^{12}C$ and $^{13}C$) that contain equal numbers of protons but different numbers of neutrons in their nuclei, and hence differ in relative atomic mass.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis or trans configuration. All tautomeric forms are also intended to be included.

Methods of Using the Disclosed Compounds

Another aspect of the invention relates to a method of treating a disease or disorder associated with mutant isocitrate dehydrogenase. The method involves administering to a patient in need of a treatment for diseases or disorders associated with mutant isocitrate dehydrogenase an effective amount of the compositions and compounds of Formula I.

Another aspect of the invention is directed to a method inhibiting mutant isocitrate dehydrogenase. The method involves administering to a patient in need thereof an effective amount of the compositions or compounds of Formula I.

Examples of a mutant IDH protein having a neomorphic activity are mutant IDH1 and mutant IDH2. A neomorphic activity associated with mutant IDH1 and mutant IDH2 is the ability to produce 2-hydroxyglutarate (2-HG neomorphic activity), specifically R-2-HG (R-2-HG neomorphic activity). Mutations in IDH 1 associated with 2-HG neomorphic activity, specifically R-2-HG neomorphic activity, include mutations at residues 97, 100, and 132, e.g. G97D, R100Q, R132H, R132C, R132S, R132G, R132L, and R132V. Mutations in IDH2 associated with 2-HG neoactivity, specifically R-2-HG neomorphic activity, include mutations at residues 140 and 172, e.g. R140Q, R140G, R172K, R172M, R172S, R172G, and R172W.

Another aspect of the invention relates to method of reducing 2-hydroxyglutarate. The method comprises administering to a patient in need thereof an effective amount of the compositions or compounds of Formula I.

One therapeutic use of the compounds or compositions of the present invention which inhibit mt-IDH is to provide treatment to patients or subjects suffering from cell proliferative diseases and cancers including, without limitation, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), myeloproliferative disease (MPD), and other solid tumors. Targeted treatments for these cancers and cell proliferative diseases are not currently available to patients suffering from these conditions. Therefore, there is a need for new therapeutic agents selective to these conditions.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula I and a pharmaceutically acceptable carrier. The pharmaceutical acceptable carrier may further include an excipient, diluent, or surfactant.

Another aspect of the invention is directed to pharmaceutical compositions comprising a compound of Formula I' and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Method of Synthesizing the Compounds

The compounds of the present invention may be made by a variety of methods, including standard chemistry. Suitable synthetic routes are depicted in the Schemes given below.

The compounds of formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formula (I).

Those skilled in the art will recognize if a stereocenter exists in the compounds of formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention formula (I) can be synthesized by following the steps outlined in Schemes 1-3, which comprise different sequences of assembling intermediates II, III, IV, V and VI. Starting materials are either commercially available or made by known procedures in the reported literature or as illustrated.

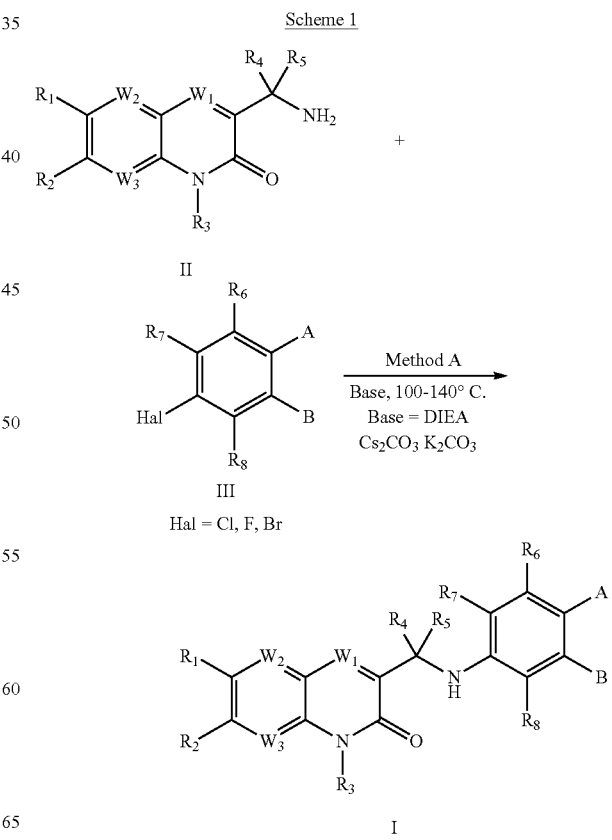

Scheme 1

Scheme 2

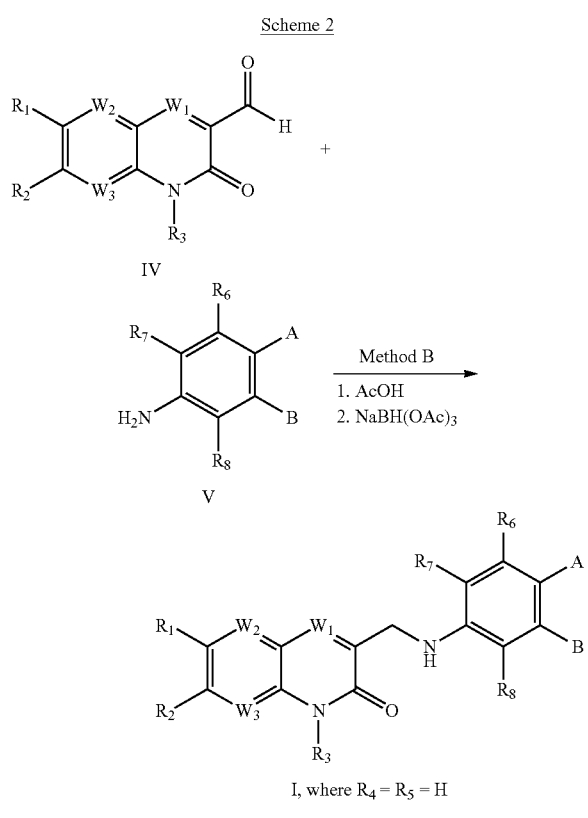

I, where $R_4 = R_5 = H$

Scheme 3

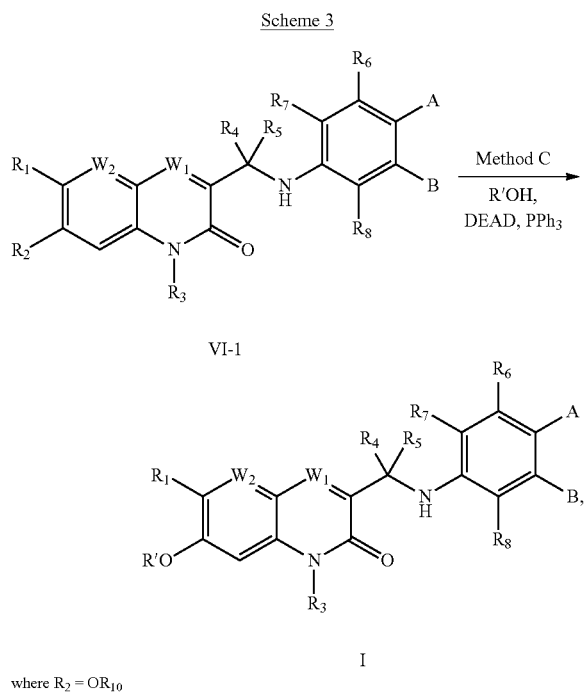

where $R_2 = OR_{10}$

Wherein A, B, $R_1$-$R_8$, and $W_{1-3}$ are defined in Formula (I).

The general ways of preparing target molecules I by using intermediates II, III, IV, V and VI are outlined in Scheme 1-3. Displacement of aryl halides (III) with intermediates amine (II) under standard nucleophilic substitution conditions using base such as N,N-diisopropylethylamine, and/or potassium carbonate, cesium carbonate in solvent DMSO or DMF gives the compounds of Formula I (Method A). Reductive amination of aldehyde (IV) with amine (V) is performed under standard procedure (AcOH and NaBH(OAc)$_3$) to prepare the compound of formula I (Method B). Mitsunobu reaction of intermediate (VI) with various alcohols give phenyl ether compounds of formula I (Method C). A mixture of enantiomers, diastereomers, cis/trans isomers resulted from the process can be separated into their single components by chiral salt technique, chromatography using normal phase, reverse phase or chiral column, depending on the nature of the separation.

It should be understood that in the description and formulae shown above, the various groups A, B, $W_1$, $W_2$, $W_3$, $R_1$-$R_8$ and other variables are as defined above, except where otherwise indicated. Furthermore, for synthetic purposes, the compounds of schemes 1, 2, and 3 are mere representative with elected radicals to illustrate the general synthetic methodology of the compound of formula I as defined herein.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Table 11 provides activity of illustrative compounds of Formula I in IDH1-R132H, IDH1-R132C, IDH1-MS-HTC116-R132H, and IDH1-MS-HTC116-R132C assays.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). High performance liquid chromatograph (HPLC) analyses were obtained using a XBridge Phenyl or C18 column (5 μm, 50×4.6 mm, 150×4.6 mm or 250×4.6 mm) with UV detection (Waters 996 PDA) at 254 nm or 223 nm using a standard solvent gradient program (Method 1-4).

LCMS Method 1 (ESI, 4 Min Method):
Instruments:

| HPLC: Waters HT2790 Alliance | MS: Waters ZQ Single Quad Mass Spectrometer |
|---|---|

UV: Waters 996 PDA
Conditions:

| Mobile phase A | 95% water/5% methanol with 0.1% Formic Acid |
| Mobile phase B (B) | 95% methanol/5% water with 0.1% Formic Acid |
| Column | XBridge Phenyl or C18, 5 μm 4.6 × 50 mm |

| | |
|---|---|
| Column temperature | Ambient |
| LC gradient | Linear 5-95% B in 2.5 min, hold 95% B to 3.5 min |
| LC Flow rate | 3 mL/min |
| UV wavelength | 220 nm and 254 nm |
| Ionization Mode | Electrospray Ionization; positive/negative |

LCMS Method 2 (ESI, 10 Min Method):
Instruments:

| | |
|---|---|
| HPLC: Waters HT2790 Alliance | MS: Waters ZQ Single Quad Mass Spectrometer |
| UV: Waters 996 PDA | |

Conditions:

| | |
|---|---|
| Mobile phase A (A) | 95% water/5% methanol with 0.1% Formic Acid |
| Mobile phase B (B) | 95% methanol/5% water with 0.1% Formic Acid |
| Column | XBridge C18, 5 µm 4.6 × 150 mm |
| Column temperature | Ambient |
| LC gradient | Linear 5-95% B in 5.5 min, hold 95% B to 7.5 min |
| LC Flow rate | 1.2 mL/min |
| UV wavelength | 220 nm and 254 nm |
| Ionization Mode | Electrospray Ionization; positive/negative |

LCMS Method 3: (APCI, 20 Min)
Instruments and Conditions:
HPLC-Agilent 1100 series.
Column: Agela Technologies Durashell C18, 3 µm, 4.6×50 mm).
Mobile Phase A: ACN+0.1% TFA.
Mobile Phase B: Water+0.1% TFA.

| | Time (min) | % B |
|---|---|---|
| Gradient: | 00 | 95 |
| | 15 | 05 |
| | 18 | 05 |
| | 20 | 95 |

Flow Rate: 1 mL/min.
Column Temperature: Ambient.
Detector: 254 nm.
LCMS Method 4 (ESI, 2.5 Min Method):
Instruments and Conditions:

| | |
|---|---|
| HPLC: Waters Acquity Binary Solvent Manager | MS: Waters ZQ Mass Detector |
| UV: Waters Acquity PDA | |
| Mobile phase A (A) | 95% water/5% acetonitrile with 0.1% formic acid in 10 mM ammonium formate |
| Mobile phase B (B) | 95% acetonitrile/5% water with 0.09% formic acid |
| Column | Waters Acquity UPLC BEH C18, 1.7 µm, 2.1 × 50 mm |
| Column temperature | 35° C. |
| LC gradient | 5-100% B in 2.0 min, hold 100% B to 2.2 min |
| LC Flow rate | 0.6 mL/min |
| UV wavelength | 220 nm and 254 nm |
| Ionization Mode | Electrospray Ionization; positive/negative |

Abbreviations Used in the Following Examples and Elsewhere Herein are:
Ac$_2$O acetic anhydride
ACN Acetonitrile
BOP ammonium 4-(3-(pyridin-3-ylmethyl)ureido)benzenesulfinate
CDCl$_3$ deuterated chloroform
Cs$_2$CO$_3$ cesium carbonate
CuSO$_4$ copper sulfate
δ chemical shift
DCM dichloromethane or methylene chloride
DCE 1,2-dichloroethane
DEAD diethyl azodicarboxylate
DIAD diisopropyl azodicarboxylate
DIEA N,N-diisopropylethylamine
DMA N,N-dimethylacetamide
DME dimethoxyethane
DMF N,N-dimethylformamide
DMP Dess-Martin Periodinane
DMSO dimethylsulfoxide
DMSO-d$_6$ deuterated dimethylsulfoxide
dppf 1,1'-Bis(diphenylphosphino)ferrocene
EDCI N-(3-dimethylaminopropyl)-N'-ethylcarbodiimide hydrochloride
EDTA ethylenediaminetetraacetic acid
ee enantiomeric excess
EtOAc ethyl acetate
EtOH ethanol
$^1$H NMR proton nuclear magnetic resonance
HOAc acetic acid
HATU 2-(3H-[1,2,3]triazolo[4,5-b]pyridin-3-yl)-1,1,3,3-tetramethylisouronium hexafluorophosphate
HCl hydrochloric acid
HOBT 1H-benzo[d][1,2,3]triazol-1-ol hydrate
HPLC high pressure liquid chromatography
Hz hertz
IPA isopropyl alcohol
KOAc potassium acetate
K$_2$CO$_3$ potassium carbonate
LAH lithium aluminum hydride
LCMS liquid chromatography/mass spectrometry
(M+1) mass+1
m-CPBA m-chloroperbenzoic acid
MeOH methanol
MeMgBr methyl magnesium bromide
MS mass spectrometry
NaBH$_4$ sodium borohydride
Na$_2$SO$_4$ sodium sulfate
Pd(dppf)Cl$_2$ [1,1'-Bis(diphenylphosphino)ferrocene]dichloropalladium(II)
Palladium tetrakis Tetrakis(triphenylphosphine)palladium(0)
Rt retention time
TBDMS-Cl Tert-butyl dimethylsilyl chloride
TEA triethylamine
THF tetrahydrofuran
TLC thin layer chromatography
Xantphos 4,5-Bis(diphenylphosphino)-9,9-dimethylxanthene Example 1—Intermediate II-1: (S)-3-(1-aminoethyl)-6-chloroquinolin-2(1H)-one hydrochloride

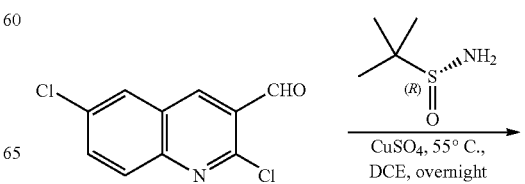

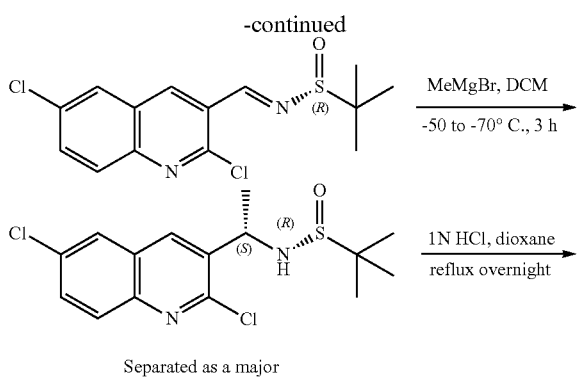

Separated as a major diastereomeric isomer

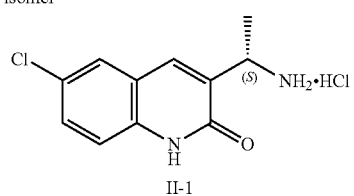

Step-1: (R,E)-N-((2,6-dichloroquinolin-3-yl)methylene)-2-methylpropane-2-sulfinamide

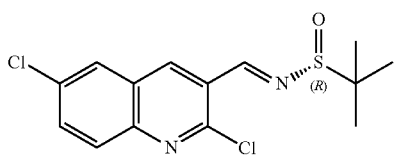

To a mixture of 2,6-dichloroquinoline-3-carbaldehyde (15.0 g, 66.37 mmol) and (R)-2-methylpropane-2-sulfinamide (8.85 g, 73.14 mmol) in 1,2-dichloroethane (150 mL) was added CuSO₄ (16.0 g, 100.25 mmol). The resulting mixture was heated to 55° C. and stirred at 55° C. overnight. After TLC and MS showed complete disappearance of starting materials, the mixture was cooled to room temperature and filtered through a pad of Celite®. The pad of celite was then rinsed with CH₂Cl₂. The filtrate was evaporated to dryness in vacuo and purified by SiO₂ column chromatography (0 to 25% hexanes/EtOAc) to afford the title compound, (R,E)-N-((2,6-dichloroquinolin-3-yl)methylene)-2-methylpropane-2-sulfinamide, as a yellow solid (17.7 g, 81% yield).

Step-2: (R)-N-((S)-1-(2,6-dichloroquinolin-3-yl)ethyl)-2-methylpropane-2-sulfinamide

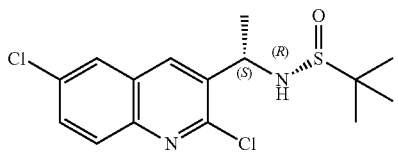

To a solution of (R,E)-N-((2,6-dichloroquinolin-3-yl)methylene)-2-methylpropane-2-sulfinamide (8.85 g, 26.88 mmol) in anhydrous CH₂Cl₂ (200 mL) at −60° C. was added dropwise MeMgBr (3M solution in diethyl ether, 13.5 mL, 40.54 mmol). The resulting reaction mixture was stirred at about −60 to −50° C. for 3 hours and then stirred at −20° C. overnight under an atmosphere of N₂. After TLC and MS showed complete disappearance of starting materials, saturated NH₄Cl (163 mL) was added at −20° C. and the resulting mixture was stirred for 10 minutes. The aqueous phase was extracted with CH₂Cl₂ (100 mL×3), dried over anhydrous Na₂SO₄, filtered, and evaporated. The residue was purified by column chromatography on an ISCO® chromatography system (SiO₂: Gold column; gradient; hexanes to 100% EtOAc) to provide the title compound, (R)-N-((S)-1-(2,6-dichloroquinolin-3-yl)ethyl)-2-methyl-propane-2-sulfinamide, as a yellow solid (5.8 g, 63% yield).

Step-3: (S)-3-(1-aminoethyl)-6-chloroquinolin-2(1H)-one hydrochloride (II-1)

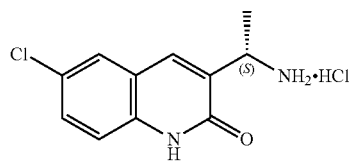

A mixture of (R)-N-((S)-1-(2,6-dichloroquinolin-3-yl)ethyl)-2-methylpropane-2-sulfinamide (6.6 g, 19.13 mmol) in 1,4-dioxane (41 mL) and 1N HCl (41 mL) was heated at reflux overnight. The solvents were evaporated in vacuo and the resulting residue was dissolved in hot water and lyophilized. The crude product was triturated with diethyl ether to afford the title compound II-1 as a yellow solid (9.0 g, ee: 98.4%). ¹H NMR (300 MHz, DMSO-d₆): δ ppm 12.4 (br s, 1H), 8.32 (br s, 2H), 8.07 (s, 1H), 7.85 (d, J=2.2 Hz, 1H), 7.63 (dd, J₁=8.8 Hz, J₂=2.5 Hz, 1H), 7.40 (d, J=8.8 Hz, 1H), 4.45-4.40 (m, 1H), 1.53 (d, J=8.5 Hz, 3H). LCMS (Method 3): Rt 3.42 min, m/z 223.1 [M+H]⁺.

Example 2—Intermediate II-2: (R)-3-(1-aminoethyl)-6-chloroquinolin-2(1H)-one hydrochloride

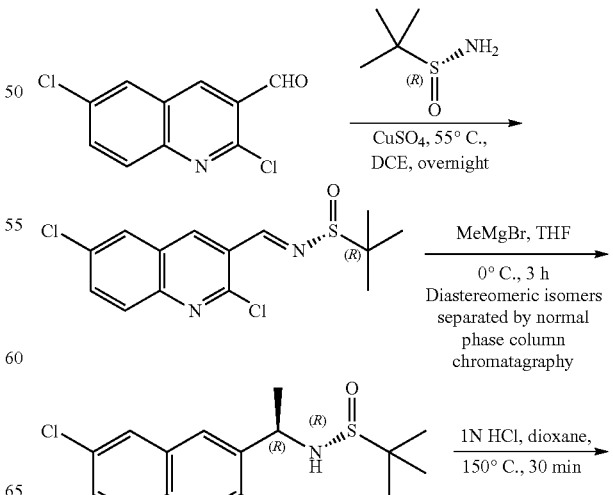

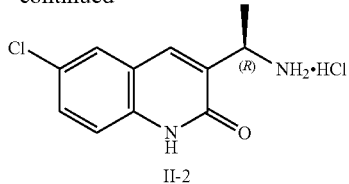

II-2

Step-1: (R)-N-((2,6-dichloroquinolin-3-yl)methylene)-2-methylpropane-2-sulfinamide To a mixture of 2,6-dichloroquinoline-3-carbaldehyde (500 mg, 2.21 mmol) and (R)-2-methylpropane-2-sulfinamide (295 g, 2.43 mmol) in 1,2-dichloroethane (15 mL) was added CuSO₄ (530 mg, 3.31 mmol). The resulting mixture was heated to 55° C. and stirred at 55° C. for 18 hours. Once TLC and MS showed complete disappearance of starting materials, the reaction mixture was cooled to room temperature and filtered through a pad of Celite®. The pad of celite was then rinsed with CH₂Cl₂. The filtrate was evaporated to dryness in vacuo and purified by column chromatography on an ISCO® chromatography system (SiO₂; hexanes to 60% EtOAc/hexanes) to afford the title compound, (R)-N-((2,6-dichloroquinolin-3-yl)methylene)-2-methylpropane-2-sulfinamide, as a yellow solid (510 mg, 70% yield).

Step-2: (R)-N-((R)-1-(2,6-dichloroquinolin-3-yl)ethyl)-2-methylpropane-2-sulfinamide To a solution of (R)-N-((2,6-dichloroquinolin-3-yl)methylene)-2-methylpropane-2-sulfinamide (505 mg, 1.534 mmol) in anhydrous THF (8 mL) at 0° C. was added dropwise MeMgBr (3M solution in diethyl ether, 0.56 mL, 1.687 mmol). The mixture was stirred at 0° C. for 3 hours under an atmosphere of N₂. After TLC and MS showed complete disappearance of starting materials, saturated NH₄Cl (5 mL) was added at 0° C. and the resulting mixture was stirred for 10 minutes. The aqueous phase was extracted with EtOAc (10 mL×3), dried over anhydrous Na₂SO₄, filtered, and evaporated. The residue was purified by column chromatography on an ISCO® chromatography system (SiO₂; hexanes to 80% EtOAc/hexanes) to afford the title compound as the R,R isomer as a pale yellow solid (200 mg, 38%) and the R,S isomer as a pale yellow solid (93 mg, 18% yield).

Step-3: (R)-3-(1-aminoethyl)-6-chloroquinolin-2(1H)-one hydrochloride (II-2)

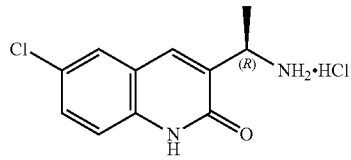

A mixture of (R)-N-((R)-1-(2,6-dichloroquinolin-3-yl)ethyl)-2-methylpropane-2-sulfinamide (190 mg, 0.55 mmol) in 1,4-dioxane (2 mL) and 1N HCl (1.1 mL, 1.1 mmol) was heated to 150° C. for 30 minutes in a microwave reactor. The solvents were evaporated and the residue was dissolved in hot water and lyophilized to afford the title compound II-2 as a yellow solid (148 mg, quantitative yield). ¹H NMR (300 MHz, DMSO-d₆): δ ppm 12.35 (br s, 1H), 8.28 (br s, 2H), 8.05 (s, 1H), 7.86 (d, J=2.2 Hz, 1H), 7.63 (dd, J₁=8.8 Hz, J₂=2.5 Hz, 1H), 7.40 (d, J=8.8 Hz, 1H), 4.45-4.40 (m, 1H), 1.53 (d, J=8.5 Hz, 3H). LCMS (Method 3): Rt 3.40 min, m/z 223.1 [M+H]⁺.

Example 3—An Alternative Approach to Intermediate II-1

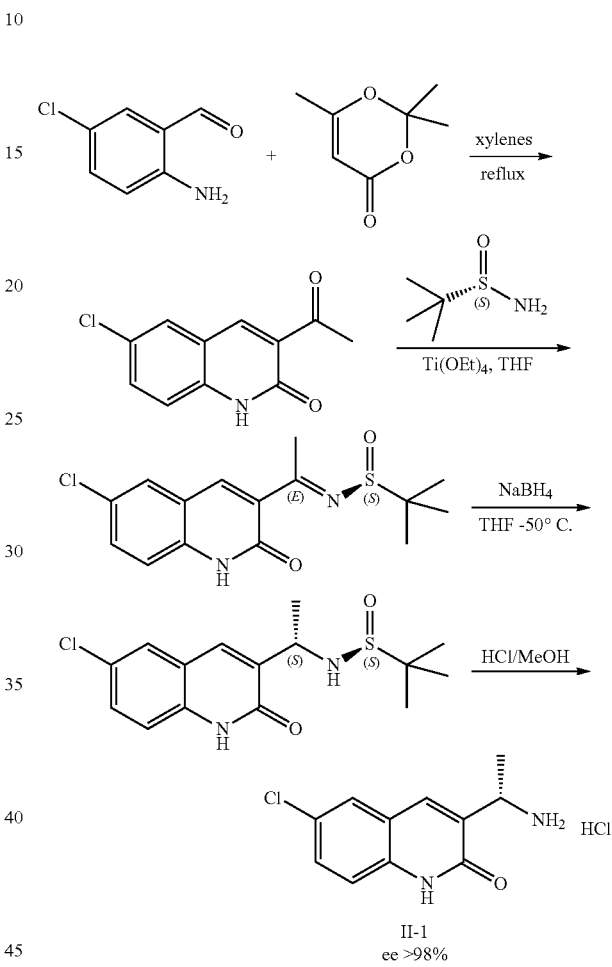

II-1
ee >98%

Step-1: 3-acetyl-6-chloroquinolin-2(1H)-one

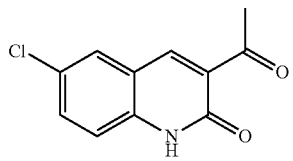

A mixture of 2-amino-5-chlorobenzaldehyde (0.5 g, 3.21 mmol) and 2,2,6-trimethyl-4H-1,3-dioxin-4-one (0.594 g, 4.18 mmol) in xylenes (10 mL) under an atmosphere of nitrogen was heated to reflux for 3 hours and then cooled to room temperature. The reaction mixture was filtered and washed with xylenes twice to afford the title compound, 3-acetyl-6-chloroquinolin-2(1H)-one (330 mg, 46.3%). ¹H NMR (300 MHz, DMSO-d₆): δ ppm 12.22 (br, 1H), 8.41 (s, 2H), 8.00 (s, 1H), 7.63 (d, J=8.8 Hz, 1H), 7.32 (dd, J₁=8.8 Hz, J₂=2.5 Hz, 1H), 2.58 (s, 3H). LCMS (Method 1): m/z 222.94 [M+H]⁺.

Step-2: ((S)-N-((S)-1-(6-chloro-2-oxo-1,2-dihydroquinolin-3-yl)ethyl)-2-methyl propane-2-sulfinamide

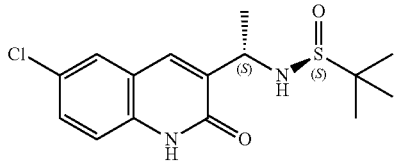

A mixture of tetraethoxytitanium (144 mg, 0.632 mmol), (S)-2-methylpropane-2-sulfinamide (38.3 mg, 0.316 mmol), and 3-acetyl-6-chloroquinolin-2(1H)-one (70 mg, 0.316 mmol) in THF (20 mL) was heated to 80° C. overnight and then cooled to room temperature. To this mixture was added NaBH₄ (59.7 mg, 1.579 mmol) at −50° C. The mixture was then slowly warmed up to room temperature overnight. MeOH (2 mL) was added to quench excess NaBH₄ and was followed by the addition of water. The resulting mixture was filtered to remove solids and the aqueous phase was extracted with EtOAc twice, dried over Na₂SO₄ and concentrated. The residue was purified on a Biotage® chromatography system using a 25 g SiO₂ column with gradient elution (20% to 100% EtOAc/Hexanes, then 0-5% MeOH/DCM) to afford (S)-N-((S)-1-(2,6-dichloroquinolin-3-yl)ethyl)-2-methylpropane-2-sulfinamide (39 mg, 38% yield). ¹H NMR (300 MHz, DMSO-d₆): δ ppm 12.05 (br, 1H), 7.95 (s, 1H), 7.84 (s, 1H), 7.38 (d, J=8.8 Hz, 1H), 5.76 (d, J=8.06 Hz, 1H), 5.37 (m, 1H), 4.55 (m, 1H), 1.44 (d, J=6.82 Hz, 3H), 1.18 (s, 9H). LCMS (Method 1): Rt 2.22 min; m/z 327.96 [M+H]⁺.

Step-3: (S)-3-(1-aminoethyl)-6-chloroquinolin-2(1H)-one hydrochloride (II-1)

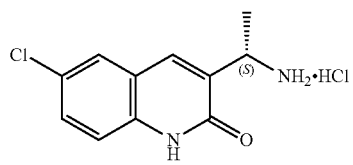

To a solution of ((S)-N-((S)-1-(6-chloro-2-oxo-1,2-dihydroquinolin-3-yl)ethyl)-2-methyl propane-2-sulfinamide (150 mg, 0.459 mmol) in MeOH (5 mL) was added HCl (2 mL, 8.0 mmol, 4M in 1,4-dioxane). The mixture was stirred at room temperature overnight. To this mixture was added 6 mL of ethyl ether and the resulting precipitate was collected by filtration, washed with ethyl ether (2×), and then dried to afford (S)-3-(1-aminoethyl)-6-chloroquinolin-2(1H)-one hydrochloride (50 mg, 42% yield). ¹H NMR (300 MHz, DMSO-d₆): δ ppm 12.4 (br s, 1H), 8.32 (br s, 2H), 8.07 (s, 1H), 7.85 (d, J=2.2 Hz, 1H), 7.63 (dd, J₁=8.8 Hz, J₂=2.5 Hz, 1H), 7.40 (d, J=8.8 Hz, 1H), 4.45-4.40 (m, 1H), 1.53 (d, J=8.5 Hz, 3H). LCMS (Method 1): Rt 1.22 min, m/z 223.1 [M+H]⁺. The enantiomer purity (ee %) of II-1 (>98%) was determined by chiral HPLC analysis.

Example 4—Alternate Approach (R)-3-(1-aminoethyl)-6-chloroquinolin-2(1H)-one hydrochloride (II-2)

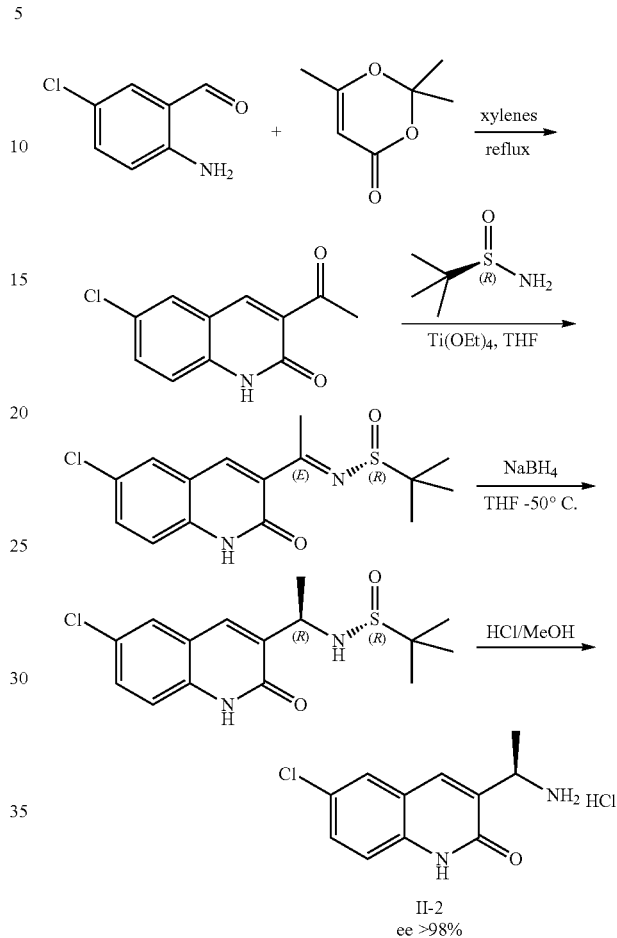

Step-1: ((R)-N-((R)-1-(6-chloro-2-oxo-1,2-dihydroquinolin-3-yl)ethyl)-2-methyl propane-2-sulfinamide

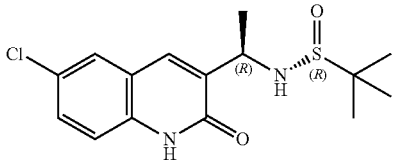

A mixture of tetraethoxytitanium (412 mg, 1.805 mmol) (R)-2-methylpropane-2-sulfinamide (131 mg, 1.083 mmol) and 3-acetyl-6-chloroquinolin-2(1H)-one (160 mg, 0.722 mmol) in THF (20 mL) was heated to 80° C. overnight, then cooled to room temperature. To this mixture was added NaBH₄ (137 mg, 3.61 mmol) −50° C. The mixture was then slowly warmed up to room temperature overnight. MeOH (2 mL) was added to quench excess NaBH₄ and was followed by the addition of water. The resulting mixture was filtered to remove solids and the aqueous phase was extracted with EtOAc twice, dried over Na₂SO₄ and concentrated. The residue was purified on a Biotage® chromatography system using a 25 g SiO₂ column with gradient elution (20 to 100% EtOAc/Hexanes, then 0-5% MeOH/DCM) to afford ((R)-N-((R)-1-(6-chloro-2-oxo-1,2-dihydroquinolin-3-yl)ethyl)-2-methyl propane-2-sulfinamide (157 mg, 66% yield). ¹H NMR (300 MHz, CDCl₃): δ ppm 11.31 (br, 1H), 7.35 (s, 1H), 7.22-7.07 (m, 2H), 5.86 (d, J=9.3 Hz, 1H), 5.37 (m, 1H), 4.55 (m, 1H), 1.56 (d, J=6.94 Hz, 3H), 1.32 (s, 9H). LCMS (Method 1): Rt 2.20 min, m/z 327.96 [M+H]⁺.

Step-2: (R)-3-(1-aminoethyl)-6-chloroquinolin-2(1H)-one hydrochloride (II-2)

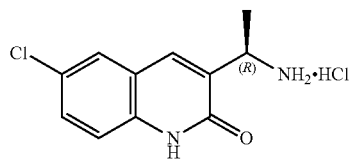

To a solution of (R)-N-((R)-1-(6-chloro-2-oxo-1,2-dihydroquinolin-3-yl)ethyl)-2-methylpropane-2-sulfinamide (150 mg, 0.459 mmol) in MeOH (5 mL) was added HCl (2 mL, 8.00 mmol, 4M in 1,4-dioxane). The mixture was stirred at room temperature overnight. To this mixture was added 6 mL of ethyl ether and the resulting precipitate was collected by filtration, washed with ethyl ether (2×), and then dried to afford (R)-3-(1-aminoethyl)-6-chloroquinolin-2(1H)-one hydrochloride (80 mg, 67% yield). ¹H NMR (300 MHz, DMSO-d₆): δ ppm 12.32 (br s, 1H), 8.34 (br, 2H), 8.06 (s, 1H), 7.81 (s, 1H), 7.58 (d, J=8.82 Hz, 1H), 7.31 (d, J=8.83 Hz, 1H), 4.45-4.40 (m, 1H), 1.53 (d, J=6.81 Hz, 3H). LCMS (Method 1): Rt 1.20 min, m/z 223.1 [M+H]⁺. The enantiomer purity (ee %) of II-2 (>98%) was determined by chiral HPLC analysis.

Example 5—Intermediate II-3: 3-(1-aminoethyl)-6-chloro-7-methoxyquinolin-2(1H)-one

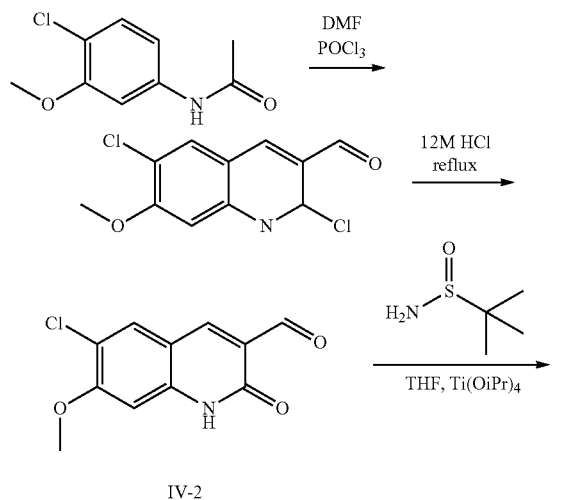

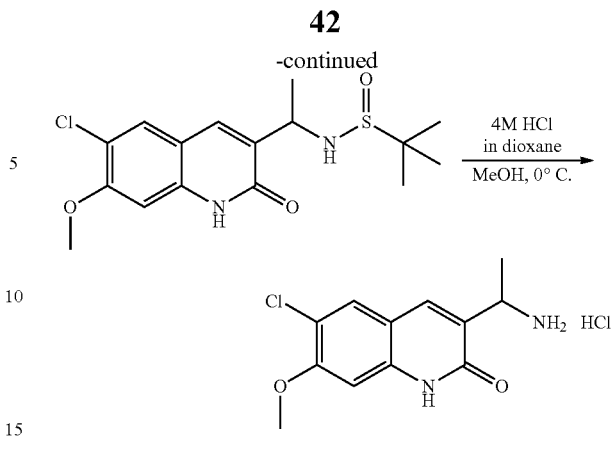

Step 1: 2,6-dichloro-7-methoxyquinoline-3-carbaldehyde

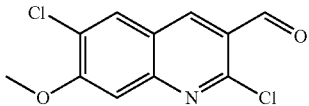 [SMILES: COc1cc2nc(Cl)c(C=O)cc2cc1Cl]

A tube was capped with a septum and placed under an atmosphere of nitrogen. DMF (6.4 mL, 83 mmol) was added by syringe and then cooled on an ice bath. POCl₃ (25 mL, 268 mmol) was added dropwise by syringe (over 20 minutes). The red solution was allowed to warm to room temperature (over 20 minutes), then the septum was removed, and the mixture was treated with N-(4-chloro-3-methoxyphenyl)acetamide (5 g, 25.05 mmol). The tube was sealed and the solution was stirred at 80° C. overnight. The solution was then pipetted onto ice, resulting in formation of a yellow precipitate. The precipitate was collected on a Buchner funnel, washed with water (1200 mL), and dried to provide 5.06 g of the title compound as a pale yellow solid. LCMS and ¹H NMR are consistent with 2,6-dichloro-7-methoxyquinoline-3-carbaldehyde (5.06 g, 19.76 mmol, 79% yield). ¹H NMR (300 MHz, DMSO-d₆): δ ppm 10.33 (s, 1H), 8.87 (s, 1H), 8.47 (s, 1H), 7.64 (s, 1H), 4.08 (s, 3H). LCMS (Method 1): m/z 256 [M+H]⁺.

Step-2: 6-chloro-7-methoxy-2-oxo-1,2-dihydroquinoline-3-carbaldehyde V-2

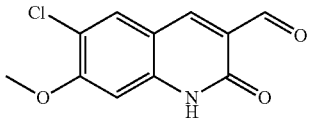 [SMILES: COc1cc2[nH]c(=O)c(C=O)cc2cc1Cl]

2,6-Dichloro-7-methoxyquinoline-3-carbaldehyde (5.06 g, 19.76 mmol) was heated at reflux in concentrated HCl (12M, 185 mL) overnight. The material went into solution during heating and then a solid precipitated during the course of the reaction. The mixture was allowed to cool and then was poured into water (1500 mL) resulting in further precipitation. The slurry was filtered on a Buchner funnel, washed with water (1500 mL), and dried to provide 4.04 g of the title compound as a yellowish-brown solid. LCMS and ¹H NMR are consistent with 6-chloro-7-methoxy-2-oxo-1,2-dihydroquinoline-3-carbaldehyde (4.04 g, 17.00 mmol, 86% yield). ¹H NMR (300 MHz, DMSO-d₆): δ ppm 12.22 (s, 1H), 10.18-10.16 (m, 1H), 8.43 (s, 1H), 8.08 (s, 1H), 6.95 (s, 1H), 3.94 (s, 3H). LCMS (Method 1): m/z 238 [M+H]⁺.

Step-3: N-((6-chloro-7-methoxy-2-oxo-1,2-dihydroquinolin-3-yl)methylene)-2-methylpropane-2-sulfinamide

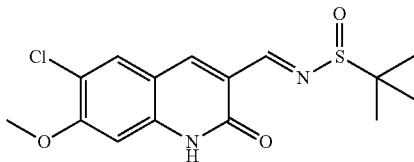 [SMILES: COc1cc2[nH]c(=O)c(/C=N/S(=O)C(C)(C)C)cc2cc1Cl]

A mixture of 6-chloro-7-methoxy-2-oxo-1,2-dihydroquinoline-3-carbaldehyde (2.00 g, 8.42 mmol) and 2-methylpropane-2-sulfinamide (1.22 g, 10.07 mmol) was placed under an atmosphere of nitrogen. THF (20 mL) and titanium (IV) isopropoxide (Ti(O$^i$Pr)$_4$) (5.0 mL, 17.06 mmol) were added by syringe and the resulting suspension was stirred at room temperature overnight. Once LCMS indicated the reaction had gone to completion, the reaction was quenched by dropwise addition of aqueous saturated NH$_4$Cl (10 mL). The mixture was triturated with EtOAc (450 mL), then filtered through Celite® 545, and the Celite® was washed further with EtOAc (200 mL). The filter cake was then sonicated in EtOAc (450 mL) for 15 minutes, then filtered on a Buchner funnel. The two filtrates were combined, washed with brine (200 mL), dried (Na$_2$SO$_4$), filtered, and evaporated under reduced pressure to provide 1.01 g of the title compound as a yellow solid. LCMS and $^1$H NMR are consistent with (E)-N-((6-chloro-7-methoxy-2-oxo-1,2-dihydroquinolin-3-yl)methylene)-2-methylpropane-2-sulfinamide (1.01 g, 2.96 mmol, 35.2% yield). $^1$H NMR (300 MHz, DMSO-d$_6$): δ ppm 12.21 (s, 1H), 8.74 (s, 1H), 8.59 (s, 1H), 8.08 (s, 1H), 6.97 (s, 1H), 3.94 (s, 3H), 1.19 (s, 9H). LCMS (Method 1): m/z 341 [M+H]$^+$.

Step-4: N-(1-(6-chloro-7-methoxy-2-oxo-1,2-dihydroquinolin-3-yl)ethyl)-2-methylpropane-2-sulfinamide

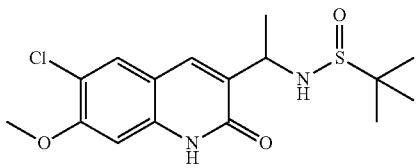 [SMILES: COc1cc2[nH]c(=O)c(C(C)NS(=O)C(C)(C)C)cc2cc1Cl]

N-((6-chloro-7-methoxy-2-oxo-1,2-dihydroquinolin-3-yl)methylene)-2-methylpropane-2-sulfinamide (265 mg, 0.778 mmol) was placed in a 50 mL round-bottom flask under an atmosphere of nitrogen. DCM (7 mL) was added, and the suspension was cooled on a dry ice/chloroform bath (to approx. −60° C.). Methylmagnesium bromide (MeMgBr) (3M in ether, 0.80 mL, 2.40 mmol) was added dropwise. The reaction mixture was stirred at −60° C. for several hours, then allowed to warm to room temperature overnight, resulting in an orange solution. Once LCMS indicated the reaction had gone to completion, the suspension was cooled on an ice bath and treated dropwise with water (3 mL). The resulting mixture was diluted with water (75 mL) and extracted with EtOAc (75 mL+20 mL). Silica gel was added and the EtOAc was evaporated under reduced pressure to provide a wet globular mass. Heptane and MeOH were added and the mixture was evaporated under reduced pressure to provide a powder. The material was purified by column chromatography on a Biotage® MPLC chromatography system (eluted with 0 to 4.2% MeOH in DCM, with isocratic elution when peaks eluted). The product fractions provided 152.7 mg of the title compound as a blue-green brittle foam. LCMS and $^1$H NMR are consistent with N-(1-(6-chloro-7-methoxy-2-oxo-1,2-dihydroquinolin-3-yl)ethyl)-2-methylpropane-2-sulfinamide (152.7 mg, 0.428 mmol, 55% yield). LCMS (Method 1): m/z 357 [M+H]$^+$.

Step-5: 3-(1-aminoethyl)-6-chloro-7-methoxyquinolin-2(1H)-one hydrochloride (II-3)

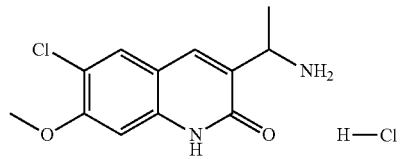 [SMILES: COc1cc2[nH]c(=O)c(C(C)N)cc2cc1Cl ; Cl]

A solution of N-(1-(6-chloro-7-methoxy-2-oxo-1,2-dihydroquinolin-3-yl)ethyl)-2-methyl propane-2-sulfinamide (149.6 mg, 0.419 mmol) in MeOH (3.8 mL) was cooled on an ice bath and treated dropwise with 4M HCl in 1,4-dioxane (2.2 mL). The reaction was stirred for 25 minutes, during which time a small amount of precipitate formed. The solvents were evaporated under reduced pressure at room temperature. The residue was triturated with 10 mL of ethyl ether, then collected on a Hirsch funnel, and washed with more ethyl ether to provide 115.6 mg of the title compound as a pale green solid. LCMS and $^1$H NMR are consistent with 3-(1-aminoethyl)-6-chloro-7-methoxyquinolin-2(1H)-one hydrochloride (115.6 mg, 0.400 mmol, 95% yield). $^1$H NMR (300 MHz, Methanol-d$_4$): δ ppm 7.95 (s, 1H), 7.77 (s, 1H), 6.97 (s, 1H), 4.51 (q, J=6.84 Hz, 1H), 3.98 (s, 3H), 1.68 (d, J=7.04 Hz, 3H). LCMS (Method 1): m/z 253 [M+H]$^+$.

Example 6—Intermediate II-4: (S)-3-(1-aminoethyl)-6-chloro-7-methoxyquinolin-2(1H)-one Scheme-3

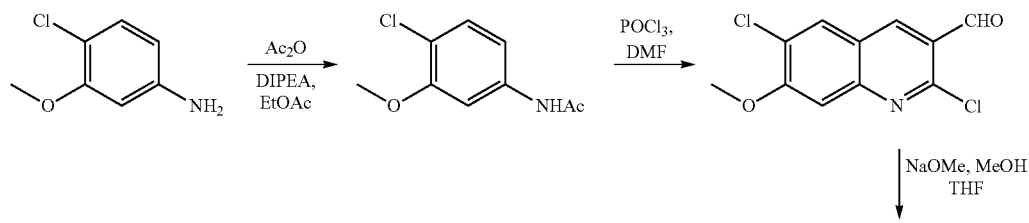

-continued

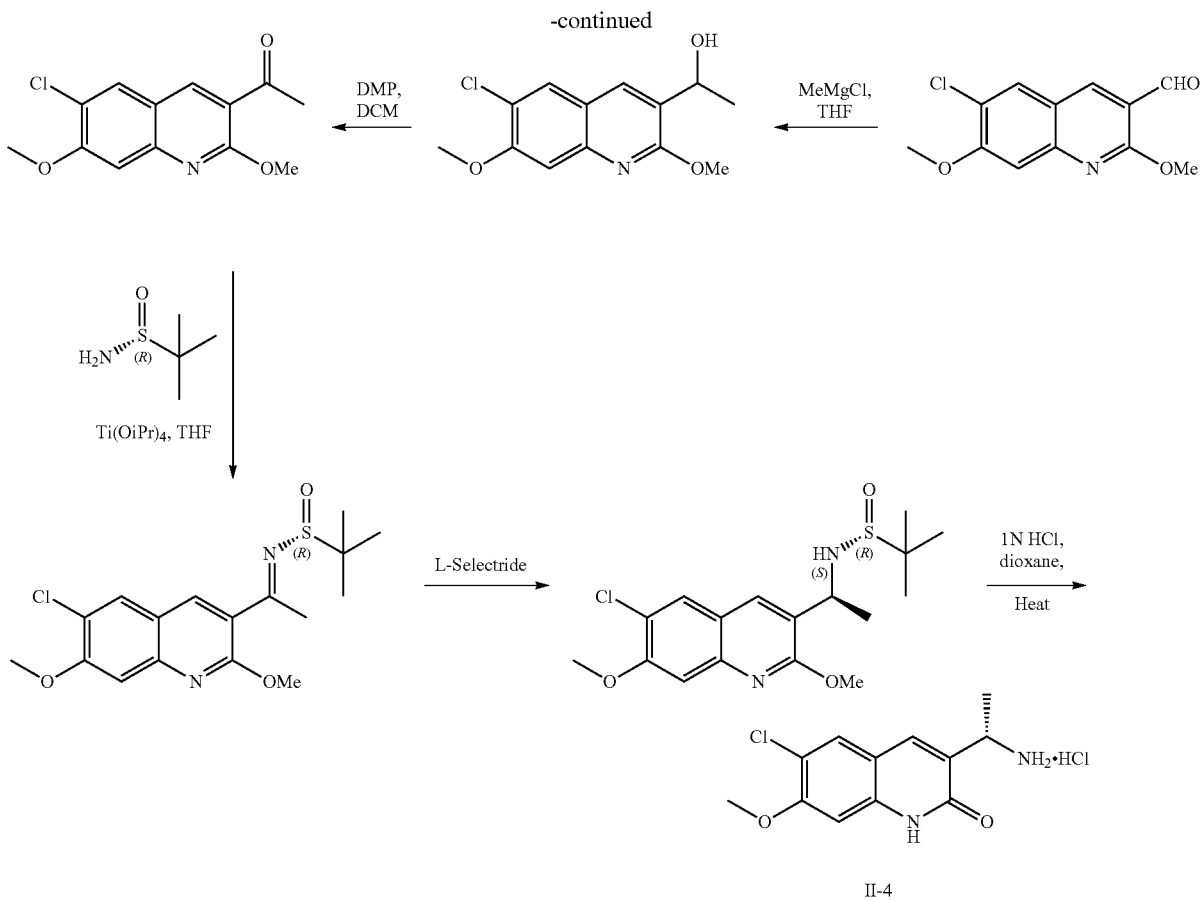

Step-1: N-(4-chloro-3-methoxyphenyl)acetamide

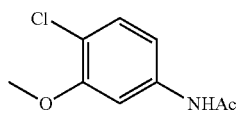

To a solution of 4-chloro-3-methoxyaniline (50 g, 317 mmol) and DIPEA (110 mL, 635 mmol) in CH$_2$Cl$_2$ (700 mL) was added acetic anhydride (36 mL, 381 mmol) drop wise at 0° C. and the reaction mixture was stirred at room temperature for 3 h. The reaction then was quenched with water (250 mL) and the organic layer was separated. The aqueous layer was extracted with CH$_2$Cl$_2$ (100 mL×3). The combined organic layers were dried (Na$_2$SO$_4$), concentrated and purified by flash chromatography with CH$_2$Cl$_2$/MeOH to give N-(4-chloro-3-methoxy phenyl)acetamide (71 g, quantitative yield) as a white solid.

Step-2: 2,6-Dichloro-7-methoxyquinoline-3-carbaldehyde

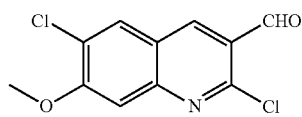 [SMILES: COc1cc2nc(Cl)c(C=O)cc2cc1Cl]

To POCl$_3$ (450 g, 274 mL, 2.95 mol) in a 2 L flask was added anhydrous DMF (83.5 g, 89 mL, 14 mol) drop wise. The reaction mixture was warmed up to room temperature and stirred for 20 min. After that N-(4-chloro-3-methoxyphenyl)acetamide (65 g, 327 mmol) was added portion wise at room temperature and the mixture was heated to 90° C. overnight. The reaction mixture was then cooled to room temperature and carefully quenched into aqueous NaHCO$_3$ solution. The precipitation obtained was filtered, washed with water (100 mL×3) and then dried in vacuum oven to give 60 g of title compound (73%).

Step-3: 6-Chloro-2,7-dimethoxyquinoline-3-carbaldehyde

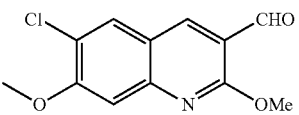 [SMILES: COc1cc2nc(OC)c(C=O)cc2cc1Cl]

To 2,6-dichloro-7-methoxyquinoline-3-carbaldehyde (40 g, 157 mmol) in MeOH (1 L) and THF (200 mL) was added NaOMe (16.9 g, 314 mmol) portion wise at room temperature. The reaction mixture was refluxed for 3 h. After cooling to room temperature, the reaction was quenched by addition of aqueous NH$_4$Cl solution (200 mL). The mixture was extracted with EtOAc (200 mL×3). The combined organic layers were dried (Na$_2$SO$_4$), concentrated and purified by flash chromatography with hexanes/EtOAc (3:1) to give the desired product (37.89 g, 96%) as a yellow solid.

Step-4: 1-(6-chloro-2,7-dimethoxyquinolin-3-yl)ethanol

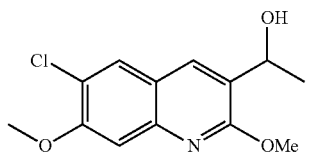 [SMILES: COc1cc2nc(OC)c(C(C)O)cc2cc1Cl]

To a solution of 6-chloro-2,7-dimethoxyquinoline-3-carbaldehyde (36.74 g, 151 mmol) in THF (1 L) at −78° C. was added a solution of MeMgCl in THF (3 M, 75.5 mL, 226 mmol) drop wise. The reaction was stirred at room temperature for 3 h and then quenched with aqueous NH$_4$Cl solution (250 mL). The organic layer was separated and the aqueous layer was extracted with EtOAc (100 mL×3). The combined organic layers were dried (Na$_2$SO$_4$), concentrated, and purified by silica gel chromatography with hexanes/EtOAc (3:1) to afford the title compound (38.06 g, 91%).

Step-5: 1-(6-chloro-2,7-dimethoxyquinolin-3-yl)ethanone

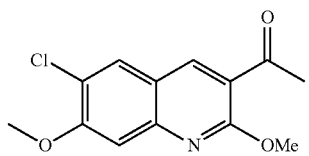 [SMILES: COc1cc2nc(OC)c(C(C)=O)cc2cc1Cl]

To 1-(6-chloro-2,7-dimethoxyquinolin-3-yl)ethanol (36.74 g, 137.6 mmol) in CH$_2$Cl$_2$ (1 L) at 0° C. was added DMP (70.0 g, 165.1 mmol) portion wise. The reaction was stirred at room temperature for 2 h, and then was quenched with an aqueous solution of NaHCO$_3$ and Na$_2$S$_2$O$_3$. After stirring for 15 min, both layers became clear. The organic layer was separated and the aqueous layer was extracted with CH$_2$Cl$_2$ (100 mL×2). The combined organic layers were dried (Na$_2$SO$_4$), concentrated and purified by silica gel chromatography with hexanes/EtOAc (4:1) to afford the title compound (30.02 g, 80%) as a white solid.

Step-6: (R,E)-N-(1-(6-chloro-2,7-dimethoxyquinolin-3-yl)ethylidene)-2-methylpropane-2-sulfinamide

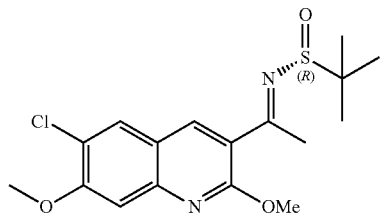

To 1-(6-chloro-2,7-dimethoxyquinolin-3-yl)ethanone (30.07 g, 113.5 mmol) in THF/toluene (100 mL/1 L) at room temperature was added (R)-2-methylpropane-2-sulfinamide (27.5 g, 227 mmol) and Ti(OiPr)$_4$ (97 mL, 340.5 mmol,). The reaction was refluxed with a Dean-Stark apparatus. After the reaction was refluxed for 4 h and 300 mL of solvent was removed, the reaction was cooled to room temperature. The solvent was removed under vacuum, and 200 mL of EtOAc was added to the residue, followed by 100 mL of saturated aqueous NaHCO$_3$ solution. After stirring for 10 min, the reaction mixture was passed through a pad of celite. The filtrate was extracted with EtOAc (200 mL×2), dried (Na$_2$SO$_4$), concentrated and purified by silica gel chromatography with hexanes/EtOAc (1:1) to give the title compound (34.28 g, 82%).

Step-7: (R)-N-((S)-1-(6-chloro-2,7-dimethoxyquinolin-3-yl)ethyl)-2-methylpropane-2-sulfinamide

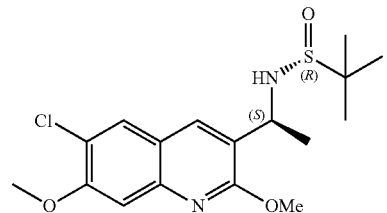

To (R,E)-N-(1-(6-chloro-2,7-dimethoxyquinolin-3-yl)ethylidene)-2-methylpropane-2-sulfinamide (34.28 g, 93.15 mmol) in THF (600 mL) at −78° C., was added 1 M L-selectride (121 mL, 121 mmol) in THF drop wise. The reaction mixture was warmed to room temperature and stirred for 3 h. The reaction was quenched with aqueous saturated NH$_4$Cl (300 mL) solution and then extracted with EtOAc (200 mL×2). The combined organic layers were dried (Na$_2$SO$_4$), concentrated and purified by silica gel chromatography with hexanes/EtOAc (1:1) to afford the title compound (29.27 g, 85%).

Step-8: (S)-3-(1-aminoethyl)-6-chloro-7-methoxyquinolin-2(1H)-one hydrochloride salt (II-7)

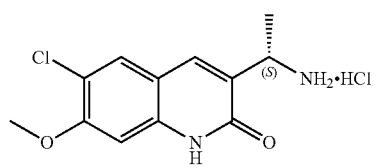

To (R)-N-((S)-1-(6-chloro-2,7-dimethoxyquinolin-3-yl)ethyl)-2-methylpropane-2-sulfinamide (30.35 g, 82 mmol) in dioxane (250 mL) was added 2 N HCl (250 mL) at rt. The reaction mixture was refluxed for 3 h, cooled to room temperature and the solvent was removed under vacuum. The crude residue obtained was dried under vacuum to give a crude product, which was further purified by trituration (CH$_2$Cl$_2$/MeOH/hexane) to obtain pure title compound II-4 (17.65 g, 75%) as a white solid. $^1$H NMR (300 MHz, DMSO-d6): δ 12.18 (s, 1H), 8.24 (br, s, 3H), 7.99 (s, 1H), 7.86 (s, 1H), 7.02 (s, 1H), 4.41 (m, 1H), 3.91 (s, 3H), 1.52 (d, J=6.87 Hz, 3H). LCMS (Method 3): Rt 3.48 min, m/z 253.1 [M+H]$^+$.

Example 7—Intermediate II-5: (R)-3-(1-amino-ethyl)-6-chloro-7-methoxyquinolin-2(1H)-one

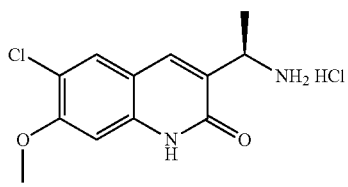

The title compound II-5 was prepared in the same procedure described for II-4, except using (S)-2-methylpropane-2-sulfinamide in Step-6 (Scheme-3). $^1$H NMR (300 MHz, Methanol-d$_4$): δ ppm 7.92 (s, 1H), 7.75 (s, 1H), 6.95 (s, 1H), 4.48 (q, J=6.84 Hz, 1H), 3.96 (s, 3H), 1.65 (d, J=6.74 Hz, 3H). LCMS: m/z 253 [M+H]$^+$.

Example 8—Intermediate II-6: 3-(1-aminoethyl)-6-chloro-7-(pyridin-2-ylmethoxy)quinolin-2(1H)-one

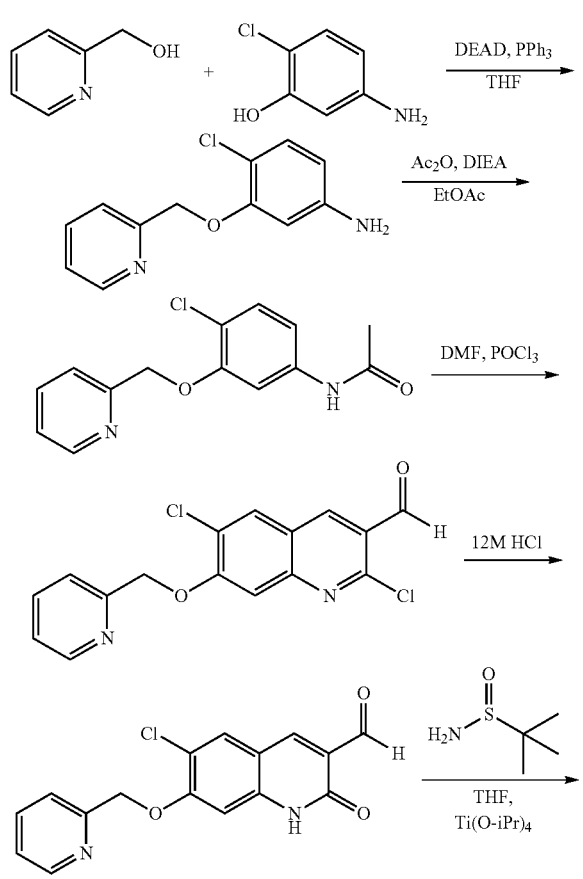

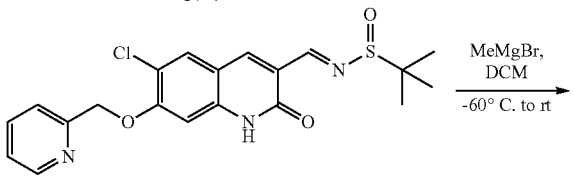

IV-4

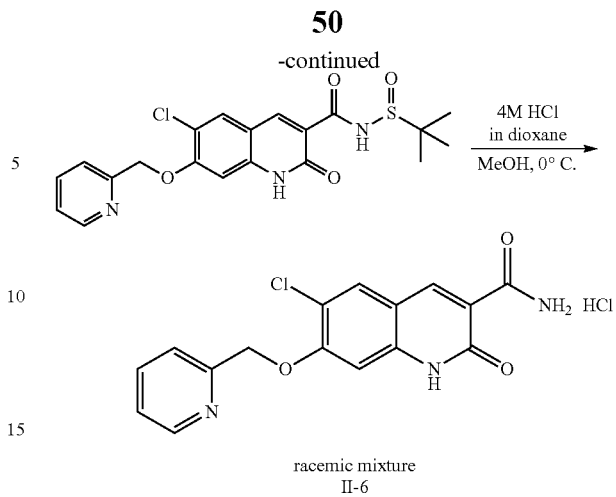

racemic mixture
II-6

Step-1: 4-chloro-3-(pyridin-2-ylmethoxy)aniline

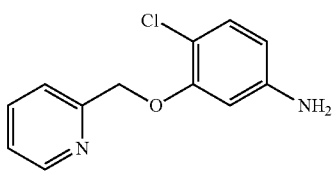 [SMILES: Nc1ccc(Cl)c(OCc2ccccn2)c1]

A solution of 5-amino-2-chlorophenol (2.00 g, 13.93 mmol pyridin-2-ylmethanol (1.4 mL, 14.51 mmol), and triphenylphosphine (4.30 g, 16.39 mmol) in THF (250 mL) was placed under an atmosphere of nitrogen and treated with DEAD (2.6 mL, 16.42 mmol) The solution was stirred at room temperature overnight. Once LCMS indicated the reaction had gone to completion, the solution was treated with silica gel and evaporated under reduced pressure. The material was purified by column chromatography on a Biotage® MPLC chromatography system (using a 340 g silica gel column, eluted with 0 to 100% EtOAc in hexanes, then 2.3% MeOH in EtOAc) to provide the title compound as a light brown solid. LCMS and $^1$H NMR are consistent with 4-chloro-3-(pyridin-2-ylmethoxy)aniline (2.29 g, 9.76 mmol, 70.0% yield) with residual triphenylphosphine oxide. The crude was used in the next step without further purification. $^1$H NMR (300 MHz, DMSO-d$_6$): δ ppm 8.62-8.55 (m, 1H), 7.86 (ddd, J=7.77, 7.77, 1.76 Hz, 1H), 7.52 (d, J=7.92 Hz, 1H), 7.35 (dd, J=6.89, 5.42 Hz, 1H), 7.02 (d, J=8.50 Hz, 1H), 6.37 (d, J=2.35 Hz, 1H), 6.15 (dd, J=8.50, 2.35 Hz, 1H), 5.28 (s, 2H), 5.14 (s, 2H). LCMS (Method 1): m/z 235 [M+H]$^+$.

Step-2: N-(4-chloro-3-(pyridin-2-ylmethoxy)phenyl)acetamide

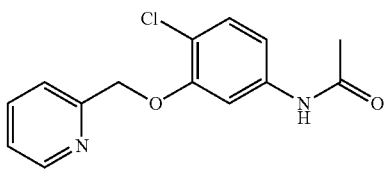 [SMILES: CC(=O)Nc1ccc(Cl)c(OCc2ccccn2)c1]

A solution of 4-chloro-3-(pyridin-2-ylmethoxy)aniline (5.22 g, 22.24 mmol) and DIEA (4.30 mL, 24.62 mmol) in EtOAc (125 mL) was treated with Ac$_2$O (2.30 mL, 24.38 mmol) The solution was stirred at room temperature overnight, after which a thick white precipitate formed. EtOAc (300 mL) was added and the mixture was shaken until most of the precipitate dissolved. The organic layer was then washed with water and brine (125 mL each), dried (Na$_2$SO$_4$) and filtered. Silica gel was added, and the mixture was evaporated under reduced pressure. The residue was purified by column chromatography on a Biotage® MPLC chromatography system (using a 100 g silica gel column, eluted with 0 to 5% MeOH in DCM) to provide 3.23 g of the title compound as a white solid. LCMS and $^1$H NMR are consistent with N-(4-chloro-3-(pyridin-2-ylmethoxy)phenyl)acetamide (3.23 g, 11.67 mmol, 52.5% yield)$^1$H NMR (300 MHz, DMSO-d$_6$): δ ppm 10.06 (s, 1H), 8.62-8.56 (m, 1H), 7.87 (ddd, J=7.80, 7.80, 1.80 Hz, 1H), 7.53 (d, J=7.62 Hz, 1H), 7.49 (d, J=2.05 Hz, 1H), 7.40-7.33 (m, 2H), 7.22 (dd, J=8.65, 2.20 Hz, 1H), 5.21 (s, 2H), 2.02 (s, 3H). LCMS (Method 1): m/z 277 [M+H]$^+$.

Step-3: 2,6-dichloro-7-(pyridin-2-ylmethoxy)quinoline-3-carbaldehyde

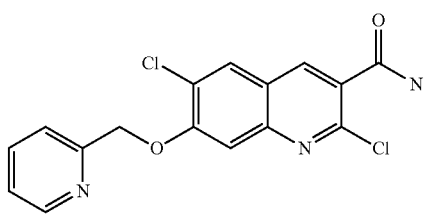 [SMILES: NC(=O)c1cc2cc(Cl)c(OCc3ccccn3)cc2nc1Cl]

A tube was capped with a septum and placed under an atmosphere of nitrogen. DMF (2.9 mL, 37.5 mmol) was added by syringe and then cooled on an ice bath. POCl$_3$ (11.4 mL, 122 mmol) was added dropwise by syringe (over 20 minutes). The solution was allowed to warm to room temperature (over 15 minutes) and the septum was removed. The mixture was treated with N-(4-chloro-3-(pyridin-2-ylmethoxy)phenyl)acetamide (3.16 g, 11.42 mmol). The tube was again sealed and the solution was stirred at 80° C. overnight. The mixture was then pipetted onto ice, resulting in the formation of a yellow precipitate. The precipitate was collected on a Buchner funnel, washed with water (500 mL), and dried to provide 2.88 g of the title compound as a pale yellow solid. LCMS and $^1$H NMR are consistent with 2,6-dichloro-7-(pyridin-2-ylmethoxy)quinoline-3-carbaldehyde (2.88 g, 8.64 mmol, 76% yield). $^1$H NMR (300 MHz, DMSO-d$_6$): δ ppm 10.34 (s, 1H), 8.89 (s, 1H), 8.66 (br d, J=4.10 Hz, 1H), 8.52 (s, 1H), 8.01-7.92 (m, 1H), 7.75 (s, 1H), 7.69 (br d, J=7.62 Hz, 1H), 7.50-7.41 (m, 1H), 5.55 (s, 2H). LCMS (Method 1): m/z 333 [M+H]$^+$.

Step-4: 6-chloro-2-oxo-7-(pyridin-2-ylmethoxy)-1,2-dihydroquinoline-3-carbaldehyde IV-4

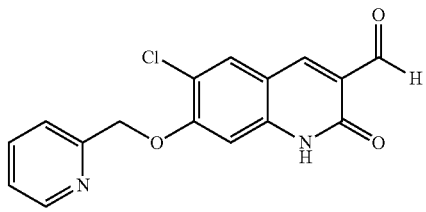 [SMILES: O=Cc1cc2cc(Cl)c(OCc3ccccn3)cc2[nH]c1=O]

A solution of 2,6-dichloro-7-(pyridin-2-ylmethoxy)quinoline-3-carbaldehyde (2.88 g, 8.64 mmol) in concentrated HCl (81 mL) was stirred at reflux (bath temperature 100° C.) for one day, during which time the solution turned orange. The solution was diluted with water (900 mL), resulting in the formation of a yellow precipitate. The precipitate was collected on a Buchner funnel, washed with water (750 mL), and dried under vacuum at 60° C. to provide 2.27 g of the title compound as a yellow solid. LCMS and $^1$H NMR are consistent with 6-chloro-2-oxo-7-(pyridin-2-ylmethoxy)-1,2-dihydroquinoline-3-carbaldehyde IV-4 (2.27 g, 7.21 mmol, 83% yield). $^1$H NMR (300 MHz, DMSO-d$_6$): δ ppm 12.20 (s, 1H), 10.16-10.19 (m, 1H), 8.64-8.60 (m, 1H), 8.44 (s, 1H), 8.14 (s, 1H), 7.90 (ddd, J=7.60, 7.60, 1.80 Hz, 1H), 7.57 (d, J=7.62 Hz, 1H), 7.43-7.36 (m, 1H), 7.05 (s, 1H), 5.37 (s, 2H). LCMS (Method 1): m/z 315 [M+H]$^+$.

Step-5: (E)-N-((6-chloro-2-oxo-7-(pyridin-2-ylmethoxy)-1,2-dihydroquinolin-3-yl)methylene)-2-methylpropane-2-sulfinamide

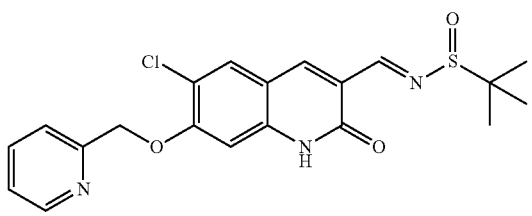 [SMILES: CC(C)(C)S(=O)/N=C/c1cc2cc(Cl)c(OCc3ccccn3)cc2[nH]c1=O]

A mixture of 6-chloro-2-oxo-7-(pyridin-2-ylmethoxy)-1,2-dihydroquinoline-3-carbaldehyde (2.27 g, 7.21 mmol) and 2-methylpropane-2-sulfinamide (1.05 g, 8.66 mmol) was placed in a 25 mL round bottom flask under an atmosphere of nitrogen. THF (9 mL) and titanium (IV) isopropoxide (Ti(O$^i$Pr)$_4$) (4.3 mL, 14.68 mmol) were added by syringe and the suspension was stirred at room temperature for one day. Once LCMS indicated the reaction had gone to completion, the material was triturated with EtOAc (400 mL), then filtered through Celite® 545, and the filter cake was washed with EtOAc (100 mL). The filter cake was sonicated in EtOAc (400 mL) for fifteen minutes and then filtered on a Buchner funnel. The two filtrates were combined and washed with brine (250 mL). The aqueous layer was back-extracted with EtOAc (200 mL+100 mL). The three combined organic layers were dried (Na$_2$SO$_4$), filtered, and evaporated under reduced pressure to provide 1.44 g of the title compound as a yellow solid. LCMS and $^1$H NMR are consistent with (E)-N-((6-chloro-2-oxo-7-(pyridin-2-ylmethoxy)-1,2-dihydroquinolin-3-yl)methylene)-2-methylpropane-2-sulfinamide (1.44 g, 3.45 mmol, 47.8% yield). $^1$H NMR (300 MHz, DMSO-d$_6$): δ ppm 12.20 (s, 1H), 8.74 (s, 1H), 8.62 (d, J=4.10 Hz, 1H), 8.60 (s, 1H), 8.13 (s, 1H), 7.90 (ddd, J=7.80, 7.80, 1.80 Hz, 1H), 7.58 (d, J=7.92 Hz, 1H), 7.40 (dd, J=7.18, 4.54 Hz, 1H), 7.06 (s, 1H), 5.36 (s, 2H), 1.19 (s, 9H). LCMS (Method 1): m/z 418 [M+H]$^+$.

Step-6: N-(1-(6-chloro-2-oxo-7-(pyridin-2-yl-methoxy)-1,2-dihydroquinolin-3-yl)ethyl)-2-methyl-propane-2-sulfinamide

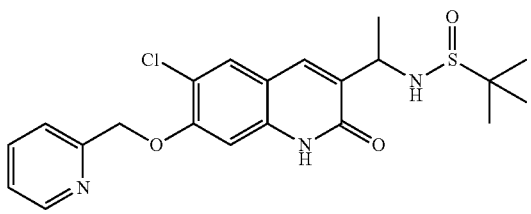 [SMILES: CC(NS(=O)C(C)(C)C)c1cc2cc(Cl)c(OCc3ccccn3)cc2[nH]c1=O]

(E)-N-((6-chloro-2-oxo-7-(pyridin-2-ylmethoxy)-1,2-dihydroquinolin-3-yl)methylene)-2-methyl propane-2-sulfinamide (1.44 g, 3.45 mmol) was placed in a 250 mL round-bottom flask under an atmosphere of nitrogen. DCM (27 mL) was added and the suspension was cooled on a dry ice/chloroform bath (to approx. −60° C.). Methylmagnesium bromide (MeMgBr) (3M in ether, 3.50 mL, 10.50 mmol) was added dropwise. The cold bath was allowed to warm to room temperature overnight resulting in an orange suspension. Once LCMS indicated the reaction had gone to completion, the suspension was cooled on an ice bath and treated dropwise with water (10 mL) resulting in emulsification. The emulsion was diluted with EtOAc (400 mL) and washed with water (400 mL). Silica gel was added to the organic layer and the solvent was evaporated under reduced pressure. The material was purified by column chromatography on a Biotage® MPLC chromatography system (eluted with 0 to 6% MeOH in DCM with isocratic elution when peaks eluted) to provide 1.17 g of the title compound as a yellow brittle foam. LCMS and $^1$H NMR are consistent with N-(1-(6-chloro-2-oxo-7-(pyridin-2-ylmethoxy)-1,2-dihydroquinolin-3-yl)ethyl)-2-methylpropane-2-sulfinamide (1.17 g, 2.70 mmol, 78% yield). NMR indicated a mixture of diastereomers. LCMS (Method 1): m/z 434 [M+H]$^+$.

Step-7: 3-(1-aminoethyl)-6-chloro-7-(pyridin-2-ylmethoxy)quinolin-2(1H)-one hydrochloride (II-6)

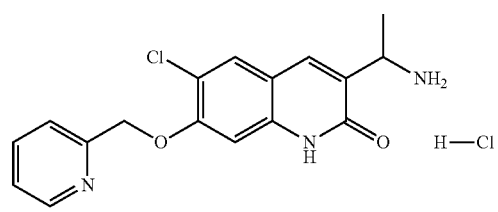

A solution of N-(1-(6-chloro-2-oxo-7-(pyridin-2-ylmethoxy)-1,2-dihydroquinolin-3-yl)ethyl)-2-methylpropane-2-sulfinamide (167.3 mg, 0.386 mmol) in MeOH (3.5 mL) was cooled on an ice bath and treated dropwise with 4M HCl in 1,4-dioxane (2 mL). The reaction was stirred for 20 minutes and within five minutes a precipitate began to form. The solvents were evaporated under reduced pressure at room temperature. The residue was triturated with 10 mL of ethyl ether, collected on a Hirsch funnel and washed with more ethyl ether to provide 145.8 mg of the title compound as a pale yellow solid. LCMS and $^1$H NMR are consistent with 3-(1-aminoethyl)-6-chloro-7-(pyridin-2-ylmethoxy)quinolin-2(1H)-one hydrochloride (145.8 mg, 0.398 mmol, 103% yield). $^1$H NMR (300 MHz, Methanol-d$_4$): δ ppm 8.95-8.91 (m, 1H), 8.68 (ddd, J=7.90, 7.90, 1.50 Hz, 1H), 8.29 (d, J=7.62 Hz, 1H), 8.11-8.04 (m, 1H), 8.00 (s, 1H), 7.90 (s, 1H), 7.17 (s, 1H), 5.66 (s, 2H), 4.53 (q, J=6.84 Hz, 1H), 1.69 (d, J=6.74 Hz, 3H). LCMS (Method 1): m/z 352 [M+Na]$^+$.

Example 9—Intermediate II-7: (S)-3-(1-amino-ethyl)-6-chloro-7-(pyridin-2-ylmethoxy)quinolin-2(1H)-one

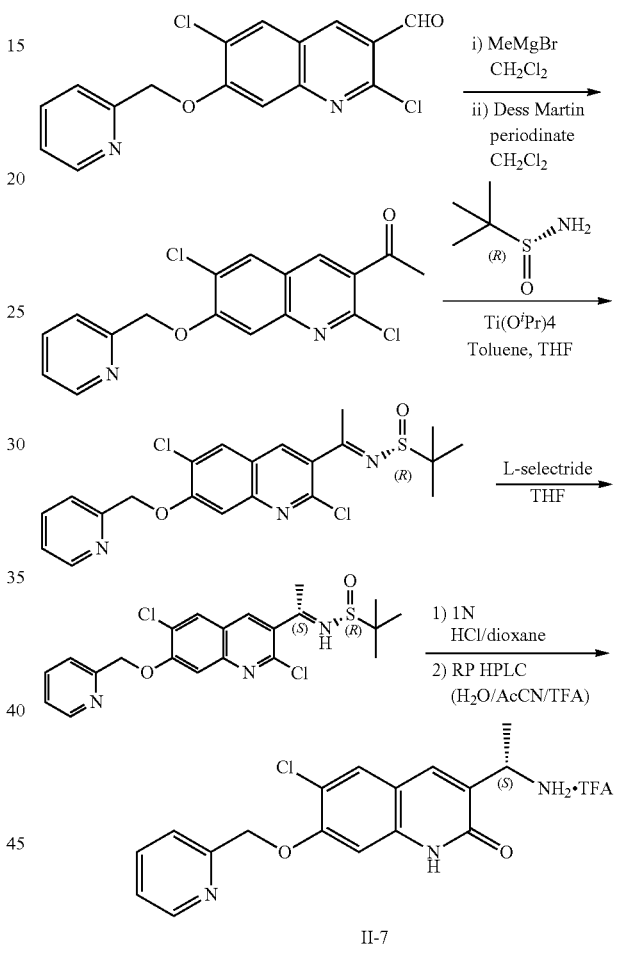

Step-1: 1-(2,6-Dichloro-7-(pyridin-2-ylmethoxy)quinolin-3-yl)ethanone

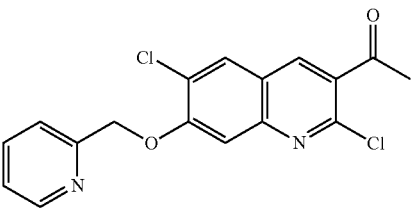 [SMILES: CC(=O)c1cc2cc(Cl)c(OCc3ccccn3)cc2nc1Cl]

To a solution of 2,6-dichloro-7-(pyridin-2-ylmethoxy)quinoline-3-carbaldehyde (1.0 g, 3.0 mmol) (prepared in the same procedure described for step-1-3 shown in Scheme-4) in CH$_2$Cl$_2$ (40 mL) was added dropwise methyl magnesium bromide (MeMgBr) (3 M solution in diethyl ether, 1.5 mL, 4.50 mmol) at 0° C. The resulting mixture was then stirred at ambient temperature for 1.5 hours. Upon completion of reaction, the mixture was slowly quenched with water (3 mL) and extracted with CH$_2$Cl$_2$ (50 mL). The organic layer was separated and dried over anhydrous Na$_2$SO$_4$. The solvents were evaporated to dryness. The resulting residue was dissolved in CH$_2$Cl$_2$ (25 mL) and treated with Dess-Martin Periodinate (2.54 g, 6.00 mmol). The mixture was stirred at ambient temperature overnight. The mixture was then quenched with an aqueous co-solution of 20% NaHCO$_3$ and 20% Na$_2$S$_2$O$_3$ (10 mL) and stirred for 5 minutes at room temperature. The solution was extracted with CH$_2$Cl$_2$ (40 mL), dried over anhydrous Na$_2$SO$_4$, filtered and evaporated. The resulting residue was purified by column chromatography on an ISCO® chromatography system (SiO$_2$ column: eluted with CH$_2$Cl$_2$/MeOH 0 to 10%) to afford the title compound (800 mg, 79%).

Step-2: (R,E)-N-(1-(2,6-dichloro-7-(pyridin-2-yl-methoxy)quinolin-3-yl)ethylidene)-2-methylpropane-2-sulfinamide

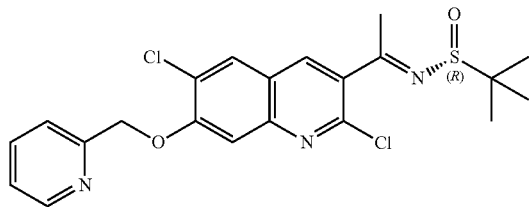

To a mixture of 1-(2,6-dichloro-7-(pyridin-2-ylmethoxy) quinolin-3-yl)ethanone (2.18 g, 6.56 mmol) and (R)-2-methylpropane-2-sulfinamide (1.19 g, 9.84 mmol) in THF: Toluene (40 mL:180 mL), was added titanium (IV) isopropoxide (Ti(O$^i$Pr)$_4$) (3.96 mL, 13.30 mmol). The resulting mixture was refluxed with a Dean-Stark apparatus for 7 hours. The mixture was then cooled to room temperature, quenched with water, and diluted with EtOAc (300 mL). The organic layer was washed with water (100 mL), dried over anhydrous Na$_2$SO$_4$, filtered and evaporated to dryness. The resulting residue was purified by column chromatography on an ISCO® chromatography system (SiO$_2$ column: eluted with Hex/EtOAc 0 to 100%) to afford the title compound as yellow solid (1.4 g, 50% yield). The starting material ketone was also recovered (250 mg, 11% yield).

Step-3: (R)-N-((S)-1-(2,6-dichloro-7-(pyridin-2-ylmethoxy)quinolin-3-yl)ethyl)-2-methyl propane-2-sulfinamide

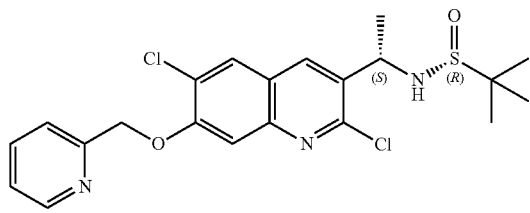

To a solution of (R,E)-N-(1-(2,6-dichloro-7-(pyridin-2-ylmethoxy)quinolin-3-yl)ethylidene)-2-methyl propane-2-sulfinamide (900 mg, 1.99 mmol) in THF (25 mL) at −40 to −50° C. was added L-selectride (1M in THF, 1.98 mL, 2.59 mmol) dropwise. The resulting mixture was stirred at −40 to −50° C. for 2 hours. Upon completion of reaction, the mixture was quenched with ice at −50° C., extracted with EtOAc (100 mL), dried, and evaporated. The resulting residue was purified by column chromatography on an ISCO® chromatography system (SiO$_2$ column: Hex/EtOAc 0 to 100%) followed by trituration with hexanes-methylene chloride to afford the title compound (266 mg, 30% yield).

Step-4: (S)-3-(1-Aminoethyl)-6-chloro-7-(pyridin-2-ylmethoxy)quinolin-2(1H)-one TFA salt (II-7)

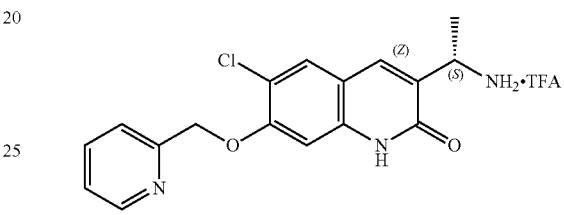

To a mixture of (R)-N-((S)-1-(2,6-dichloro-7-(pyridin-2-ylmethoxy)quinolin-3-yl)ethyl)-2-methylpropane-2-sulfinamide (1.1 g, 2.43 mmol) in 1,4-dioxane (6.6 mL), was added aqueous 1N HCl (6.6 mL) at room temperature. The resulting mixture was heated to 120° C. overnight. After TLC and MS showed completion of reaction, the solvents were removed on a rotary evaporator and lyophilized to provide yellow solid. The crude solid was purified by reverse phase chromatography on an ISCO® chromatography system (C18 column: eluted with H$_2$O/MeCN/0.1% CF$_3$CO$_2$H 0 to 100%) and the fractions were monitored by LCMS. The pure fractions were combined and lyophilized to afford the title compound II-7 (920 mg, 86% yield) as the TFA salt. $^1$H NMR (300 MHz, DMSO-d$_6$): δ 12.17 (br s, 1H), 8.62 (d, J=4.95 Hz, 1H), 8.09 (br s, 2H), 7.96-7.85 (m, 3H), 7.59 (d, J=7.9 Hz, 1H), 7.42-7.37 (m, 1H), 7.08 (d, J=2.5 Hz, 1H), 5.33 (s, 2H), 4.39-4.38 (m, 1H), 1.51 (d, J=6.8 Hz, 3H). LCMS (method 3): Rt 3.3 min, m/z 329.1 [M+H]$^+$.

Example 10—Intermediate VI-1: 4-((6-chloro-7-hydroxy-2-oxo-1,2-dihydroquinolin-3-yl)methyl-amino)-2-methoxybenzonitrile (I-57)

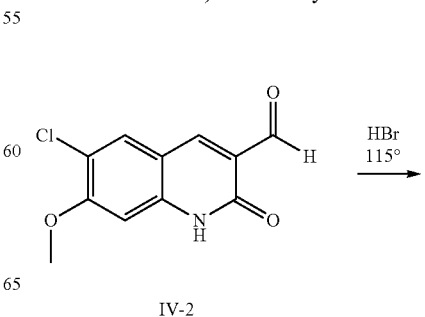

IV-2

Step 1: 6-chloro-7-hydroxy-2-oxo-1,2-dihydroquinoline-3-carbaldehyde (IV-3)

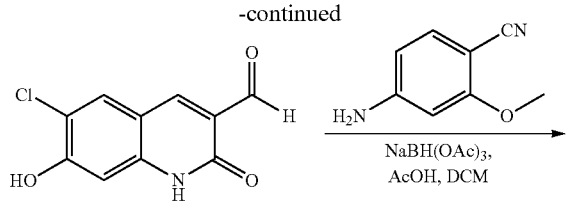

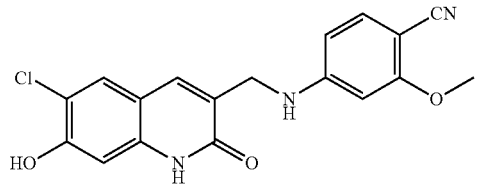

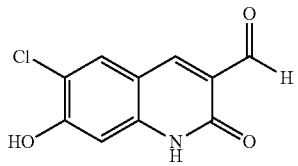 [SMILES: O=Cc1cc2cc(Cl)c(O)cc2[nH]c1=O]

A suspension of damp 6-chloro-7-methoxy-2-oxo-1,2-dihydroquinoline-3-carbaldehyde (see Step 2, II-3 for preparation; maximum 39.0 mmol) in 48% hydrobromic acid (210 ml) was heated on a 110° C. bath. After an hour the bath temperature was raised to 115° C., and after another ~30 minutes the suspension went into solution. The solution was heated at 115° C. for four days, during which time a small quantity of brown precipitate formed. The mixture was poured into water and diluted to 2 L, resulting in more precipitation. The precipitate was collected on a Buchner funnel, washed with water (800 mL), and dried in a vacuum oven to provide 6-chloro-7-hydroxy-2-oxo-1,2-dihydroquinoline-3-carbaldehyde IV-3 (6.47 g, 28.9 mmol, 74.2% yield) as a brown solid, impure but suitable for use. $^1$H NMR (300 MHz, DMSO-$d_6$): δ ppm 12.11 (s, 1H), 11.67 (s, 1H), 10.18-10.13 (m, 1H), 8.38 (s, 1H), 8.01 (s, 1H), 6.93 (s, 1H). LCMS (Method 1): Rt 1.74 min., m/z 224.0 [M+H]$^+$.

Step 2: 4-((6-chloro-7-hydroxy-2-oxo-1,2-dihydroquinolin-3-yl)methylamino)-2-methoxy benzonitrile (VI-1, I-57).

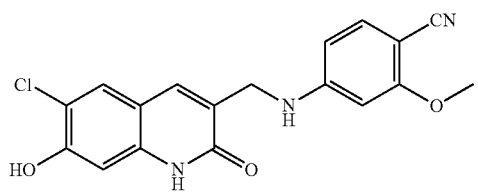 [SMILES: COc1cc(NCc2cc3cc(Cl)c(O)cc3[nH]c2=O)ccc1C#N]

A suspension of 6-chloro-7-hydroxy-2-oxo-1,2-dihydroquinoline-3-carbaldehyde (58.0 mg, 0.259 mmol) and 4-amino-2-methoxybenzonitrile (48.0 mg, 0.324 mmol) in DCM (4.0 mL) was treated with acetic acid (0.07 mL, 1.223 mmol) and stirred 10 minutes. Sodium triacetoxyborohydride (84.0 mg, 0.396 mmol) was added. The mixture was stirred at room temperature overnight. The mixture was diluted with EtOAc (50 mL), washed with water (2×50 mL) and brine (50 mL), dried (Na$_2$SO$_4$), filtered, and evaporated under reduced pressure. The residue was dissolved in methanol, treated with silica gel, and evaporated. The material was chromatographed by Biotage MPLC (10 g silica gel column) with 20 to 100% EtOAc in hexanes to provide the title compound I-57 (18.6 mg, 0.052 mmol, 20.2% yield) as a peach-coloured solid. $^1$H NMR (300 MHz, DMSO-$d_6$): δ ppm 11.82 (s, 1H), 10.89 (s, 1H), 7.70 (s, 1H), 7.63 (s, 1H), 7.28 (d, J=8.50 Hz, 1H), 7.12 (dd, J=6.00, 6.00 Hz, 1H), 6.91 (s, 1H), 6.32 (d, J=1.76 Hz, 1H), 6.22 (dd, J=8.60, 1.60 Hz, 1H), 4.17 (d, J=5.60 Hz, 2H), 3.78 (s, 3H). LCMS (Method 4): Rt 1.17 min., m/z 356.1 [M+H]$^+$.

Example 11—Intermediate IV-5 & IV-6: 6-chloro-3-(hydroxymethyl)-8-methoxyquinolin-2(1H)-one (IV-5) and 6-chloro-8-methoxy-2-oxo-1,2-dihydroquinoline-3-carbaldehyde (IV-6)

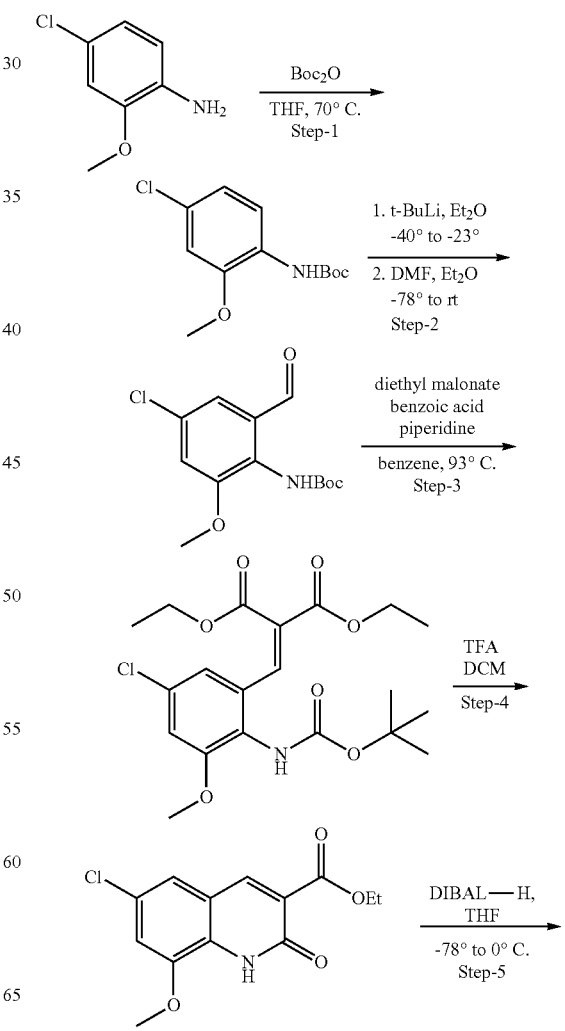

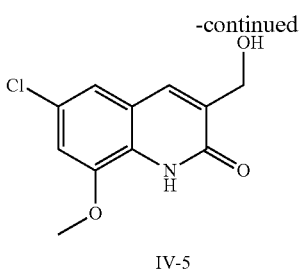

IV-5

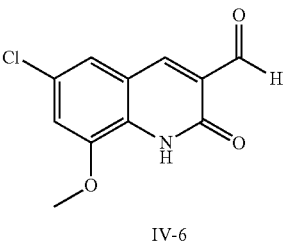

IV-6

Step 1: tert-butyl
4-chloro-2-methoxyphenylcarbamate

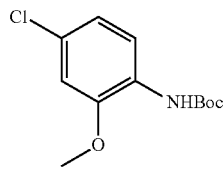 [SMILES: COc1cc(Cl)ccc1NC(=O)OC(C)(C)C]

A solution of 4-chloro-2-methoxyaniline (4.93 g, 31.3 mmol) in THF (70 ml) was treated with BOC-anhydride (11.00 ml, 47.4 mmol) and heated at 700 overnight. LCMS showed that most of starting materials were converted to product. The solution was treated with silica gel and evaporated under reduced pressure. The material was divided into two batches, each of which was chromatographed by Biotage MPLC (50 g silica gel column, 0 to 1% EtOAc in hexanes). Like fractions from the two columns were combined and evaporated under reduced pressure to provide a clear colorless liquid. Heptane (~80 mL) was added, then evaporated under reduced pressure to provide a clear, very viscous liquid. LCMS and NMR are consistent with tert-butyl 4-chloro-2-methoxyphenylcarbamate (7.66 g, 29.7 mmol, 95% yield). $^1$H NMR (300 MHz, CHLOROFORM-d): δ ppm 8.08-7.96 (m, 1H), 7.01 (br s, 1H), 6.92 (dd, J=8.65, 2.20 Hz, 1H), 6.83 (d, J=2.34 Hz, 1H), 3.87 (s, 3H), 1.53 (s, 9H). LCMS: m/z 202 (loss oft-Bu).

Step 2: tert-butyl
4-chloro-2-formyl-6-methoxyphenylcarbamate

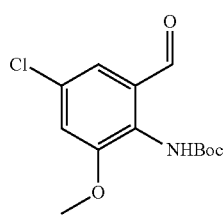 [SMILES: COc1cc(Cl)cc(C=O)c1NC(=O)OC(C)(C)C]

Tert-butyl 4-chloro-2-methoxyphenylcarbamate (6.12 g, 23.75 mmol) was dissolved in 2 mL ether and transferred to a 250 mL oven-dried 3-necked round bottom flask & magnetic stir bar; the original flask was successively rinsed with two more 2 mL aliquots of ether, each of which was added to the 3-necked flask. The apparatus was fitted with an oven-dried addition funnel, then flushed with nitrogen 20 minutes. Diethyl ether (30 mL) was added by syringe. The solution was cooled on a dry ice/acetonitrile bath (approximately −40° C.). Tert-butyllithium (1.7 M in pentane, 31 ml, 52.7 mmol) was transferred to the addition funnel by cannula, then added to the solution dropwise (~10 minutes). The solution became pale yellow during the addition. The dry ice/acetonitrile bath was replaced with a dry ice/CCl4 bath (approximately −22° C.) and the solution was stirred at that temperature 3.5 hours, during which time it soon became cloudy with a fine white precipitate. The bath was replaced with a dry ice/acetone bath (approximately −78° C.). The mixture was stirred 10 minutes, then a solution of DMF (3.40 ml, 43.9 mmol) in diethyl ether (32 mL) was added dropwise by syringe (30 minutes), during which time the suspension turned progressively brown. The dry ice was removed from the bath and the acetone was allowed to warm overnight, resulting in a red solution (the solids went into solution at about −25° C.). The reaction was quenched with water (40 mL), resulting in formation of a precipitate. More water (40 mL) was added, and most of the precipitate went into solution. The organic phase was removed and washed with brine (120 mL). The organic extract was dried (MgSO4), filtered, and evaporated to provide a reddish oil. The material was dissolved in hexanes-EtOAc and chromatographed by Biotage MPLC (100 g silica gel column, 2 to 8% EtOAc in hexanes, with isocratic elution when peaks came off) to provided 2.82 g clear oil. LCMS and 1H NMR are consistent with tert-butyl 4-chloro-2-formyl-6-methoxyphenylcarbamate (2.82 g, 9.87 mmol, 42% yield). 1H NMR (300 MHz, DMSO-d6): δ ppm 9.88 (s, 1H), 8.91 (s, 1H), 7.42 (d, J=2.35 Hz, 1H), 7.26 (d, J=2.35 Hz, 1H), 3.87 (s, 3H), 1.42 (s, 9H). LCMS: m/z 230 (loss of tBu).

Step 3: diethyl 2-(2-(tert-butoxycarbonylamino)-5-chloro-3-methoxybenzylidene)malonate

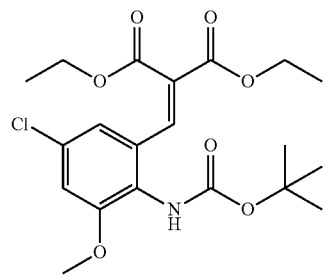 [SMILES: CCOC(=O)C(=Cc1cc(Cl)cc(OC)c1NC(=O)OC(C)(C)C)C(=O)OCC]

A solution of tert-butyl 4-chloro-2-formyl-6-methoxyphenylcarbamate (2.82 g, 9.87 mmol) in benzene (70 ml) in a 125 mL flask was treated with diethyl malonate (1.51 mL, 9.90 mmol), piperidine (106 μL, 1.071 mmol), and benzoic acid (113.7 mg, 0.931 mmol). The solution was heated at 89° C. (bath temperature) overnight with azeotropic distillation of water by use of a Claisen connecting tube. The solvent was evaporated under reduced pressure. The residue was dissolved in EtOAc (100 mL), washed with water (100 mL), dried (MgSO4), filtered, treated with silica gel, and evaporated under reduced pressure. The material was chromatographed by Biotage MPLC (100 g silica gel column, 0 to 15% EtOAc in hexanes, with isocratic elution at 14% EtOAc) to provide an oil. LCMS and $^1$H NMR are consistent with the title compound, diethyl 2-(2-(tert-butoxycarbonylamino)-5-chloro-3-methoxybenzylidene) malonate (3.29 g, 7.69 mmol, 78% yield). $^1$H NMR (300 MHz, DMSO-d6): δ ppm 7.66 (s, 1H), 7.26 (d, J=2.05 Hz, 1H), 6.93 (d, J=2.05 Hz, 1H), 4.17-4.31 (m, 5H), 3.83 (s, 3H), 1.39 (br s, 9H), 1.26-1.14 (m, 6H). LCMS: m/z 428 [M+H]$^+$.

Step 4: ethyl 6-chloro-8-methoxy-2-oxo-1,2-dihydroquinoline-3-carboxylate

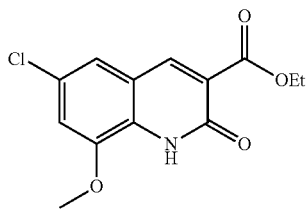 [SMILES: CCOC(=O)c1cc2cc(Cl)cc(OC)c2[nH]c1=O]

A stirred solution of diethyl 2-(2-(tert-butoxycarbonylamino)-5-chloro-3-methoxy benzylidene)malonate (3.2876 g, 7.68 mmol) in DCM (36 ml) was treated with TFA (36 ml). By 5 minutes after the addition, evolution of gas had ceased. LCMS showed clean conversion to product. The sample was mixed with water (50 mL) and the organic phase was removed by evaporation under reduced pressure, resulting in precipitation in the aqueous phase. The mixture was diluted with water (100 mL). The precipitate was collected on a Buchner funnel and washed with water (200 mL). The damp filter cake was transferred to a 200 mL round-bottom flask and treated with heptane. The mixture was evaporated under reduced pressure to provide a yellow solid. LCMS and $^1$H NMR are consistent with ethyl 6-chloro-8-methoxy-2-oxo-1,2-dihydroquinoline-3-carboxylate (1.73 g, 6.13 mmol, 80% yield). $^1$H NMR (300 MHz, DMSO-d$_6$): δ ppm 11.43 (s, 1H), 8.41 (s, 1H), 7.52 (d, J=2.05 Hz, 1H), 7.28 (d, J=2.05 Hz, 1H), 4.27 (q, J=7.04 Hz, 2H), 3.92 (s, 3H), 1.29 (t, J=7.04 Hz, 3H). LCMS: m/z 282 [M+H]$^+$.

Step 5: 6-chloro-3-(hydroxymethyl)-8-methoxyquinolin-2(1H)-one (IV-5)

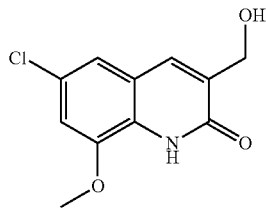

A suspension of ethyl 6-chloro-8-methoxy-2-oxo-1,2-dihydroquinoline-3-carboxylate (1.72 g, 6.11 mmol) in THF (34 ml) was cooled on a dry ice/acetone bath. DIBAL-H (1 M in THF, 28 ml, 28.0 mmol) was added dropwise (~15 minutes). The mixture was stirred 5 minutes, then the bath was replaced with an ice bath and the reaction was stirred at 0° C. for 2.5 hours, during which the solids soon went into solution. LCMS at 1.5 hours showed the reaction had gone nearly to completion. The reaction was quenched with water (40 mL), then removed from the ice bath. Aqueous Rochelle salt (125 mL) was added and the mixture was stirred one hour. The mixture was extracted with EtOAc (2×400 mL). The organic extracts were washed with brine (200 mL), dried (MgSO4), filtered, and evaporated under reduced pressure to provide a yellow solid. LCMS and $^1$H NMR are consistent with 6-chloro-3-(hydroxymethyl)-8-methoxyquinolin-2(1H)-one IV-5 (1.41 g, 5.88 mmol, 96% yield). $^1$H NMR (300 MHz, DMSO-d$_6$): δ ppm 11.14 (s, 1H), 7.85-7.79 (m, 1H), 7.43 (d, J=2.05 Hz, 1H), 7.15 (d, J=2.05 Hz, 1H), 5.31 (t, J=5.42 Hz, 1H), 4.45-4.35 (m, 2H), 3.91 (s, 3H). LCMS: m/z 240 [M+H]$^+$.

Step 6: 6-chloro-8-methoxy-2-oxo-1,2-dihydroquinoline-3-carbaldehyde (IV-6)

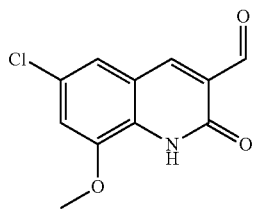 [SMILES: COc1cc(Cl)cc2cc(C=O)c(=O)[nH]c12]

A suspension of 6-chloro-3-(hydroxymethyl)-8-methoxyquinolin-2(1H)-one (479.2 mg, 2.0 mmol) and manganese dioxide (526.4 mg) in chloroform (20 ml) was stirred at 45° C. After 1 day more MnO$_2$ (438.2 mg) was added and the mixture was stirred further at 45° C. for additional 1.5 days, then one more day at room temperature. The mixture was diluted with 1:1 DCM-MeOH (100 mL), then filtered through Celite 545 on a Buchner funnel, and the filter cake was washed with more 1:1 DCM-MeOH. The filtrate was evaporated to provide 0.48 g yellow solid. LCMS and $^1$H NMR are consistent with impure 6-chloro-8-methoxy-2-oxo-1,2-dihydroquinoline-3-carbaldehyde IV-6 (0.48 g, 2.020 mmol, 101% yield). $^1$H NMR (300 MHz, DMSO-d$_6$): δ ppm 11.69 (br s, 1H), 10.23 (s, 1H), 8.44 (s, 1H), 7.62 (d, J=2.05 Hz, 1H), 7.32 (d, J=1.76 Hz, 1H), 3.93 (s, 3H). The sample was used without further purification. LCMS: m/z 238 [M+H]$^+$.

Example 12—Intermediate VI-2: 4-((6-chloro-8-hydroxy-2-oxo-1,2-dihydroquinolin-3-yl)methylamino)-2-methoxybenzonitrile

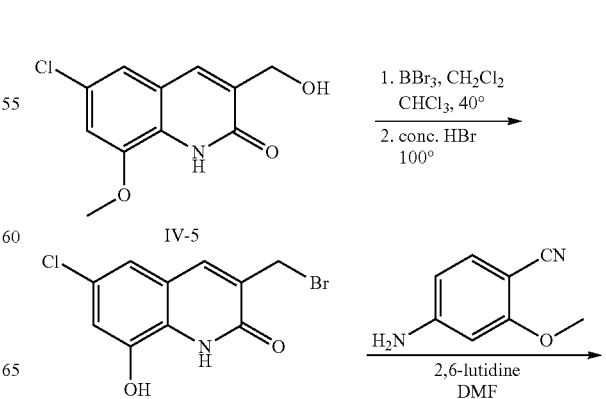

-continued

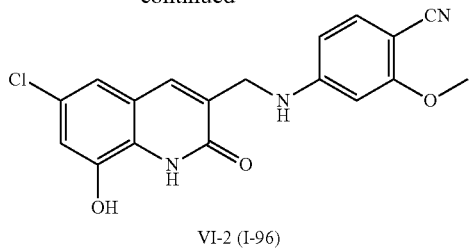

VI-2 (I-96)

Step 1: 3-(bromomethyl)-6-chloro-8-hydroxyquinolin-2(1H)-one

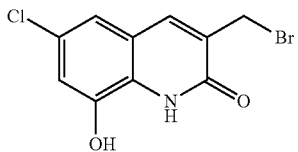 [SMILES: O=c1[nH]c2c(O)cc(Cl)cc2cc1CBr]

A sample of 6-chloro-3-(hydroxymethyl)-8-methoxyquinolin-2(1H)-one IV-5 (236 mg, 0.991 mmol) was placed under nitrogen in a 100 mL round-bottom flask. Chloroform (15 ml) was added. The mixture was cooled on an ice bath, and BBr$_3$ (1.0 M in DCM, 3.0 mL, 3.00 mmol) was added dropwise (3 min). The ice bath was removed and the mixture was stirred at 40° C., during which the material went into solution and then a yellow solid precipitated. At 4.25 hours and 7.5 hours the sample was removed from heat, more BBr$_3$ solution (1.0 mL) was added dropwise, and the sample was returned to 40° C. At a total reaction time ~9.25 hours, the sample was allowed to cool, then cooled on an ice bath and treated dropwise with water (10 mL). The organic solvents were removed by evaporation under reduced pressure, resulting in precipitation in the remaining aqueous phase. The precipitate was collected on a Hirsch funnel, washed with water (~15 mL), and air dried to provide 287 mg yellow solid. LCMS indicated a 69:22:6 mixture of 6-chloro-8-hydroxy-3-(hydroxymethyl)quinolin-2(1H)-one (m/z 226 [M+H]$^+$), 3-(bromomethyl)-6-chloro-8-hydroxyquinolin-2 (1H)-one (m/z 288, 290 [M+H]$^+$), and starting material. The mixture was treated with 48% hydrobromic acid (8.0 mL, 69.2 mmol) and stirred at 100° C. for 1 hour. The suspension was removed from heat, then diluted with water to 50 mL. The solids were collected on a Buchner funnel, washed with water (40 mL), and air-dried on the funnel to provide 3-(bromomethyl)-6-chloro-8-hydroxyquinolin-2(1H)-one (243 mg, 0.842 mmol, 85%) as a tan powder, suitable for use as is. $^1$H NMR (300 MHz, DMSO-d$_6$): δ ppm 11.13 (s, 1H), 10.88 (s, 1H), 8.07 (s, 1H), 7.25 (d, J=2.05 Hz, 1H), 6.92 (d, J=2.05 Hz, 1H), 4.55 (s, 2H). LCMS (Method 1): Rt 2.20 min., m/z 289.8 [M+H]$^+$.

Step 2: 4-((6-chloro-8-hydroxy-2-oxo-1,2-dihydroquinolin-3-yl)methylamino)-2-methoxy benzonitrile (VI-2, I-96)

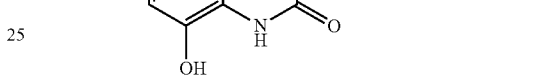

A suspension of 3-(bromomethyl)-6-chloro-8-hydroxyquinolin-2(1H)-one (32.9 mg, 0.114 mmol) and 4-amino-2-methoxybenzonitrile (25.1 mg, 0.169 mmol) in DMF (1.3 ml) was treated with a 10% (v/v) solution of 2,6-lutidine in DMF (130.0 μL) and stirred at room temperature over the weekend. LCMS showed ~5:1 product and bromide starting material. The solution was evaporated under high vacuum at 60° C. The residue was dissolved in a few mL MeOH, treated with silica gel, and evaporated under reduced pressure. The material was chromatographed by Biotage MPLC (10 g silica gel column, 0 to 10% MeOH in DCM, with isocratic elution when peaks came off) to provide the title compound (VI-2, I-96) (7.3 mg, 0.020 mmol, 17.35% yield, HPLC purity 96.4% at 220 nm) as a white solid. $^1$H NMR (300 MHz, DMSO-d$_6$): δ ppm 10.96 (br s, 2H), 7.66 (s, 1H), 7.29 (d, J=8.50 Hz, 1H), 7.14-7.24 (m, 2H), 6.87 (d, J=2.05 Hz, 1H), 6.32 (s, 1H), 6.18-6.27 (m, 1H), 4.23 (d, J=5.90 Hz, 2H), 3.78 (s, 3H). LCMS (Method 4): Rt 1.22 min., m/z 356.0 [M+H]$^+$.

TABLE 1

The Intermediates listed in Table 1 were either prepared using the methods described above or obtained from commercial sources.

| Intermediate No. | Chemical names | Structure |
| --- | --- | --- |
| II-1 | (S)-3-(1-aminoethyl)-6-chloroquinolin-2(1H)-one | ![structure] |

TABLE 1-continued

The Intermediates listed in Table 1 were either prepared using the methods described above or obtained from commercial sources.

| Intermediate No. | Chemical names | Structure |
| --- | --- | --- |
| II-2 | (R)-3-(1-aminoethyl)-6-chloroquinolin-2(1H)-one | 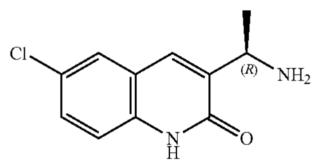 |
| II-3 | 3-(1-aminoethyl)-6-chloro-7-methoxyquinolin-2(1H)-one | 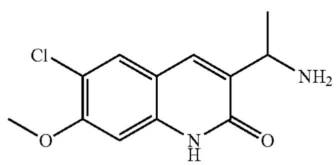 [SMILES: COc1cc2[nH]c(=O)c(C(C)N)cc2cc1Cl] |
| II-4 | (S)-3-(1-aminoethyl)-6-chloro-7-methoxyquinolin-2(1H)-one | 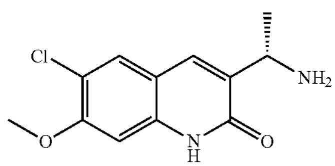 [SMILES: COc1cc2[nH]c(=O)c([C@H](C)N)cc2cc1Cl] |
| II-5 | (R)-3-(1-aminoethyl)-6-chloro-7-methoxyquinolin-2(1H)-one | 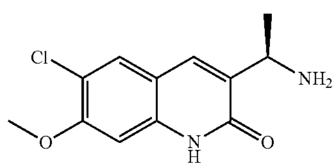 [SMILES: COc1cc2[nH]c(=O)c([C@@H](C)N)cc2cc1Cl] |
| II-6 | 3-(1-aminoethyl)-6-chloro-7-(pyridin-2-ylmethoxy)quinolin-2(1H)-one | 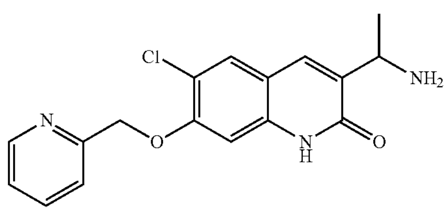 [SMILES: CC(N)c1cc2cc(Cl)c(OCc3ccccn3)cc2[nH]c1=O] |
| II-7 | (S)-3-(1-aminoethyl)-6-chloro-7-(pyridin-2-ylmethoxy)quinolin-2(1H)-one | 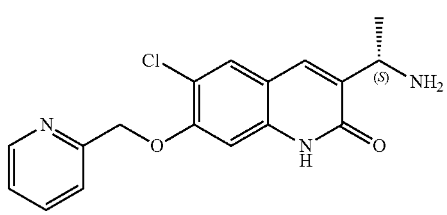 |
| III-1 | 4-fluoro-2-methoxybenzonitrile | 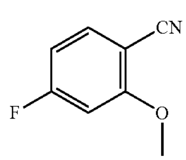 |
| IV-1 | 6-chloro-2-oxo-1,2-dihydroquinoline-3-carbaldehyde | 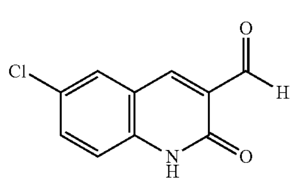 [SMILES: O=Cc1cc2cc(Cl)ccc2[nH]c1=O] |

TABLE 1-continued

The Intermediates listed in Table 1 were either prepared using the methods described above or obtained from commercial sources.

| Intermediate No. | Chemical names | Structure |
|---|---|---|
| IV-2 | 6-chloro-7-methoxy-2-oxo-1,2-dihydroquinoline-3-carbaldehyde | 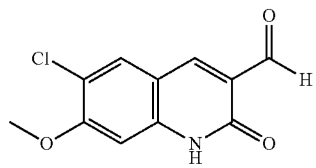 [SMILES: COc1cc2[nH]c(=O)c(C=O)cc2cc1Cl] |
| IV-3 | 6-chloro-7-hydroxy-2-oxo-1,2-dihydroquinoline-3-carbaldehyde | 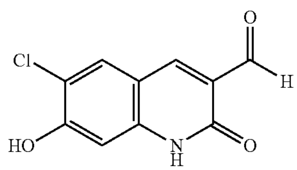 [SMILES: O=Cc1cc2cc(Cl)c(O)cc2[nH]c1=O] |
| IV-4 | 6-chloro-2-oxo-7-(pyridin-2-ylmethoxy)-1,2-dihydroquinoline-3-carbaldehyde | 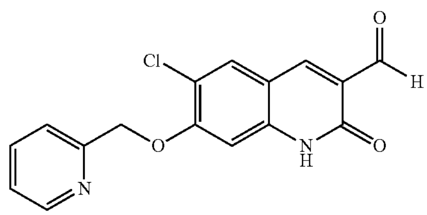 [SMILES: O=Cc1cc2cc(Cl)c(OCc3ccccn3)cc2[nH]c1=O] |
| IV-5 | 6-chloro-3-(hydroxymethyl)-8-methoxyquinolin-2(1H)-one | 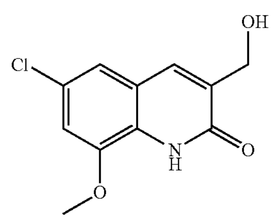 [SMILES: COc1cc(Cl)cc2cc(CO)c(=O)[nH]c12] |
| IV-6 | 6-chloro-8-methoxy-2-oxo-1,2-dihydroquinoline-3-carbaldehyde | 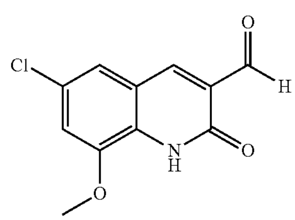 [SMILES: COc1cc(Cl)cc2cc(C=O)c(=O)[nH]c12] |
| IV-7 | 7-chloro-2-oxo-1,2-dihydroquinoline-3-carbaldehyde | 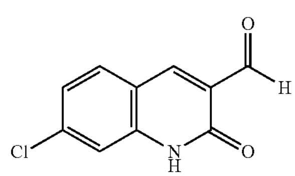 [SMILES: O=Cc1cc2ccc(Cl)cc2[nH]c1=O] |
| IV-8 | 6-methoxy-2-oxo-1,2-dihydroquinoline-3-carbaldehyde | 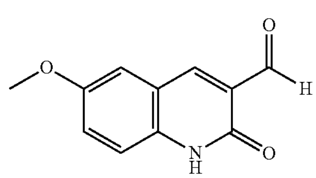 |
| IV-9 | 7-methoxy-2-oxo-1,2-dihydroquinoline-3-carbaldehyde | 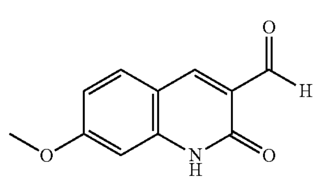 |

TABLE 1-continued

The Intermediates listed in Table 1 were either prepared using the methods described above or obtained from commercial sources.

| Intermediate No. | Chemical names | Structure |
|---|---|---|
| IV-10 | 6,7-dimethyl-2-oxo-1,2-dihydroquinoline-3-carbaldehyde | 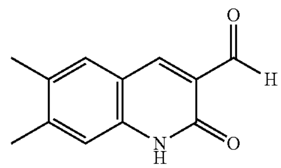 |
| IV-11 | 6-(tert-butyl)-2-oxo-1,2-dihydroquinoline-3-carbaldehyde | 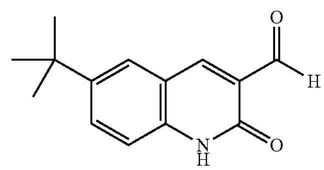 [SMILES: CC(C)(C)c1ccc2[nH]c(=O)c(C=O)cc2c1] |
| V-1 | 4-amino-2-methoxybenzonitrile | 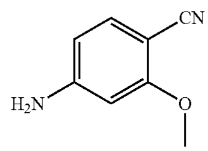 |
| VI-1 | 4-(((6-chloro-7-hydroxy-2-oxo-1,2-dihydroquinolin-3-yl)metthyl)amino)-2-methoxybenzonitrile | 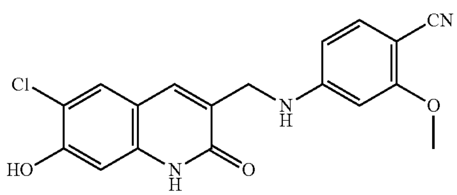 [SMILES: COc1cc(NCc2cc3cc(Cl)c(O)cc3[nH]c2=O)ccc1C#N] |
| VI-2 (I-96) | 6-(((6-chloro-7-hydroxy-2-oxo-1,2-dihydroquinolin-3-yl)methyl)amino)-2-methylnicotinonitrile | 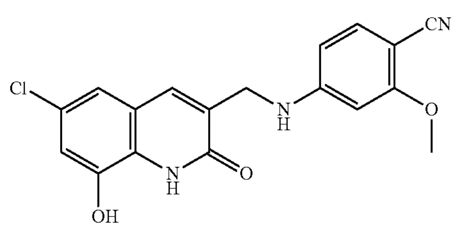 [SMILES: COc1cc(NCc2cc3cc(Cl)cc(O)c3[nH]c2=O)ccc1C#N] |

Note:
All amines are hydrochloride salts.

Example 13—4-(1-(6-chloro-2-oxo-1,2-dihydroquinolin-3-yl)ethylamino)-2-methoxy benzonitrile (I-1)

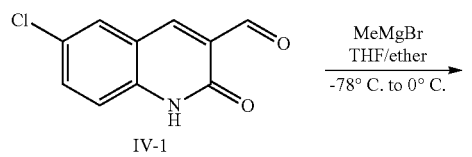

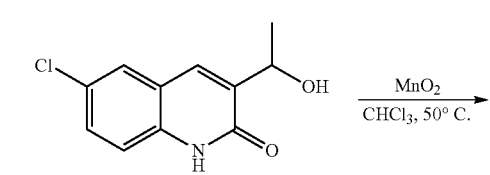

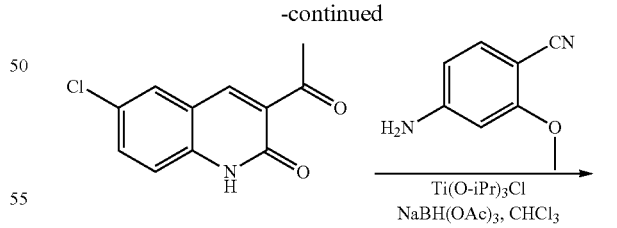

Step-1: 6-chloro-3-(1-hydroxyethyl)quinolin-2(1H)-one

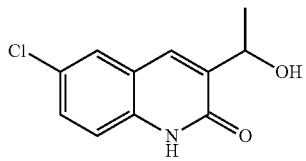

A stirred suspension of 6-chloro-2-oxo-1,2-dihydroquinoline-3-carbaldehyde (498.3 mg, 2.400 mmol) in THF (Volume: 24 ml) under nitrogen was cooled on a dry ice/acetone bath (approximately −78° C.). Methylmagnesium bromide (3.0M in ether, 2.00 mL, 6.00 mmol) was added dropwise (~10 minutes). The suspension was warmed incrementally to 0° C. during 1.5 hours, during which time the suspension gradually became a clear red solution. The solution was stirred at 0° C. for 45 minutes, then the reaction was quenched by addition of several mL water. Water (100 mL) and EtOAc (150 mL) were added and the mixture was shaken, then allowed to settle overnight. The organic layer was evaporated under reduced pressure. The resulting material (~2 g) was dissolved in MeOH, treated with silica gel, and evaporated under reduced pressure. The material was chromatographed by Biotage MPLC (50 g silica gel column, 0 to 100% EtOAc in hexanes) to provide 6-chloro-3-(1-hydroxyethyl)quinolin-2(1H)-one (337 mg, 1.507 mmol, 63% yield) as a yellow solid. $^1$H NMR (300 MHz, DMSO-$d_6$) δ ppm 11.89 (s, 1H), 7.90 (s, 1H), 7.84 (d, J=2.35 Hz, 1H), 7.48 (dd, J=8.79, 2.35 Hz, 1H), 7.30 (d, J=8.79 Hz, 1H), 5.24 (d, J=4.40 Hz, 1H), 4.84-4.73 (m, 1H), 1.30 (d, J=6.45 Hz, 3H). LCMS (Method 1): Rt 1.85 min., m/z 224.0 [M+H]$^+$.

Step-2: 3-acetyl-6-chloroquinolin-2(1H)-one

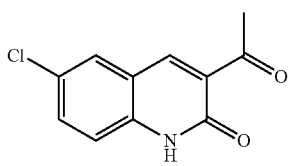

A suspension of 6-chloro-3-(1-hydroxyethyl)quinolin-2(1H)-one (335 mg, 1.498 mmol) and manganese dioxide (392 mg, 4.51 mmol) in chloroform (15 ml) was stirred at 45° overnight. The temperature was increased to 50° C. and the reaction was continued. At two days heating was discontinued. The mixture was diluted with MeOH (20 mL), then filtered through Celite 545, and the Celite was washed with 1:1 DCM-MeOH (40 mL). The filter cake was slurried with DMF (50 mL), then filtered through Celite 545. The filtrate was evaporated to provide 181 mg gray solid. The material was mixed with MeOH, treated with silica gel, and evaporated under reduced pressure. The material was chromatographed by Biotage MPLC (10 g silica gel column) with 0 to 20% MeOH in DCM to provide 3-acetyl-6-chloroquinolin-2(1H)-one as an off-white solid (136.5 mg, 0.616 mmol, 41% yield). $^1$H NMR (300 MHz, DMSO-$d_6$): δ ppm 12.24 (s, 1H), 8.43 (s, 1H), 8.02 (d, J=2.1 Hz, 1H), 7.65 (dd, J=2.5, 8.9 Hz, 1H), 7.35 (d, J=9.1 Hz, 1H), 2.61 (s, 3H). LCMS (Method 1): Rt 2.00 min., m/z 221.88 [M+H]$^+$.

Step-3: 4-(1-(6-chloro-2-oxo-1,2-dihydroquinolin-3-yl)ethylamino)-2-methoxybenzonitrile (I-1)

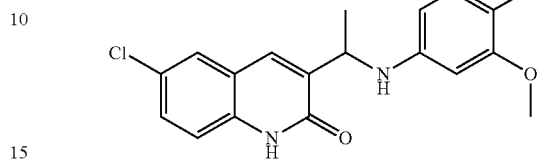

A mixture of 3-acetyl-6-chloroquinolin-2(1H)-one (39.4 mg, 0.178 mmol) and 4-amino-2-methoxybenzonitrile (27.2 mg, 0.184 mmol) was placed under nitrogen in a dram vial. Dichloromethane (1.0 ml) was added and the suspension was stirred 10 minutes. Triisopropoxytitanium(IV) chloride (0.09 mL, 0.377 mmol) was added and the suspension was stirred overnight. Sodium triacetoxyborohydride (148.3 mg, 0.700 mmol) was added and the mixture was stirred one day. The sample was diluted with several mL MeOH, treated with silica gel, and evaporated under reduced pressure. The sample was chromatographed by Biotage MPLC with 0 to 20% MeOH in DCM, with isocratic elution at 13% MeOH. The material thus obtained was reabsorbed onto silica gel and rechromatographed (10 g silica gel column) with 0 to 80% EtOAc in hexanes, with isocratic elution at 50% EtOAc to provide 4-(1-(6-chloro-2-oxo-1,2-dihydroquinolin-3-yl)ethylamino)-2-methoxybenzonitrile, I-1 as a racemic mixture (20.3 mg, 0.053 mmol, 29.6% yield, HPLC purity 91.63% at UV220). 1H NMR (300 MHz, DMSO-d6): δ=12.05 (s, 1H), 7.80-7.69 (m, 2H), 7.50 (d, J=8.8 Hz, 1H), 7.36-7.15 (m, 3H), 6.27 (s, 1H), 6.06 (d, J=7.6 Hz, 1H), 4.82-4.66 (m, J=6.4, 6.4 Hz, 1H), 3.75 (s, 3H), 1.44 (d, J=6.4 Hz, 3H). LCMS (Method 1): Rt 2.37 min., m/z 353.92 [M+H]$^+$.

Examples 14—(S)-4-((1-(6-chloro-2-oxo-1,2-dihydroquinolin-3-yl)ethyl)amino)-2-methoxy benzonitrile (I-2) and (R)-4-((1-(6-chloro-2-oxo-1,2-dihydroquinolin-3-yl)ethyl)amino)-2-methoxybenzonitrile (I-3)

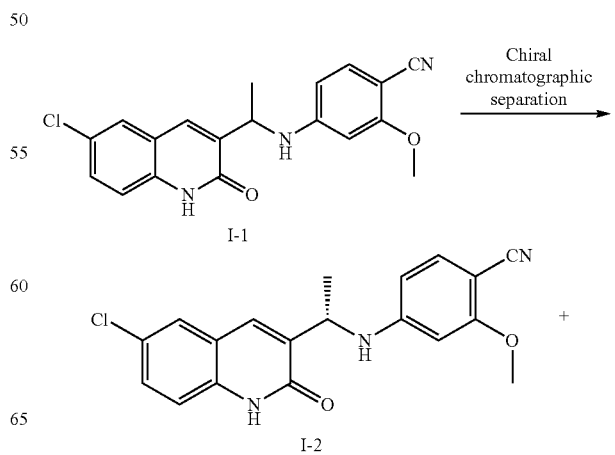

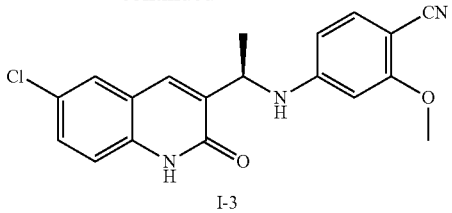

I-3

A racemic mixture, 4-(1-(6-chloro-2-oxo-1,2-dihydroquinolin-3-yl)ethylamino)-2-methoxy benzonitrile, I-1 (14 mg) racemic mixture was subjected a chiral chromatographic separation to yield I-2 and I-3>
Chiral separation of the racemic mixture was performed to provide two pure enantiomers.
Chiral HPLC Condition:
Injection Volume: 20 uL
Column: ASH
Mobile phase: Hex:EtOH=80:20
Gradient time 20 min
Detector: 220 nm
Instrument: HP1100
Temperature: 25° C.

(S)-4-((1-(6-chloro-2-oxo-1,2-dihydroquinolin-3-yl)ethyl)amino)-2-methoxy benzonitrile (I-2)

1.8 mg obtained, Chiral HPLC: Rt: 10.02 min, ee: 94%.

(R)-4-((1-(6-chloro-2-oxo-1,2-dihydroquinolin-3-yl)ethyl)amino)-2-methoxybenzonitrile (I-3)

1.4 mg, Chiral HPLC: Rt: 8.04 min, ee: 99.8%.

Example 15—An Alternative Approach to I-2: (S)-4-((1-(6-chloro-2-oxo-1,2-dihydroquinolin-3-yl)ethyl)amino)-2-methoxybenzonitrile

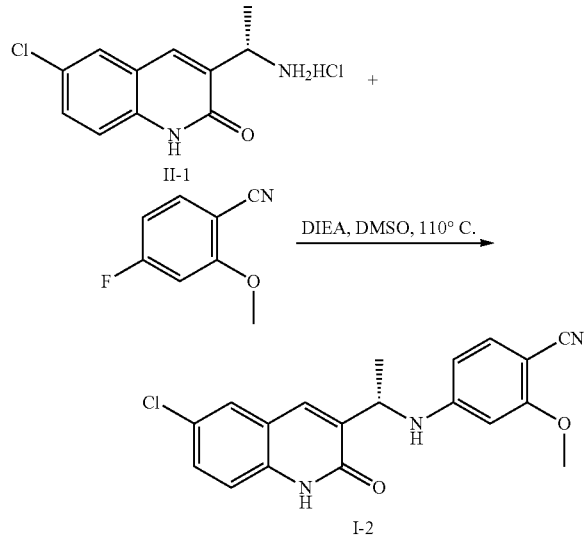

A solution of (S)-3-(1-aminoethyl)-6-chloroquinolin-2(1H)-one hydrochloride II-1 (201 mg, 0.776 mmol) and 4-fluoro-2-methoxybenzonitrile (236 mg, 1.56 mmol) in DMSO (5 ml) was treated with DIEA (400 µl, 2.29 mmol) and stirred at 110° C. for three days. The sample was diluted with water (75 mL) and extracted with DCM (2×50 mL), dried, and filtered. Silica gel was added, and the solvent was evaporated under reduced pressure. The material was chromatographed by Biotage MPLC (silica gel, 0 to 70% EtOAc in hexanes, with isocratic elution when peaks came off) to provide a gum. The material was dissolved in DCM (10 mL), washed with water (2×10 mL), dried ($Na_2SO_4$), filtered, and evaporated to provide 76 mg yellow powder. The sample was mixed with MeCN (4 mL) and water (2 mL), frozen on a dry ice/acetone bath, and lyopholyzed to provide the title compound I-2 (71.1 mg, 0.193 mmol, 24.93% yield, HPLC purity 96.3% at 220 nm) as a solid. $^1$H NMR (300 MHz, DMSO-$d_6$): δ ppm 12.07 (s, 1H), 7.77 (d, J=2.35 Hz, 1H), 7.74 (s, 1H), 7.50 (dd, J=8.65, 1.91 Hz, 1H), 7.35-7.20 (m, 3H), 6.27 (s, 1H), 6.06 (d, J=7.90 Hz, 1H), 4.79-4.65 (m, 1H), 3.75 (s, 3H), 1.43 (d, J=6.45 Hz, 3H). LCMS (Method 1): Rt 2.37 min., m/z 354.0 $[M+H]^+$.

Example 16—(S)-4-((1-(6-chloro-2-oxo-7-(pyridin-2-ylmethoxy)-1,2-dihydroquinolin-3-yl)ethyl)amino)-2-methoxybenzonitrile (I-5)

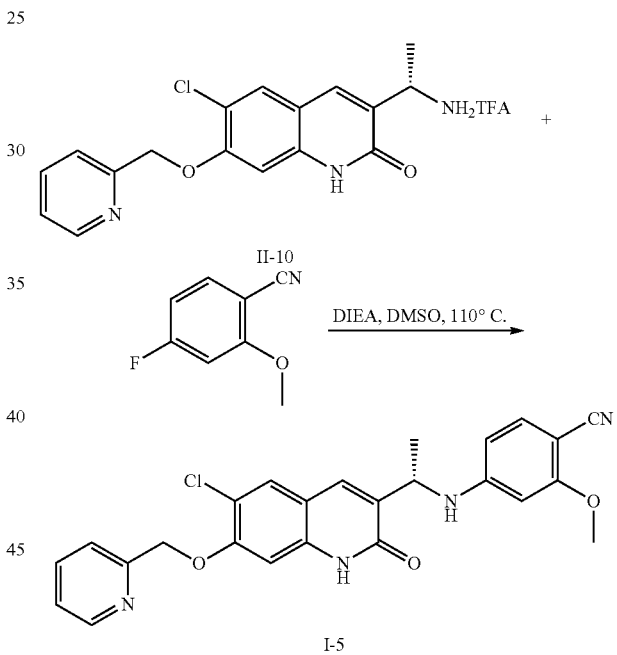

A mixture of 4-fluoro-2-methoxybenzonitrile (15.9 mg, 0.105 mmol) (Oakwood) and 3-(1-aminoethyl)-6-chloro-7-(pyridin-2-ylmethoxy)quinolin-2(1H)-one hydrochloride (34.7 mg, 0.095 mmol) (730-06) was treated with DMSO (0.7 ml) and DIEA (50 µl, 0.286 mmol). The solution was stirred at 110° two days. More fluoromethoxybenzonitrile (8.3 mg) was added and the solution was stirred at 110° two more days. The solution was allowed to cool, then the sample was diluted with MeOH, silica gel was added, and the sample was evaporated under reduced pressure. The material was chromatographed by Biotage MPLC (10 g silica gel snap column) with 0 to 10% MeOH in DCM, with isocratic elution at 2.5% MeOH while product came off. The product fractions were evaporated under reduced pressure to provide a nonvolatile liquid, apparently DMSO. The sample was dissolved in EtOAc (20 mL), washed with water (2×20 mL), and evaporated under reduced pressure to provide 4.2 mg residue, FT00730-08-1. LCMS is consistent with 4-((1-(6-chloro-2-oxo-7-(pyridin-2-ylmethoxy)-1,2-dihydroquinolin-3-yl)ethyl)amino)-2-methoxybenzonitrile I-5 (4.4 mg, 9.55 mol, 10.08% yield), LCMS: m/z 461 [M+H]⁺.

Example 17—(S)-6-chloro-3-(1-((3-methoxy-4-(methylsulfonyl)phenyl)amino)ethyl)quinolin-2(1H)-one (I-6)

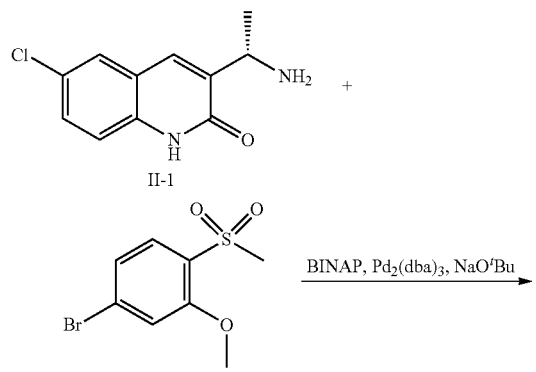

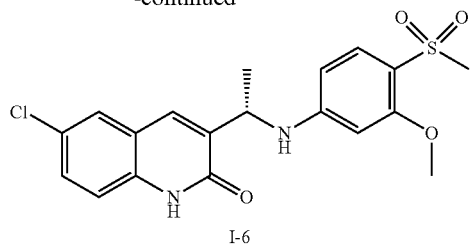

A mixture of (S)-3-(1-aminoethyl)-6-chloroquinolin-2(1H)-one hydrochloride (Intermediate II-1, 40 mg, 0.155 mmol), 4-bromo-2-methoxy-1-(methylsulfonyl)benzene (62 mg, 0.233 mmol), BINAP (13.6 mg, 0.022 mmol), Pd₂(dba)₃ (11.0 mg, 0.012 mmol), and sodium tert-butoxide (35.7 mg, 0.371 mmol) was placed under nitrogen in a 2 dram vial. Toluene (1.0 ml) was added by syringe and the mixture was shaken at 80° C. overnight. The residue was triturated in 1 mL MeOH. The sample was diluted with MeOH/DCM, treated with silica gel, and evaporated under reduced pressure. The material was chromatographed by Biotage MPLC (10 g silica gel column) with 0 to 10% MeOH in DCM, with isocratic elution at 2.6% MeOH to provide (S)-6-chloro-3-(1-(3-methoxy-4-(methylsulfonyl)phenylamino)ethyl)quinolin-2(1H)-one as a yellow solid I-6 (9.1 mg, 0.021 mmol, 14% yield, LCMS purity 96% at UV220). LCMS (Method 1): Rt 2.15 min., m/z 406.86 [M+H]+.

TABLE 1

The compounds listed in Table 1 were prepared using methods similar to those described for the preparation of I-1, I-3, I-4, and I-6.

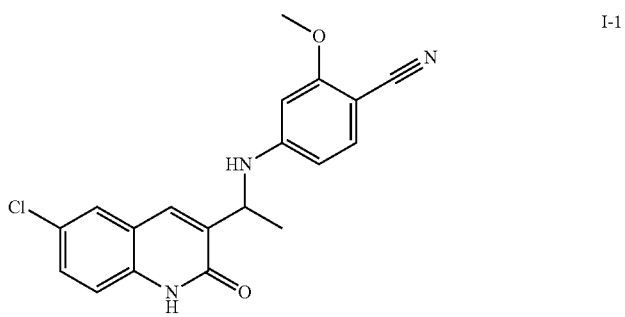

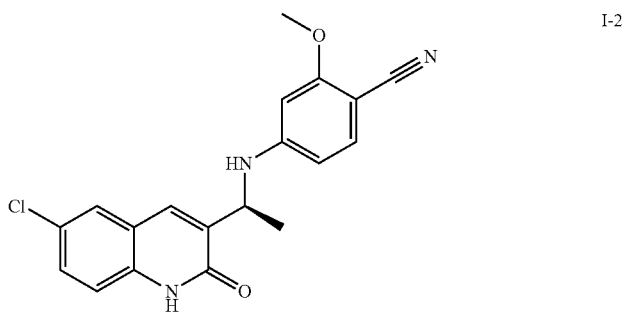

TABLE 1-continued

The compounds listed in Table 1 were prepared using methods similar to those described for the preparation of I-1, I-3, I-4, and I-6.

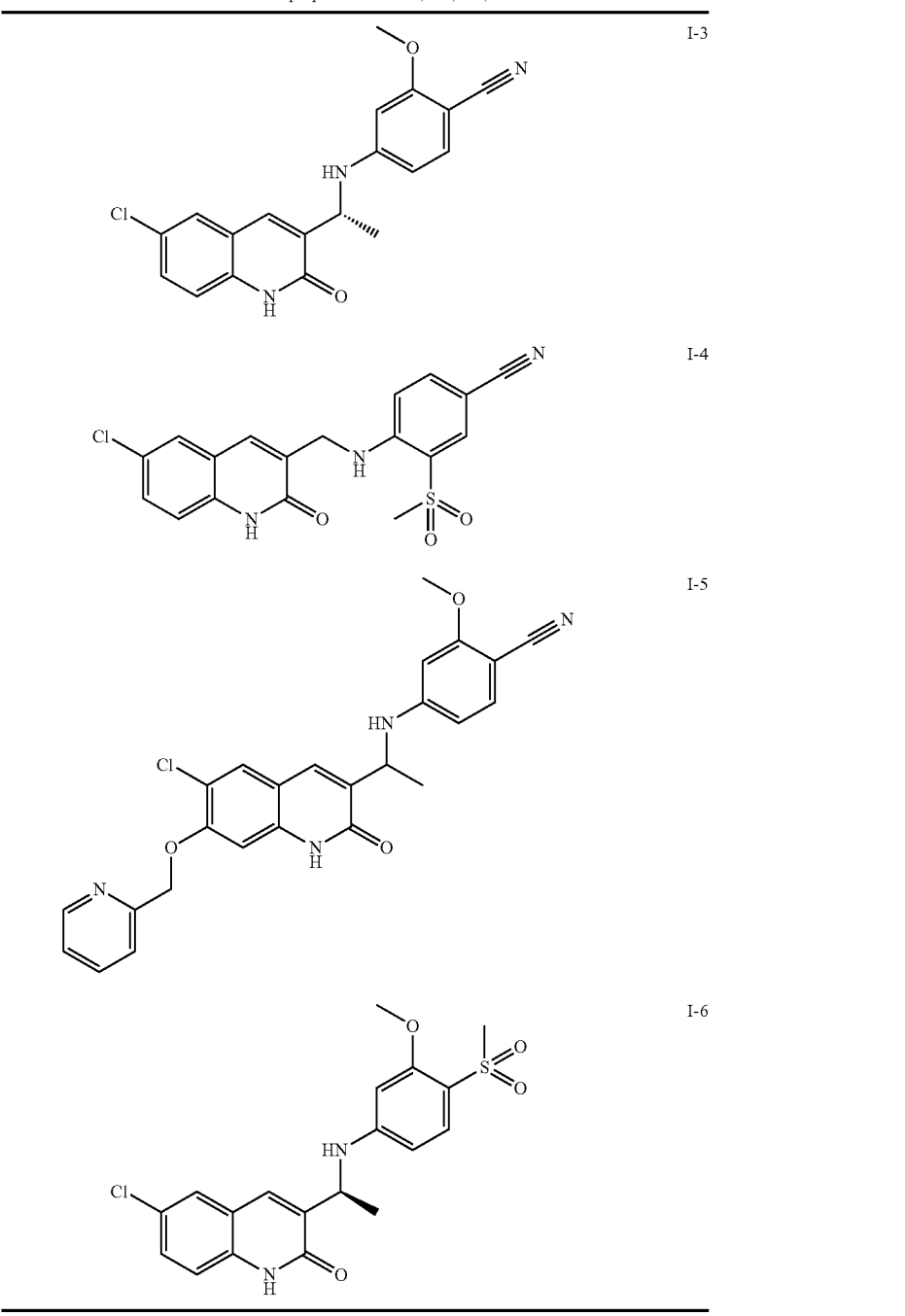

TABLE 2

LCMS signal and NMR chemical shifts of each compound listed in Table 1.

| Cmpd No | LCMS[a] | 1H NMR (300 MHz) δ ppm | Chemical Name |
|---|---|---|---|
| I-1 | m/z: 354.05 (M + H)+<br>Rt (min): 1.32 | 1H NMR (300 MHz, DMSO-d6): δ ppm 12.05 (s, 1 H), 7.76 (d, J = 7.00 Hz, 2 H), 7.50 (d, J = 8.80 Hz, 1 H), 7.36-7.15 (m, 3 H), 6.27 (s, 1 H), 6.06 (d, J = 7.60 Hz, 1 H), 4.72 (m, 1 H), 3.75 (s, 3 H), 1.44 (d, J = 6.40 Hz, 3 H). | 4-{[1-(6-chloro-2-oxo-1,2-dihydroquinolin-3-yl)ethyl]amino}-2-methoxybenzonitrile |

TABLE 2-continued

LCMS signal and NMR chemical shifts of each compound listed in Table 1.

| Cmpd No | LCMS[a] | 1H NMR (300 MHz) δ ppm | Chemical Name |
|---|---|---|---|
| I-2 | m/z: 354.05 (M + H)+<br>Rt (min): 1.34 | 1H NMR (300 MHz, DMSO-d6): δ ppm 12.07 (s, 1 H), 7.77 (d, J = 2.35 Hz, 1 H), 7.74 (s, 1 H), 7.50 (dd, J = 8.65, 1.91 Hz, 1 H), 7.35-7.20 (m, 3 H), 6.27 (s, 1 H), 6.06 (d, J = 7.90 Hz, 1 H), 4.79-4.65 (m, 1 H), 3.75 (s, 3 H), 1.43 (d, J = 6.45 Hz, 3 H). | 4-{[(1S)-1-(6-chloro-2-oxo-1,2-dihydroquinolin-3-yl)ethyl]amino}-2-methoxybenzonitrile |
| I-3 | m/z: 354.03 (M + H)+<br>Rt (min): 1.33 | | 4-{[(1R)-1-(6-chloro-2-oxo-1,2-dihydroquinolin-3-yl)ethyl]amino}-2-methoxybenzonitrile |
| I-4 | m/z: 402.04 (M + H)+<br>Rt (min): 1.46 | 1H NMR (300 MHz, DMSO-d6): δ 12.12 (br, 1H), 7.95 (d, J = 2.05 Hz, 1H), 7.89 (s, 1H), 7.72-7.85 (m, 2H), 7.52-7.47 (m, 1H), 7.29 (d, J = 8.47 Hz, 1H), 6.74 (d, J = 8.89 Hz, 1H),, 4.87 (m, 1H), 3.31 (s, 3H), 1.40 (d, J = 6.85 Hz, 3H) | 4-{[(1S)-1-(6-chloro-2-oxo-1,2-dihydroquinolin-3-yl)ethyl]amino}-3-methanesulfonylbenzonitrile |
| I-5 | m/z: 461.17 (M + H)+<br>Rt (min): 1.38 | | 4-({1-[6-chloro-2-oxo-7-(pyridin-2-ylmethoxy)-1,2-dihydroquinolin-3-yl]ethyl}amino)-2-methoxybenzonitrile |
| I-6 | m/z: 407.08 (M + H)+<br>Rt (min): 1.16 | | 6-chloro-3-[(1S)-1-[(4-methanesulfonyl-3-methoxyphenyl)amino]ethyl]-1,2-dihydroquinolin-2-one |

[a]LCMS data are determined by Method 4.

Example 18—4-(((6-chloro-2-oxo-1,2-dihydroquinolin-3-yl)methyl)amino)-2-methoxybenzonitrile (I-7)

To a 100 mL round bottom flask was added 6-chloro-2-oxo-1,2-dihydroquinoline-3-carbaldehyde IV-1 (200 mg, 0.963 mmol), 4-amino-2-methoxybenzonitrile (150 mg, 1.01 mmol) and AcOH (0.276 ml, 4.82 mmol) in DCE (15 ml). Finally sodium triacetoxyborohydride (364 mg, 1.93 mmol) was added and the mixture was stirred at room temperature overnight. LC-MS indicated only about 50% conversion. The reaction mixture was diluted with EtOAc (60 mL) and washed with water (×2) and brine. The organic was dried over Na$_2$SO$_4$, filtered and concentrated to yield a crude. The crude was dissolved in 3 mL of DMSO and purified by preparative HPLC on Gilson, yielding 34 mg of pure product (10.4% yield). $^1$H NMR (300 MHz, CDCl$_3$) δ ppm 11.11 (br s, 1H), 7.58 (s, 1H), 7.49-7.43 (m, 1H), 7.42-7.33 (m, 1H), 7.27-7.19 (m, 2H), 6.14 (dd, J=8.50, 2.05 Hz, 1H), 6.06 (d, J=1.76 Hz, 1H), 4.37 (s, 2H), 3.80-3.72 (m, 3H). LCMS (Method 1): Rt 2.34 min, m/z 340.00 [M+H]$^+$.

TABLE 3

The compounds listed in Table 3 were prepared using methods similar to those described for the preparation of 1-7.

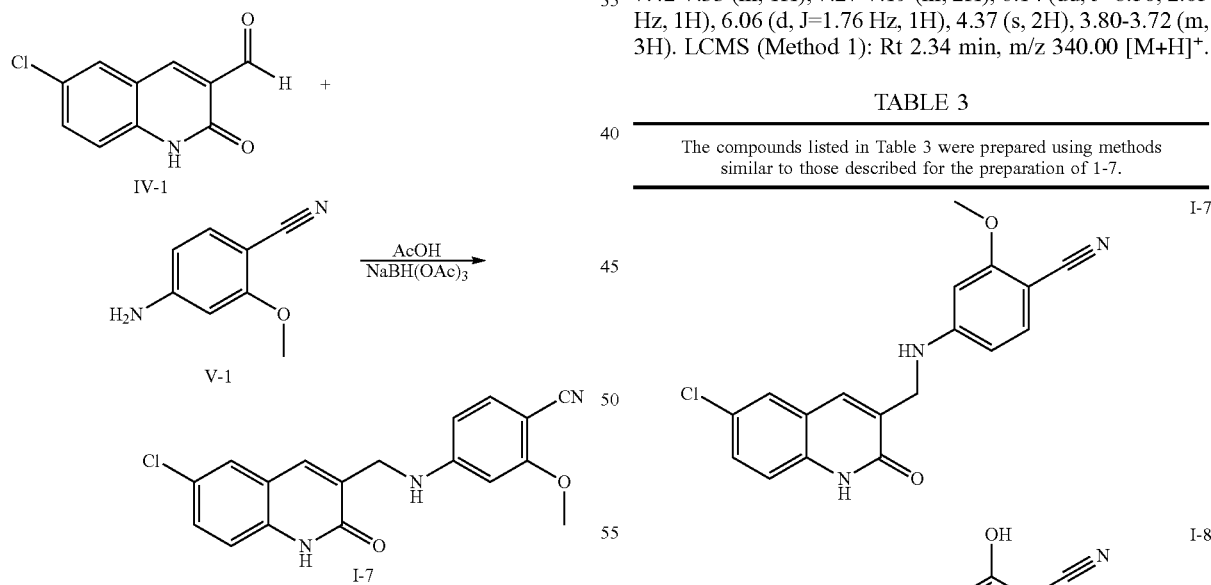

TABLE 3-continued
The compounds listed in Table 3 were prepared using methods similar to those described for the preparation of 1-7.
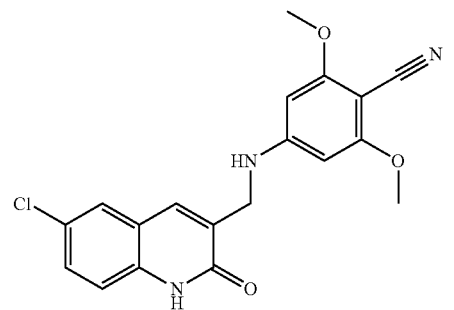 [SMILES: COc1cc(NCc2cc3cc(Cl)ccc3[nH]c2=O)cc(OC)c1C#N]
I-9
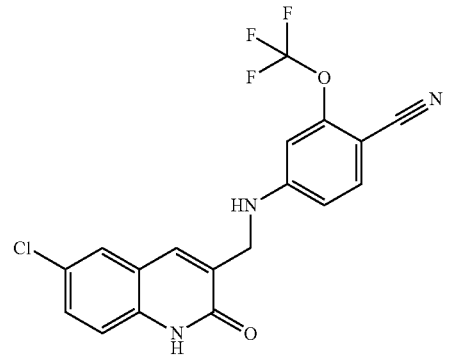 [SMILES: N#Cc1ccc(NCc2cc3cc(Cl)ccc3[nH]c2=O)cc1OC(F)(F)F]
I-10
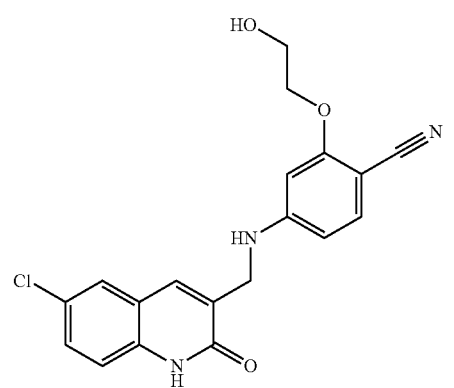 [SMILES: N#Cc1ccc(NCc2cc3cc(Cl)ccc3[nH]c2=O)cc1OCCO]
I-11
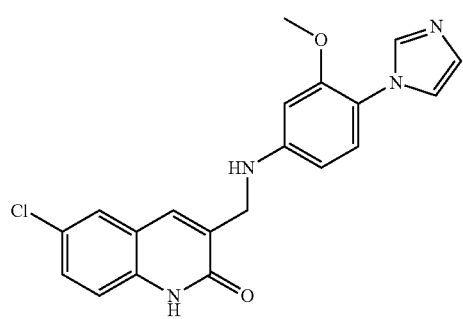 [SMILES: COc1cc(NCc2cc3cc(Cl)ccc3[nH]c2=O)ccc1-n1ccnc1]
I-12
TABLE 3-continued
The compounds listed in Table 3 were prepared using methods similar to those described for the preparation of 1-7.
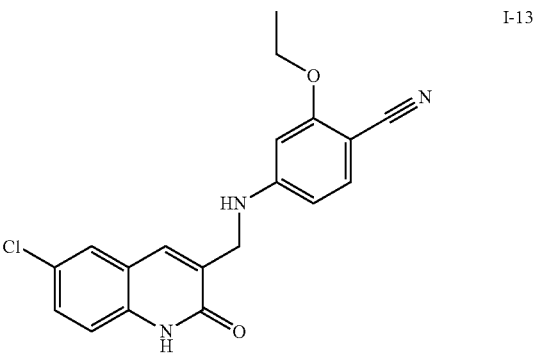
I-13
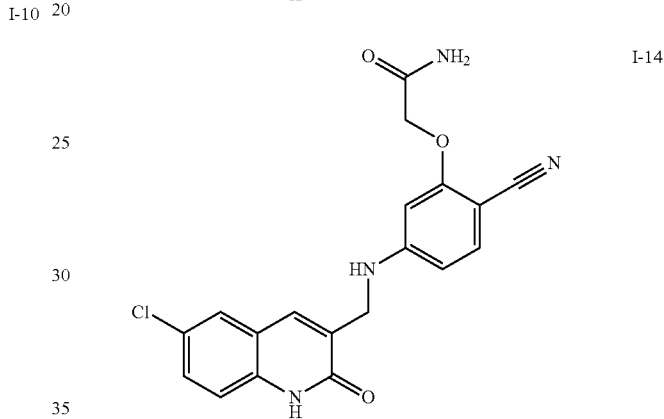
I-14
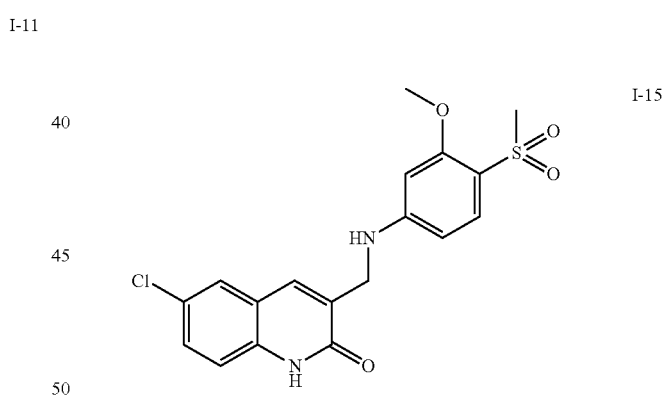
I-15
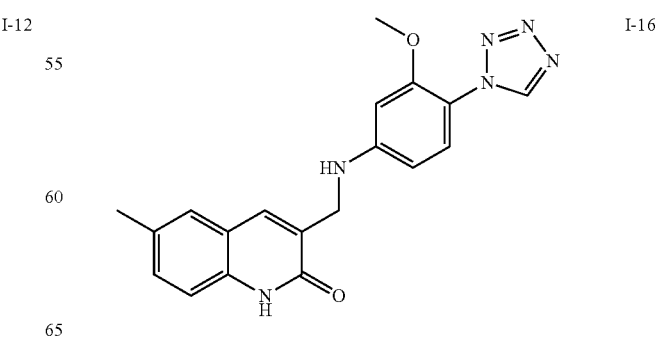
I-16

TABLE 3-continued
The compounds listed in Table 3 were prepared using methods similar to those described for the preparation of 1-7.
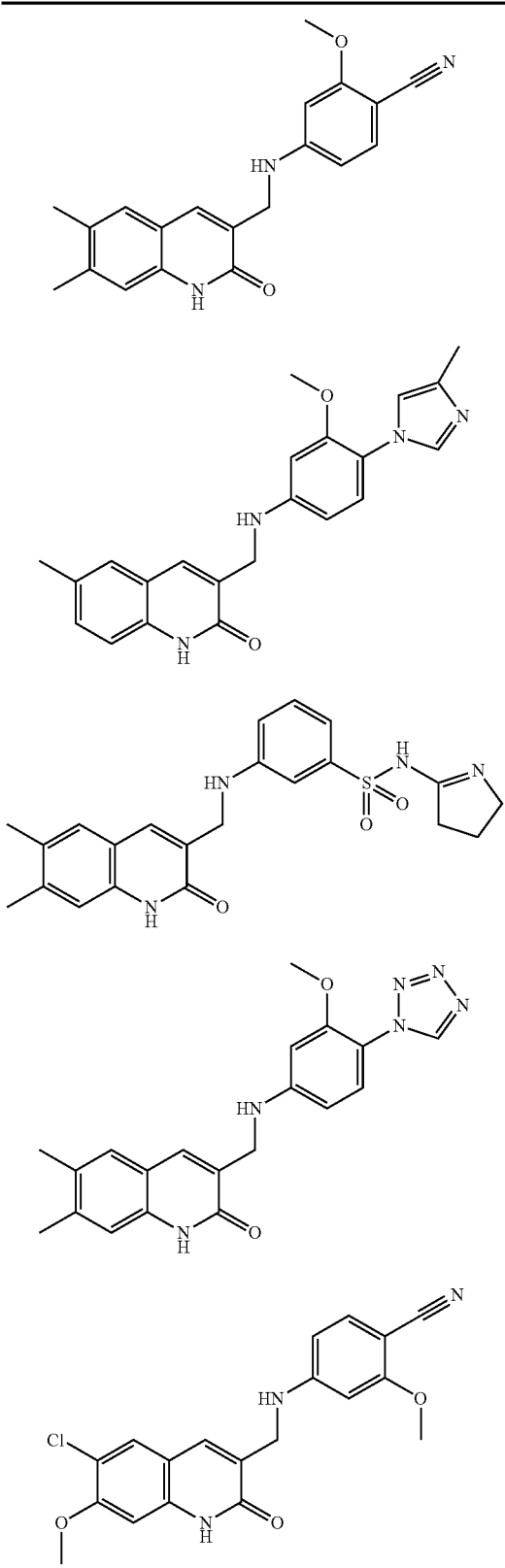
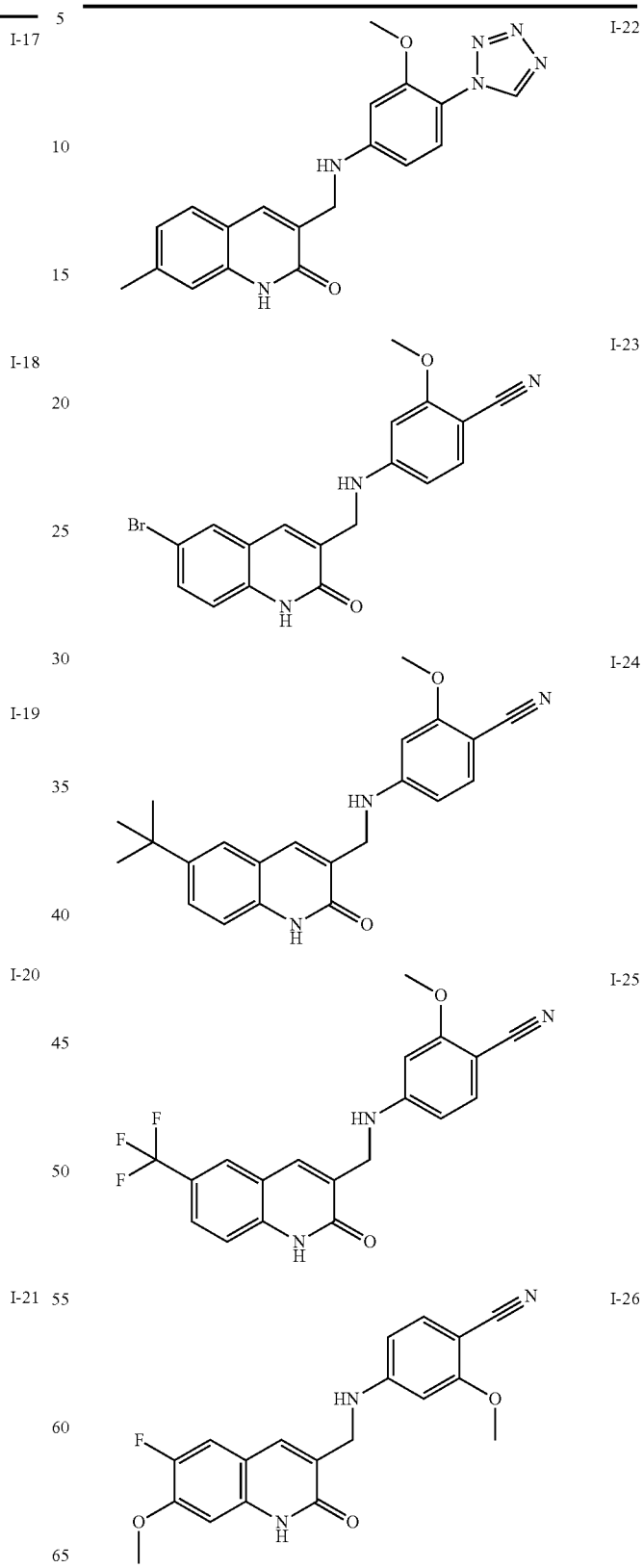

TABLE 3-continued

The compounds listed in Table 3 were prepared using methods similar to those described for the preparation of 1-7.

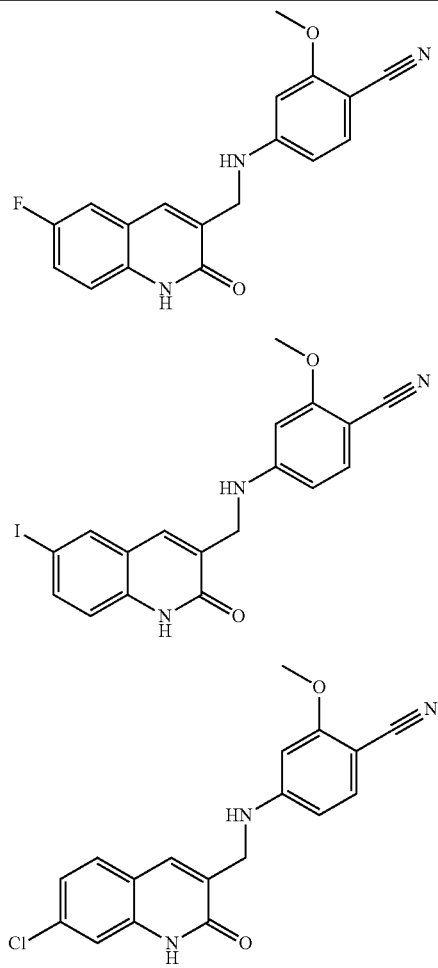

I-27

I-28

I-29

The compounds listed in Table 3 were prepared using methods similar to those described for the preparation of 1-7.

I-30

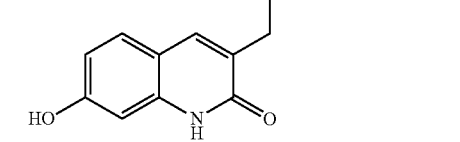

I-31

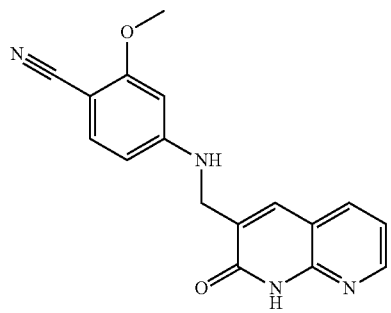 [SMILES: COc1cc(NCc2cc3cccnc3[nH]c2=O)ccc1C#N]

TABLE 4

LCMS signal and NMR chemical shifts of each compound listed in Table 3.

| Cmpd No | LCMS[a] | 1H NMR (300 MHz) δ ppm | Chemical Name |
|---|---|---|---|
| I-7 | m/z: 340.03 (M + H)+ Rt (min): 1.32 | 1H NMR (300 MHz, CHLOROFORM-d) δ ppm 11.11 (br s, 1 H), 7.58 (s, 1 H), 7.49-7.43 (m, 1 H), 7.42-7.33 (m, 1 H), 7.27-7.19 (m, 2 H), 6.14 (dd, J = 8.50, 2.05 Hz, 1 H), 6.06 (d, J = 1.76 Hz, 1 H), 4.37 (s, 2 H), 3.80-3.72 (m, 3 H). | 4-{[(6-chloro-2-oxo-1,2-dihydroquinolin-3-yl)methyl]amino}-2-methoxybenzonitrile |
| I-8 | m/z: 326.0533 (M + H)+ Rt (min): 1.17 | 1H NMR (300 MHz, DMSO-d6) δ ppm 12.01 (s, 1 H), 10.34 (s, 1 H), 7.74 (d, J = 2.35 Hz, 1 H), 7.59 (s, 1 H), 7.44 (t, J = 1.00 Hz, 1 H), 7.27 (s, 1 H), 7.14 (d, J = 8.50 Hz, 1 H), 6.16-6.07 (m, 1 H), 5.99 (d, J = 1.76 Hz, 1 H), 4.08 (br d, J = 4.98 Hz, 2 H). | 4-{[(6-chloro-2-oxo-1,2-dihydroquinolin-3-yl)methyl]amino}-2-hydroxybenzonitrile |
| I-9 | m/z: 370.0931 (M + H)+ Rt (min): 1.29 | 1H NMR (300 MHz, DMSO) δppm: 12.12 (br s, 1H), 7.83 (br d, J = 14.7 Hz, 2H), 7.59-7.50 (m, 1H), 7.37 (s, 1H), 7.20 (br s, 1H), 5.99 (m, 2H), 4.30 (br s, 2H), 3.79 (s, 6H) | 4-{[(6-chloro-2-oxo-1,2-dihydroquinolin-3-yl)methyl]amino}-2,6-dimethoxybenzonitrile |
| I-10 | m/z: 394.0791 (M + H)+ Rt (min): 1.5 | 1H NMR (300 MHz, CD3OD): δppm 7.85-7.75 (m, 1H), 7.65-7.50 ((m, 3H), 7.50-7.47 (m, 2H), 7.34-7.30 (m, 1H), 6.65-6.60 ((m,, 2H), 4.35 (s, 2H) | 4-{[(6-chloro-2-oxo-1,2-dihydroquinolin-3-yl)methyl]amino}-2-(trifluoromethoxy)benzonitrile |

TABLE 4-continued

LCMS signal and NMR chemical shifts of each compound listed in Table 3.

| Cmpd No | LCMS[a] | 1H NMR (300 MHz) δ ppm | Chemical Name |
|---|---|---|---|
| I-11 | m/z: 370.0931 (M + H)+ Rt (min): 1.15 | 1H NMR (300 MHz, DMSO-d6): δ ppm 12.06 (s, 1 H), 7.80 (d, J = 2.05 Hz, 1 H), 7.72 (s, 1 H), 7.50 (dd, J = 8.79, 2.35 Hz, 1 H), 7.30 (m, 2 H), 7.21-7.10 (m, 1 H), 6.32 (s, 1 H), 6.23 (d, J = 9.10 Hz, 1 H), 4.92-4.84 (m, 1 H), 4.23 (d, J = 5.90 Hz, 2 H), 4.01 (t, J = 5.00 Hz, 2 H), 3.70 (m, 2 H). | 4-{[(6-chloro-2-oxo-1,2-dihydroquinolin-3-yl)methyl]amino}-2-(2-hydroxyethoxy)benzonitrile |
| I-12 | m/z: 381.1774 (M + H)+ Rt (min): 0.93 | 1H NMR (300 MHz, CHLOROFORM-d) δ ppm 7.68 (s, 1 H), 7.63 (s, 1 H), 7.53 (d, J = 2.35 Hz, 1 H), 7.42 (dd, J = 8.50, 2.35 Hz, 1 H), 7.19 (d, J = 8.79 Hz, 1 H), 7.05 (dd, J = 14.80, 8.65 Hz, 2 H), 6.29 (d, J = 2.35 Hz, 1 H), 6.23 (dd, J = 8.21, 2.35 Hz, 1 H), 4.38 (s, 2 H), 3.74 (s, 3 H). | 6-chloro-3-({[4-(1H-imidazol-1-yl)-3-methoxyphenyl]amino}methyl)-1,2-dihydroquinolin-2-one |
| I-13 | m/z: 354.1019 (M + H)+ Rt (min): 1.39 | 1H NMR (300 MHz, DMSO-d6): δ ppm 12.06 (s, 1 H), 7.80 (s, 1 H), 7.72 (s, 1 H), 7.50 (d, J = 7.30 Hz, 1 H), 7.37-7.23 (m, 2 H), 7.22-7.09 (m, 1 H), 6.35-6.15 (m, 2 H), 4.23 (br d, J = 4.69 Hz, 2 H), 4.04 (m, 2 H), 1.42-1.20 (m, 3 H). | 4-{[(6-chloro-2-oxo-1,2-dihydroquinolin-3-yl)methyl]amino}-2-ethoxybenzonitrile |
| I-14 | m/z: 383.02 (M + H)+ Rt (min): 2.16 | 1H NMR (300 MHz, CHLOROFORM-d) δ ppm 9.51 (br s, 1 H), 7.56 (s, 1 H), 7.48 (m, 1 H), 7.39-7.37 (m, 1 H), 7.14-7.07 (m, 2 H), 6.21 (d, J = 9.9 Hz, 1 H), 6.03 (m, 1 H), 4.43 (s, 2 H), 4.33 (s, 2 H). | 2-(5-{[(6-chloro-2-oxo-1,2-dihydroquinolin-3-yl)methyl]amino}-2-cyanophenoxy)acetamide |
| I-15 | m/z: 393.1003 (M + H)+ Rt (min): 1.15 | 1H NMR (300 MHz, DMSO-d6): δ ppm 12.07 (s, 1 H), 7.81 (d, J = 2.35 Hz, 1 H), 7.74 (s, 1 H), 7.50 (dd, J = 8.79, 2.35 Hz, 1 H), 7.43 (d, J = 8.79 Hz, 1 H), 7.31 (d, J = 8.79 Hz, 1 H), 7.12 (dd, J = 6.00, 6.00 Hz, 1 H), 6.37 (d, J = 1.47 Hz, 1 H), 6.24 (dd, J = 8.94, 1.91 Hz, 1 H), 4.24 (d, J = 5.90 Hz, 2 H), 3.83 (s, 3 H), 3.06 (s, 3 H). | 6-chloro-3-{[(4-methanesulfonyl-3-methoxyphenyl)amino]methyl}-1,2-dihydroquinolin-2-one |
| I-16 | m/z: 363.12 (M + H)+ Rt (min): 1.2 | | 3-({[3-methoxy-4-(1H-1,2,3,4-tetrazol-1-yl)phenyl]amino}methyl)-6-methyl-1,2-dihydroquinolin-2-one |
| I-17 | m/z: 334.14 (M + H)+ Rt (min): 1.35 | | 4-{[(6,7-dimethyl-2-oxo-1,2-dihydroquinolin-3-yl)methyl]amino}-2-methoxybenzonitrile |
| I-18 | m/z: 375.1597 (M + H)+ Rt (min): 0.97 | 1H NMR (300 MHz, CHLOROFORM-d) δ ppm 10.30 (br s, 1 H), 7.64 (s, 1 H), 7.57 (s, 1 H), 7.30-7.20 (m, 2 H), 7.14-7.06 (m, 1 H), 6.93 (d, J = 8.21 Hz, 1 H), 6.71 (s, 1 H), 6.25-6.16 (m, 2 H), 4.33 (s, 2 H), 3.66 (s, 3 H), 2.32 (s, 3 H), 2.22 (s, 3 H). | 3-({[3-methoxy-4-(4-methyl-1H-imidazol-1-yl)phenyl]amino}methyl)-6-methyl-1,2-dihydroquinolin-2-one |
| I-19 | m/z: 425.1331 (M + H)+ Rt (min): 1.08 | | N-(3,4-dihydro-2H-pyrrol-5-yl)-3-{[(6,7-dimethyl-2-oxo-1,2-dihydroquinolin-3-yl)methyl]amino}benzene-1-sulfonamide |
| I-20 | m/z: 377.13 (M + H)+ Rt (min): 1.26 | | 3-({[3-methoxy-4-(1H-1,2,3,4-tetrazol-1-yl)phenyl]amino}methyl)-6,7-dimethyl-1,2-dihydroquinolin-2-one |
| I-21 | m/z: 370.09 (M + H)+ Rt (min): 1.31 | 1H NMR (300 MHz, DMSO-d6): δ ppm 11.92 (s, 1 H), 7.80 (s, 1 H), 7.68 (s, 1 H), 7.29 (d, J = 8.79 Hz, 1 H), 7.15 (dd, J = 5.60, 5.60 Hz, 1 H), 6.95 (s, 1 H), 6.32 (s, 1 H), 6.22 (d, J = 7.90 Hz, 1 H), 4.20 (d, J = 5.30 Hz, 2 H), 3.88 (s, 3 H), 3.78 (s, 3 H). | 4-{[(6-chloro-7-methoxy-2-oxo-1,2-dihydroquinolin-3-yl)methyl]amino}-2-methoxybenzonitrile |
| I-22 | m/z: 363.12 (M + H)+ Rt (min): 1.17 | | 3-({[3-methoxy-4-(1H-1,2,3,4-tetrazol-1-yl)phenyl]amino}methyl)-7-methyl-1,2-dihydroquinolin-2-one |

TABLE 4-continued

LCMS signal and NMR chemical shifts of each compound listed in Table 3.

| Cmpd No | LCMS[a] | 1H NMR (300 MHz) δ ppm | Chemical Name |
|---|---|---|---|
| I-23 | m/z: 384 (M + H)+<br>Rt (min): 1.33 | | 4-{[(6-bromo-2-oxo-1,2-dihydroquinolin-3-yl)methyl]amino}-2-methoxybenzonitrile |
| I-24 | m/z: 362.1616 (M + H)+<br>Rt (min): 1.5 | 1H NMR (300 MHz, DMSO-d6) δ ppm 11.88 (s, 1 H), 7.77 (s, 1 H), 7.63-7.56 (m, 2 H), 7.37-7.26 (m, 2 H), 7.25-7.17 (m, 1 H), 6.36 (s, 1 H), 6.25 (br d, J = 8.21 Hz, 1 H), 4.26 (br d, J = 5.86 Hz, 2 H), 3.81 (s, 3 H), 1.30 (s, 9 H). | 4-{[(6-tert-butyl-2-oxo-1,2-dihydroquinolin-3-yl)methyl]amino}-2-methoxybenzonitrile |
| I-25 | m/z: 374.0438 (M + H)+<br>Rt (min): 1.37 | | 2-methoxy-4-({[2-oxo-6-(trifluoromethyl)-1,2-dihydroquinolin-3-yl]methyl}amino)benzonitrile |
| I-26 | m/z: 354.17 (M + H)+<br>Rt (min): 1.22 | 1H NMR (300 MHz, DMSO-d6): δ ppm 11.88 (s, 1 H), 7.66 (s, 1 H), 7.57 (d, J = 11.73 Hz, 1 H), 7.29 (d, J = 8.50 Hz, 1 H), 7.16 (dd, J = 5.90, 5.90 Hz, 1 H), 6.97 (d, J = 7.62 Hz, 1 H), 6.32 (s, 1 H), 6.22 (d, J = 8.80 Hz, 1 H), 4.20 (d, J = 5.60 Hz, 2 H), 3.87 (s, 3 H), 3.78 (s, 3 H). | 4-{[(6-fluoro-7-methoxy-2-oxo-1,2-dihydroquinolin-3-yl)methyl]amino}-2-methoxybenzonitrile |
| I-27 | m/z: 324.11 (M + H)+<br>Rt (min): 1.2 | 1H NMR (300 MHz, DMSO-d6): δ ppm 12.00 (s, 1 H), 7.73 (s, 1 H), 7.55 (dd, J = 9.09, 2.35 Hz, 1 H), 7.42-7.25 (m, 3 H), 7.24-7.13 (m, 1 H), 6.33 (s, 1 H), 6.28-6.18 (m, 1 H), 4.25 (d, J = 5.00 Hz, 2 H), 3.79 (s, 3 H). | 4-{[(6-fluoro-2-oxo-1,2-dihydroquinolin-3-yl)methyl]amino}-2-methoxybenzonitrile |
| I-28 | m/z: 431.97 (M + H)+<br>Rt (min): 1.39 | 1H NMR (300 MHz, DMSO-d6): δ ppm 12.03 (s, 1 H), 8.06 (m, 1 H), 7.74 (dd, J = 8.65, 1.91 Hz, 1 H), 7.70 (s, 1 H), 7.29 (m, 1 H), 7.22-7.15 (m, 1 H), 7.12 (m, 1 H), 6.32 (s, 1 H), 6.22 (d, J = 8.50 Hz, 1 H), 4.23 (d, J = 5.90 Hz, 2 H), 3.78 (s, 3 H). | 4-{[(6-iodo-2-oxo-1,2-dihydroquinolin-3-yl)methyl]amino}-2-methoxybenzonitrile |
| I-29 | m/z: 339.97 (M + H)+<br>Rt (min): 1.32 | 1H NMR (300 MHz, CHLOROFORM-d) δ ppm 7.63-7.54 (m, 1 H), 7.42-7.33 (m, 1 H), 7.26-7.17 (m, 5 H), 7.14-7.05 (m, 1 H), 6.18-6.04 (m, 2 H), 4.28 (s, 2 H), 3.78-3.72 (m, 3 H). | 4-{[(7-chloro-2-oxo-1,2-dihydroquinolin-3-yl)methyl]amino}-2-methoxybenzonitrile |
| I-30 | m/z: 322.08 (M + H)+<br>Rt (min): 1.01 | | 4-{[(7-hydroxy-2-oxo-1,2-dihydroquinolin-3-yl)methyl]amino}-2-methoxybenzonitrile |
| I-31 | m/z: 307.14 (M + H)+<br>Rt (min): 0.99 | | 2-methoxy-4-{[(2-oxo-1,2-dihydro-1,8-naphthyridin-3-yl)methyl]amino}benzonitrile |

[a]LCMS data are determined by Method 4.

Library Synthesis Protocol for Preparation of Compounds, I-32 to I-56.

Example 19—4-(((6-chloro-2-oxo-1,2-dihydroquinolin-3-yl)methyl)amino)benzonitrile (I-32)

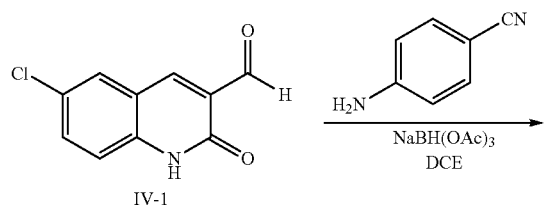

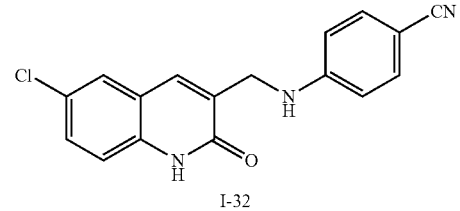

6-Chloro-2-oxo-1,2-dihydroquinoline-3-carbaldehyde V-1 (4.15 mg, 20 umol) was added as a solid to a 0.2 M solution of 4-aminobenzonitrile in DMA (165 uL, 33 umol). An additional volume of 1,2-dichoroethane (150 mL) was added, and the mixture was agitated at room temperature for 5 minutes. The resultant mixture was charged with a 0.2M suspension of sodium triacetoxyborohydride in DCE (200 uL, 40 umol) and was agitated overnight at room temperature. After LC-MS analysis confirmed the presence of reductive amination product, the mixture was partitioned between ethyl acetate (500 uL) and saturated aqueous sodium bicarbonate solution (500 uL). The organic layer was transferred, and the aqueous layer was extracted once more with fresh ethyl acetate (500 uL). The organic layers were combined and concentrated under reduced pressure with heat (50° C.). The crude residue was dissolved in DMSO (500 uL) and purified by mass-triggered preparatory HPLC to yield the title compound (1.0 mg, 16% yield). LCMS (Method 4): Rt 1.30 min, m/z 310.11 [M+H]+.

TABLE 5

The compounds listed in Table 5 were prepared using the method similar to the one described for the preparation of 1-32.

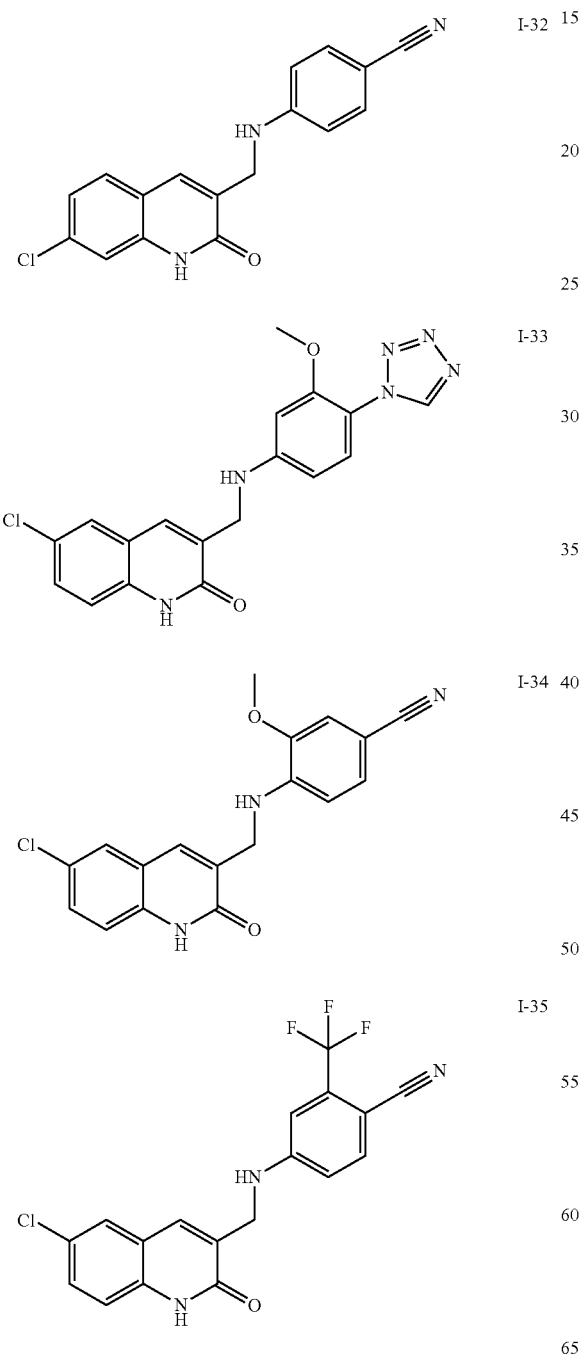

TABLE 5-continued

The compounds listed in Table 5 were prepared using the method similar to the one described for the preparation of 1-32.

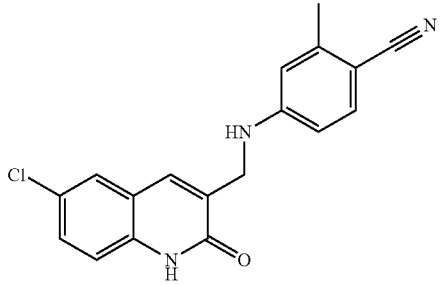 [SMILES: Cc1cc(NCc2cc3cc(Cl)ccc3[nH]c2=O)ccc1C#N]

I-36

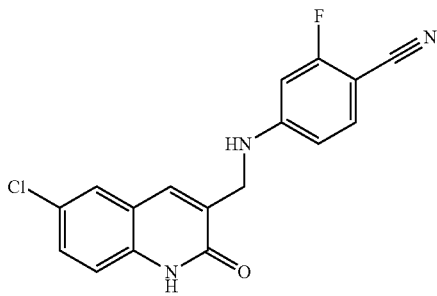 [SMILES: N#Cc1ccc(NCc2cc3cc(Cl)ccc3[nH]c2=O)cc1F]

I-37

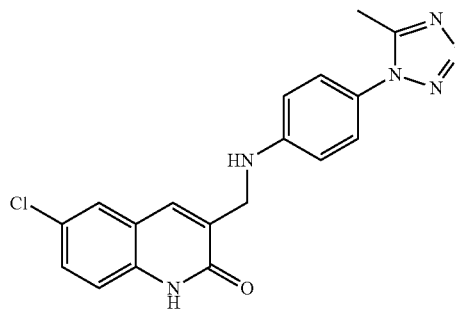

I-38

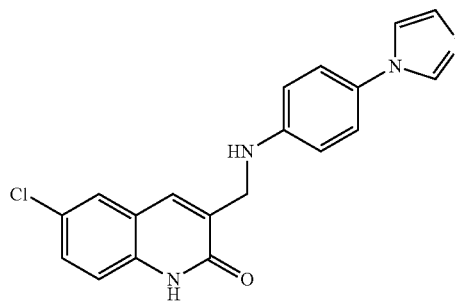

I-39

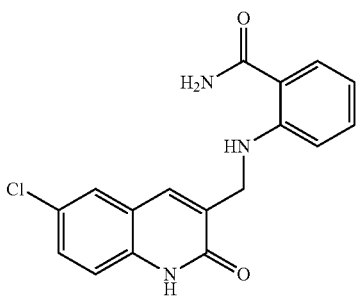 [SMILES: NC(=O)c1ccccc1NCc1cc2cc(Cl)ccc2[nH]c1=O]

I-40

TABLE 5-continued
The compounds listed in Table 5 were prepared using the method similar to the one described for the preparation of 1-32.
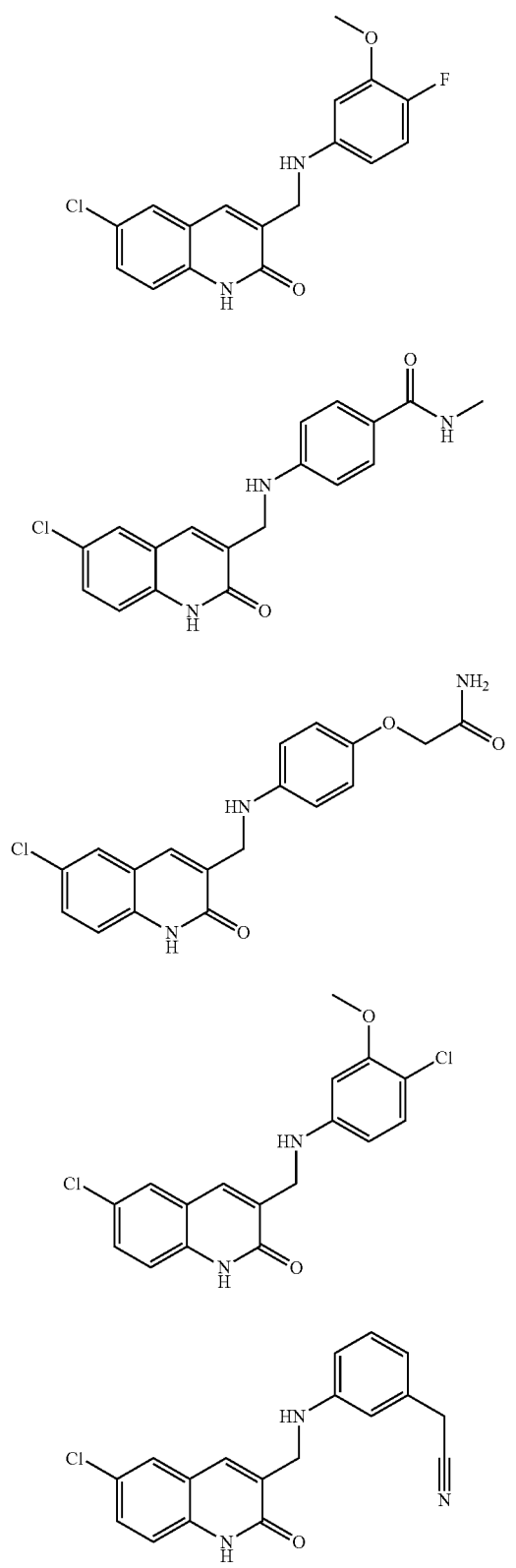

TABLE 5-continued

The compounds listed in Table 5 were prepared using the method similar to the one described for the preparation of 1-32.

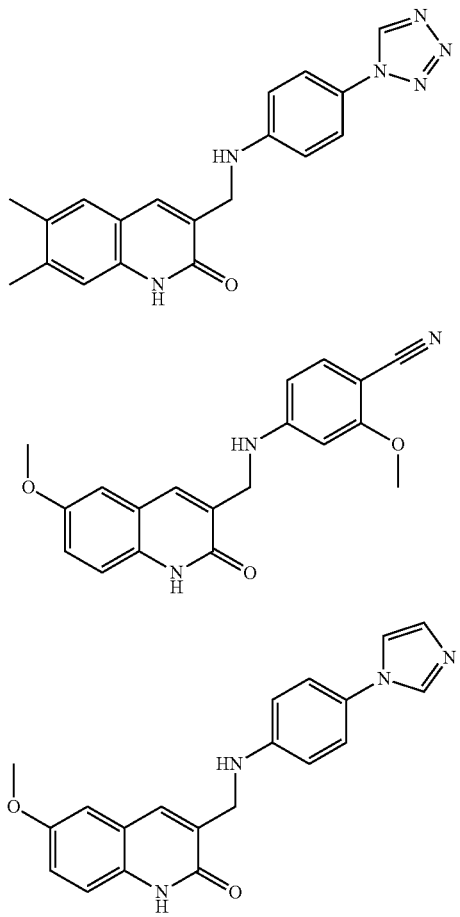

I-51

I-52

I-53

TABLE 5-continued

The compounds listed in Table 5 were prepared using the method similar to the one described for the preparation of 1-32.

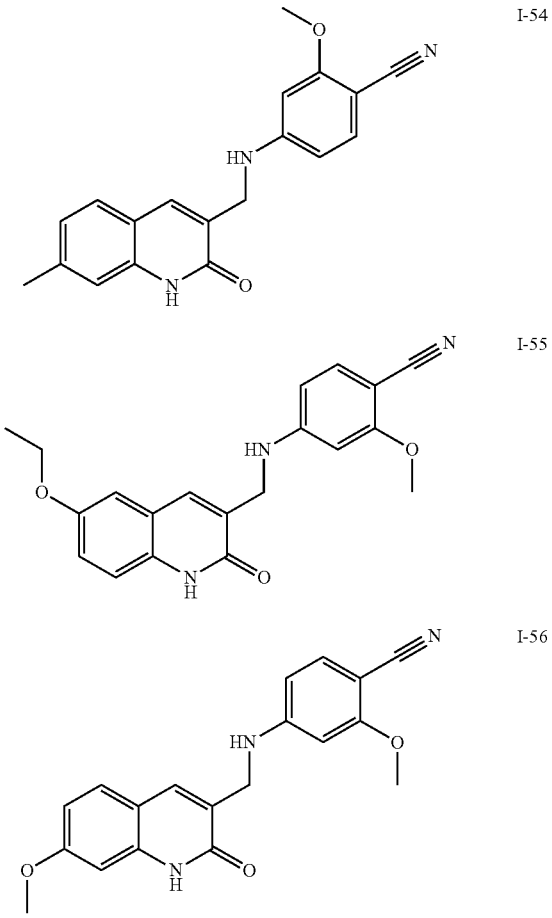

I-54

I-55

I-56

TABLE 6

LCMS signal and chemical names of each compound listed in Table 6.

| Cmpd No | LCMS[a] | Chemical Name |
|---|---|---|
| I-32 | m/z: 310.12 (M + H)+ Rt (min): 1.3 | 4-{[(6-chloro-2-oxo-1,2-dihydroquinolin-3-yl)methyl]amino}benzonitrile |
| I-33 | m/z: 383.15 (M + H)+ Rt (min): 1.22 | 6-chloro-3-({[3-methoxy-4-(1H-1,2,3,4-tetrazol-1-yl)phenyl]amino}methyl)-1,2-dihydroquinolin-2-one |
| I-34 | m/z: 340.06 (M + H)+ Rt (min): 1.37 | 4-{[(6-chloro-2-oxo-1,2-dihydroquinolin-3-yl)methyl]amino}-3-methoxybenzonitrile |
| I-35 | m/z: 378.07 (M + H)+ Rt (min): 1.49 | 4-{[(6-chloro-2-oxo-1,2-dihydroquinolin-3-yl)methyl]amino}-2-(trifluoromethyl)benzonitrile |
| I-36 | m/z: 324.09 (M + H)+ Rt (min): 1.36 | 4-{[(6-chloro-2-oxo-1,2-dihydroquinolin-3-yl)methyl]amino}-2-methylbenzonitrile |
| I-37 | m/z: 350.07 (M + H)+ Rt (min): 1.35 | 4-{[(6-chloro-2-oxo-1,2-dihydroquinolin-3-yl)methyl]amino}-2-fluorobenzonitrile |
| I-38 | m/z: 367.17 (M + H)+ Rt (min): 1.17 | 6-chloro-3-({[4-(5-methyl-1H-1,2,3,4-tetrazol-1-yl)phenyl]amino}methyl)-1,2-dihydroquinolin-2-one |
| I-39 | m/z: 351.12 (M + H)+ Rt (min): 0.88 | 6-chloro-3-({[4-(1H-imidazol-1-yl)phenyl]amino}methyl)-1,2-dihydroquinolin-2-one |
| I-40 | m/z: 327.97 (M + H)+ Rt (min): 1.15 | 2-{[(6-chloro-2-oxo-1,2-dihydroquinolin-3-yl)methyl]amino}benzamide |
| I-41 | m/z: 332.97 (M + H)+ Rt (min): 1.39 | 6-chloro-3-{[(4-fluoro-3-methoxyphenyl)amino]methyl}-1,2-dihydroquinolin-2-one |
| I-42 | m/z: 341.98 (M + H)+ Rt (min): 1 | 4-{[(6-chloro-2-oxo-1,2-dihydroquinolin-3-yl)methyl]amino}-N-methylbenzamide |
| I-43 | m/z: 357.97 (M + H)+ Rt (min): 0.95 | 2-(4-{[(6-chloro-2-oxo-1,2-dihydroquinolin-3-yl)methyl]amino}phenoxy)acetamide |

TABLE 6-continued

LCMS signal and chemical names of each compound listed in Table 6.

| Cmpd No | LCMS[a] | Chemical Name |
|---|---|---|
| I-44 | m/z: 348.92 (M + H)+ Rt (min): 1.5 | 6-chloro-3-{[(4-chloro-3-methoxyphenyl)amino]methyl}-1,2-dihydroquinolin-2-one |
| I-45 | m/z: 324.00 (M + H)+ Rt (min): 1.32 | 2-(3-{[(6-chloro-2-oxo-1,2-dihydroquinolin-3-yl)methyl]amino}phenyl)acetonitrile |
| I-46 | m/z: 303.11 (M + H)+ Rt (min): 1.48 | 6-chloro-3-{[(2-fluorophenyl)amino]methyl}-1,2-dihydroquinolin-2-one |
| I-47 | m/z: 306.12 (M + H)+ Rt (min): 1.16 | 2-methoxy-4-{[(2-oxo-1,2-dihydroquinolin-3-yl)methyl]amino}benzonitrile |
| I-48 | m/z: 349.18 (M + H)+ Rt (min): 1.07 | 3-({[3-methoxy-4-(1H-1,2,3,4-tetrazol-1-yl)phenyl]amino}methyl)-1,2-dihydroquinolin-2-one |
| I-49 | m/z: 319.14 (M + H)+ Rt (min): 1.02 | 3-({[4-(1H-1,2,3,4-tetrazol-1-yl)phenyl]amino}methyl)-1,2-dihydroquinolin-2-one |
| I-50 | m/z: 320.14 (M + H)+ Rt (min): 1.26 | 2-methoxy-4-{[(6-methyl-2-oxo-1,2-dihydroquinolin-3-yl)methyl]amino}benzonitrile |
| I-51 | m/z: 347.14 (M + H)+ Rt (min): 1.2 | 6,7-dimethyl-3-({[4-(1H-1,2,3,4-tetrazol-1-yl)phenyl]amino}methyl)-1,2-dihydroquinolin-2-one |
| I-52 | m/z: 336.13 (M + H)+ Rt (min): 1.16 | 2-methoxy-4-{[(6-methoxy-2-oxo-1,2-dihydroquinolin-3-yl)methyl]amino}benzonitrile |
| I-53 | m/z: 347.22 (M + H)+ Rt (min): 0.75 | 3-({[4-(1H-imidazol-1-yl)phenyl]amino}methyl)-6-methoxy-1,2-dihydroquinolin-2-one |
| I-54 | m/z: 320.12 (M + H)+ Rt (min): 1.25 | 2-methoxy-4-{[(7-methyl-2-oxo-1,2-dihydroquinolin-3-yl)methyl]amino}benzonitrile |
| I-55 | m/z: 350.10 (M + H)+ Rt (min): 1.25 | 4-{[(6-ethoxy-2-oxo-1,2-dihydroquinolin-3-yl)methyl]amino}-2-methoxybenzonitrile |
| I-56 | m/z: 336.13 (M + H)+ Rt (min): 1.2 | 2-methoxy-4-{[(7-methoxy-2-oxo-1,2-dihydroquinolin-3-yl)methyl]amino}benzonitrile |

[a]LCMS data are determined by Method 4.

Example 20—4-((6-chloro-2-oxo-7-(pyridin-2-ylmethoxy)-1,2-dihydroquinolin-3-yl)methylamino)-2-methoxybenzonitrile (I-58)

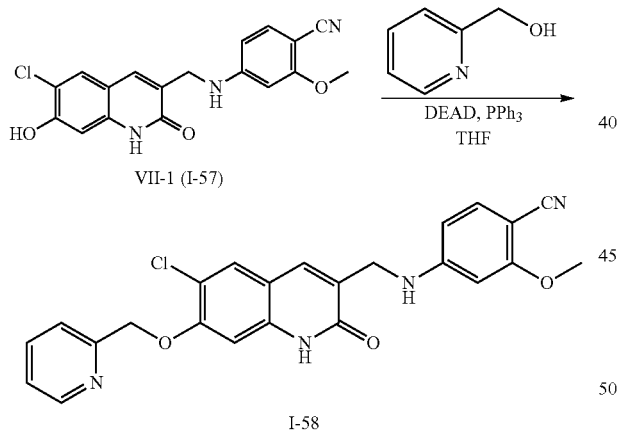

A solution of 4-((6-chloro-7-hydroxy-2-oxo-1,2-dihydroquinolin-3-yl)methylamino)-2-methoxybenzonitrile VI-1 (40 mg, 0.112 mmol), pyridin-2-ylmethanol (11.6 µL, 0.120 mmol), and triphenylphosphine (39.8 mg, 0.152 mmol) in THF (2.6 ml) was treated with DEAD (24 µL, 0.152 mmol) and stirred at room temperature overnight, during which time a material precipitated. LCMS indicated the reaction had gone to completion. MeOH, DCM, and silica gel were added and the mixture was evaporated under reduced pressure. The residue was chromatographed by Biotage MPLC (10 g silica gel column, 0 to 2.7% MeOH in EtOAc). The combined fractions were concentrated. The resulting residue was sonicated a few minutes in 5 mL MeOH in a 40 mL vial, then allowed to settle. The supernatant was removed by pipet and discarded. The sample was mixed with more MeOH (5 mL) and again allowed to settle, and the supernatant was removed and discarded. The sample was dried under reduced pressure to provide the title compound (I-58) (32.1 mg, 0.072 mmol, 28% yield, 99% at 220 nm) as a slightly yellow solid. $^1$H NMR (300 MHz, DMSO-$d_6$): δ ppm 11.91 (s, 1H), 8.67-8.54 (m, 1H), 7.95-7.80 (m, 2H), 7.68 (s, 1H), 7.56 (d, J=7.30 Hz, 1H), 7.44-7.34 (m, 1H), 7.29 (d, J=9.10 Hz, 1H), 7.22-7.13 (m, 1H), 7.03 (s, 1H), 6.31 (br s, 1H), 6.22 (d, J=7.90 Hz, 1H), 5.30 (s, 2H), 4.26-4.10 (m, 2H), 3.78 (s, 3H). LCMS (Method 4): Rt 1.37 min., m/z 447.1 [M+H]+.

Example 21—4-((6-chloro-7-(2-hydroxy-3-morpholinopropoxy)-2-oxo-1,2-dihydroquinolin-3-yl)methylamino)-2-methoxybenzonitrile (I-59)

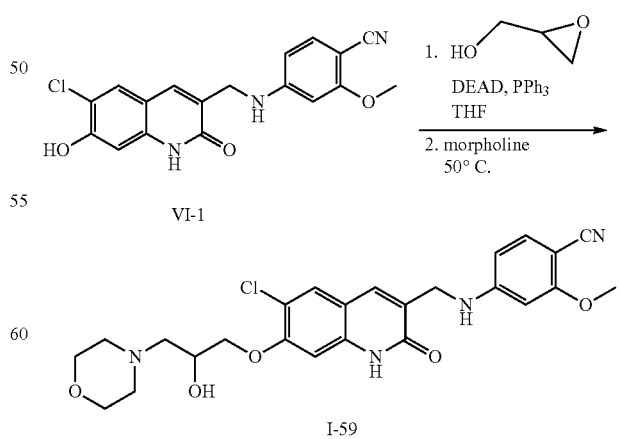

A solution of 4-((6-chloro-7-hydroxy-2-oxo-1,2-dihydroquinolin-3-yl)methylamino)-2-methoxybenzonitrile VI-1

(99.8 mg, 0.281 mmol) and triphenylphosphine (81.8 mg, 0.312 mmol) in THF (6.5 ml) was treated with DEAD (50.0 µl, 0.316 mmol) and stirred 10 minutes. Glycidol (20.7 µl, 0.310 mmol) was added and the solution was stirred overnight. Morpholine (28.0 µl, 0.321 mmol) was added and the solution was stirred at room temperature three hours, then shaken at 50° C. overnight. LCMS showed slow progress. More morpholine (20.0 µL) was added and the solution was shaken at 50° C. for 4.5 days. The solution was treated with silica gel and concentrated under reduced pressure. The material was chromatographed by Biotage MPLC (10 g silica gel column) with 0 to 10% MeOH in DCM, with isocratic elution when peaks came off. The material thus obtained was reabsorbed onto silica gel and rechromatographed with 0 to 32% B in DCM, where B=20% (7M ammonia in MeOH) in DCM, to provide the title compound (I-59) (54.1 mg, 0.099 mmol, 35% yield, HPLC purity 90% at 220 nm). $^1$H NMR (300 MHz, DMSO-$d_6$) δ ppm 11.88 (s, 1H), 7.80 (s, 1H), 7.67 (s, 1H), 7.29 (d, J=8.50 Hz, 1H), 7.16 (dd, J=5.70, 5.70 Hz, 1H), 6.95 (s, 1H), 6.31 (s, 1H), 6.22 (d, J=8.80 Hz, 1H), 4.99 (d, J=4.40 Hz, 1H), 4.19 (br d, J=5.60 Hz, 2H), 3.89-4.11 (m, 4H), 3.78 (s, 3H), 3.55 (m, 4H), 2.53-2.60 (m, 2H), 2.35-2.47 (m, 3H). LCMS (Method 4): Rt 0.91 min., m/z 499.2 [M+H]$^+$.

Example 22—4-((6-chloro-7-(2-morpholinoethoxy)-2-oxo-1,2-dihydroquinolin-3-yl)methyl amino)-2-methoxybenzonitrile (I-60)

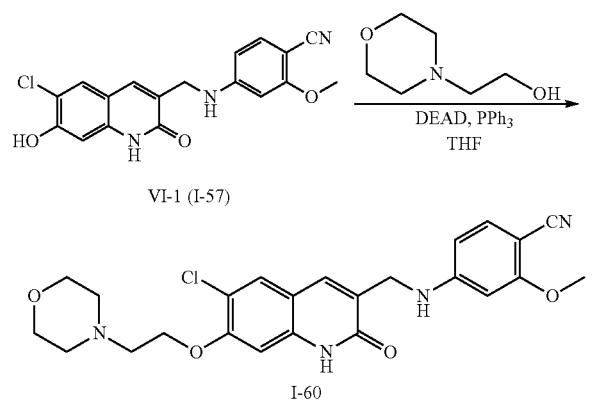

A solution of 4-((6-chloro-7-hydroxy-2-oxo-1,2-dihydroquinolin-3-yl)methylamino)-2-methoxybenzonitrile VI-1 (70.6 mg, 0.198 mmol), triphenylphosphine (78.5 mg, 0.299 mmol), and 2-morpholinoethanol (26.2 µl, 0.216 mmol) in THF (4.5 ml) was treated with DEAD (46.8 µl, 0.296 mmol) and stirred at room temperature overnight. Silica gel was added and the mixture was evaporated under reduced pressure. The residue was chromatographed by Biotage MPLC (10 g silica gel column, 0 to 10% MeOH in DCM, with isocratic elution at 6% MeOH). The material thus obtained was reabsorbed onto silica gel and rechromatographed with 0 to 100% B in DCM, where B=20% (7M ammonia in methanol) in DCM, with isocratic elution when peaks came off to provide the title compound (I-60) (48.5 mg, 0.103 mmol, 52% yield, HPLC purity 91% at 220 nm) as an off-white solid. $^1$H NMR (300 MHz, DMSO-$d_6$) δ ppm 11.91 (s, 1H), 7.81 (s, 1H), 7.68 (s, 1H), 7.29 (d, J=8.50 Hz, 1H), 7.16 (dd, J=6.00, 6.00 Hz, 1H), 6.95 (s, 1H), 6.32 (s, 1H), 6.22 (m, 1H), 4.20 (m, J=5.00 Hz, 4H), 3.78 (s, 3H), 3.65-3.51 (m, 4H), 2.77 (br s, 2H). LCMS (Method 4): Rt 0.94 min., m/z 469.1 [M+H]$^+$.

Example 23—4-(((6-chloro-7-(2-(dimethylamino)ethoxy)-2-oxo-1,2-dihydroquinolin-3-yl)methyl)amino)-2-methoxybenzonitrile (I-61)

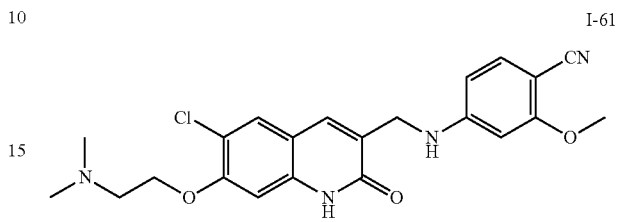

The title compound (I-61) was prepared using the method similar to one described for the preparation of I-60, except using 2-(dimethylamino)ethanol (35 mg, 42% yield), $^1$H NMR (300 MHz, DMSO-$d_6$): δ ppm 11.90 (s, 1H), 7.80 (s, 1H), 7.67 (s, 1H), 7.29 (d, J=8.50 Hz, 1H), 7.16 (dd, J=6.00, 6.00 Hz, 1H), 6.95 (s, 1H), 6.32 (s, 1H), 6.22 (d, J=8.50 Hz, 1H), 4.19 (d, J=5.60 Hz, 2H), 4.13 (dd, J=5.60 Hz, 2H), 3.78 (s, 3H), 2.71 (dd, J=5.40 Hz, 2H), 2.25 (s, 6H). LCMS (Method 4): Rt 0.91 min., m/z 427.2 [M+H]$^+$.

Protocol for Mitsunobu Library

Example 24—4-(((6-chloro-2-oxo-7-(pyridin-3-ylmethoxy)-1,2-dihydroquinolin-3-yl)methyl)amino)-2-methoxybenzonitrile (I-62)

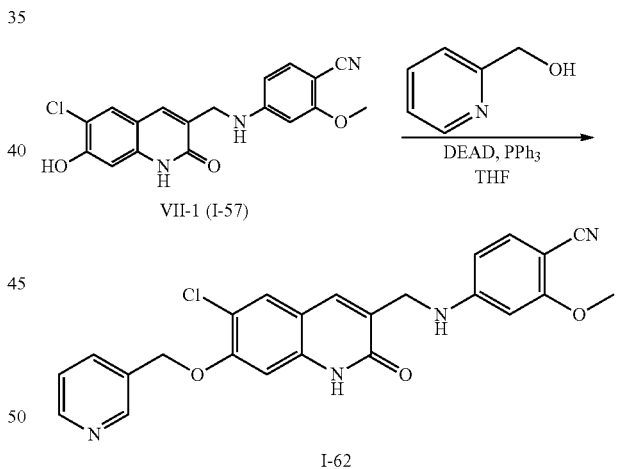

In a 1.5 mL vial are combined 4-(((6-chloro-7-hydroxy-2-oxo-1,2-dihydroquinolin-3-yl)methyl)amino)-2-methoxybenzonitrile VI-1 (150 µL, 0.030 mmol), pyridin-3-ylmethanol (165 µL, 0.033 mmol), and triphenylphosphine (180 µL, 0.036 mmol) in fresh, dry THF to give a light yellow solution. The vial was flushed with $N_2$. (E)-diisopropyl diazene-1,2-dicarboxylate (180 µL, 0.036 mmol) in fresh THF was added. The vial was quickly capped and heated for 2 hours at 50° C. LCMS shows that the triphenylphosphine has been consumed but there is still unreacted VI-1 present. More triphenylphosphine (180 µL, 0.036 mmol) and (E)-diisopropyl diazene-1,2-dicarboxylate (180 µL, 0.036 mmol) in fresh THF were added. The vial was flushed with $N_2$ and capped. The reaction was heated overnight at 50° C.

LCMS showed that the VI-1 has been consumed. The reaction was dried down under N$_2$. The residue was partitioned between 0.5 mL of 1N NaOH and 0.5 mL of EtOAc. The EtOAc was separated and combined with a second extract. The extracts were dried under N$_2$. The residue was dissolved in 500 uL of DMSO and submitted for mass-triggered prep HPLC purification. This yielded the desired product (I-62) (3.7 mg, 28% yield). LCMS (Method 4): Rt 1.24 min, m/z 447.05 [M+H]$^+$.

TABLE 7

The compounds listed in Table 7 were prepared using methods similar to the ones described for the preparation of 1-58-1-60 and 1-62.

TABLE 7-continued

The compounds listed in Table 7 were prepared using methods similar to the ones described for the preparation of 1-58-1-60 and 1-62.

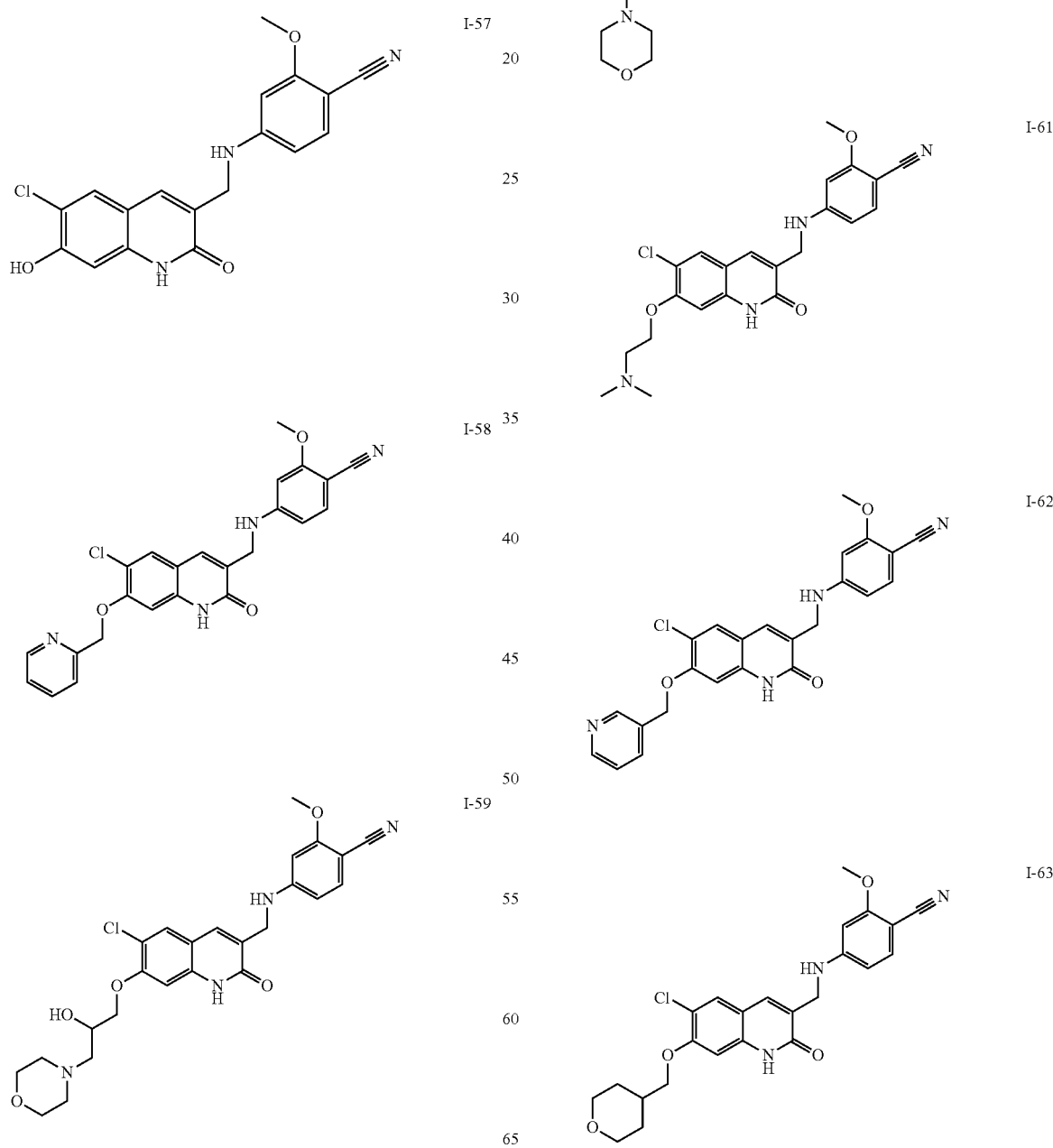

TABLE 7-continued
The compounds listed in Table 7 were prepared using methods similar to the ones described for the preparation of 1-58-1-60 and 1-62.
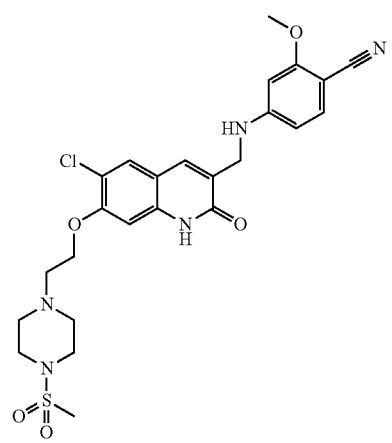 [SMILES: COc1cc(NCc2cc3cc(Cl)c(OCCN4CCN(S(C)(=O)=O)CC4)cc3[nH]c2=O)ccc1C#N]
I-64
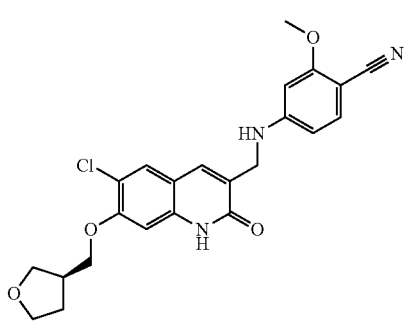 [SMILES: COc1cc(NCc2cc3cc(Cl)c(OC[C@H]4CCOC4)cc3[nH]c2=O)ccc1C#N]
I-65
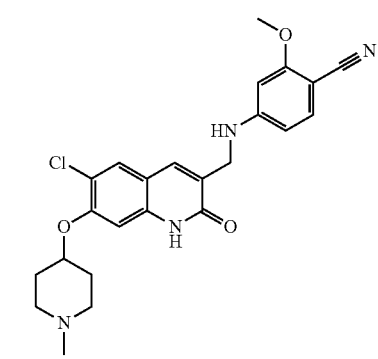 [SMILES: COc1cc(NCc2cc3cc(Cl)c(OC4CCN(C)CC4)cc3[nH]c2=O)ccc1C#N]
I-66
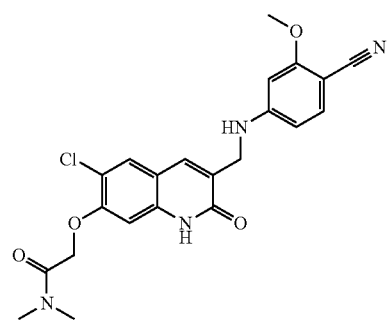 [SMILES: COc1cc(NCc2cc3cc(Cl)c(OCC(=O)N(C)C)cc3[nH]c2=O)ccc1C#N]
I-67
TABLE 7-continued
The compounds listed in Table 7 were prepared using methods similar to the ones described for the preparation of 1-58-1-60 and 1-62.
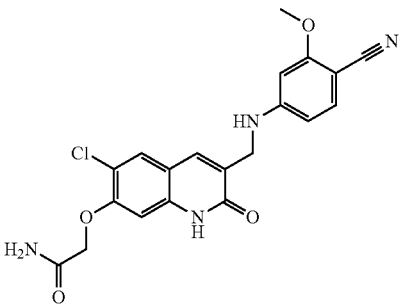 [SMILES: COc1cc(NCc2cc3cc(Cl)c(OCC(N)=O)cc3[nH]c2=O)ccc1C#N]
I-68
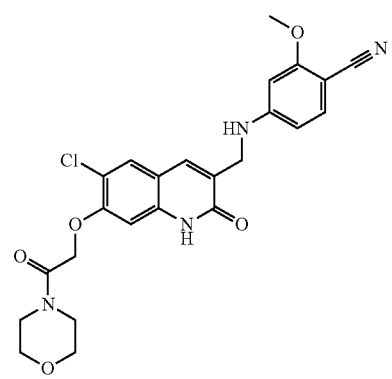 [SMILES: COc1cc(NCc2cc3cc(Cl)c(OCC(=O)N4CCOCC4)cc3[nH]c2=O)ccc1C#N]
I-69
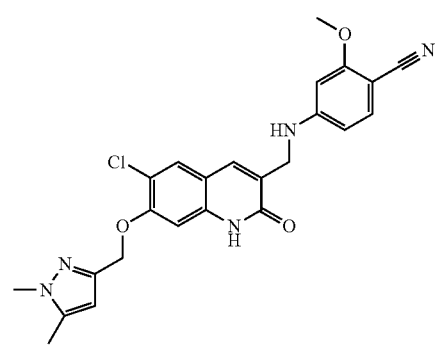 [SMILES: COc1cc(NCc2cc3cc(Cl)c(OCc4cc(C)n(C)n4)cc3[nH]c2=O)ccc1C#N]
I-70
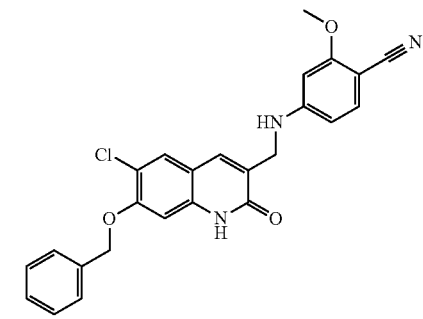 [SMILES: COc1cc(NCc2cc3cc(Cl)c(OCc4ccccc4)cc3[nH]c2=O)ccc1C#N]
I-71

TABLE 7-continued
The compounds listed in Table 7 were prepared using methods similar to the ones described for the preparation of 1-58-1-60 and 1-62.
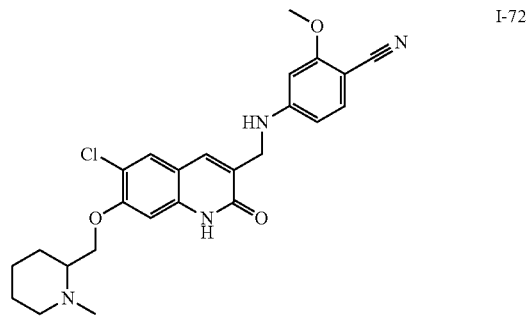
I-72
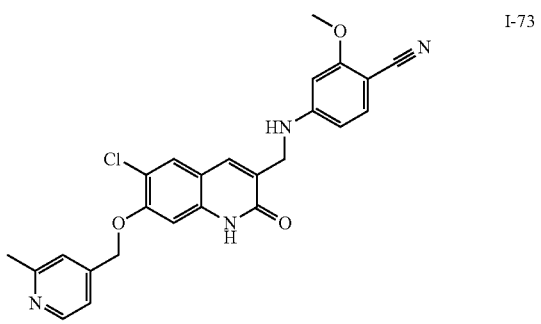
I-73
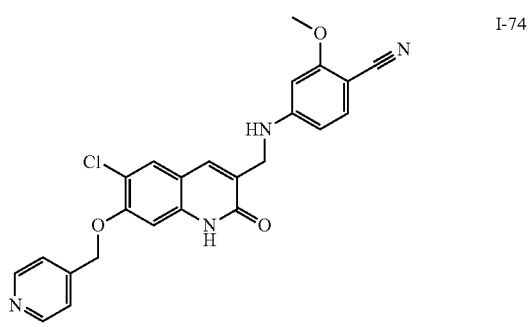
I-74
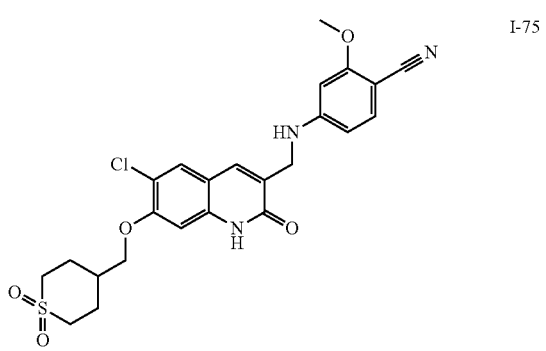
I-75
TABLE 7-continued
The compounds listed in Table 7 were prepared using methods similar to the ones described for the preparation of 1-58-1-60 and 1-62.
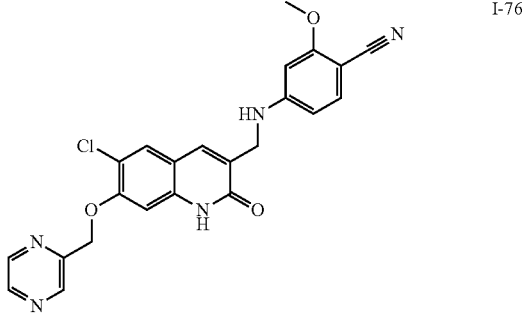
I-76
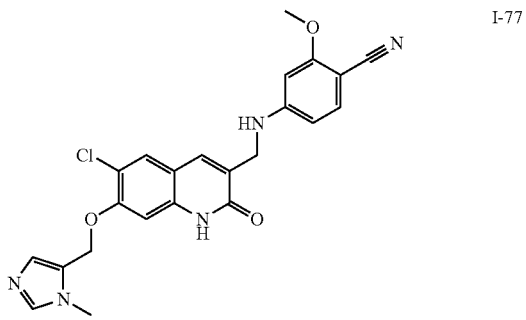
I-77
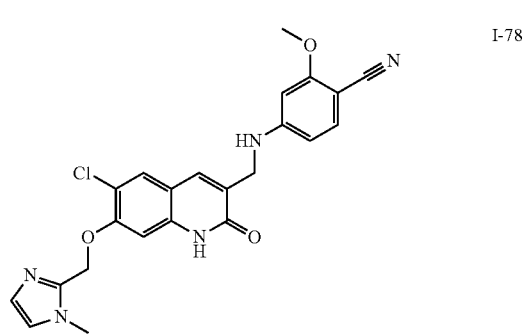
I-78
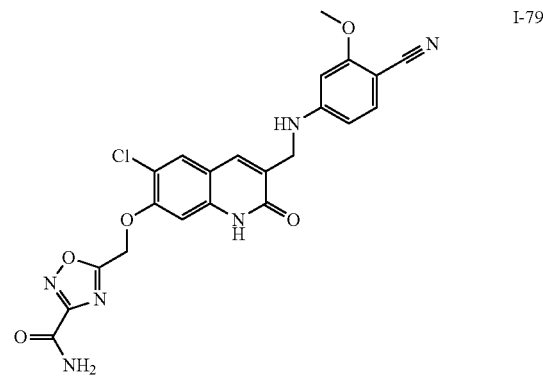
I-79

TABLE 7-continued
The compounds listed in Table 7 were prepared using methods similar to the ones described for the preparation of 1-58-1-60 and 1-62.
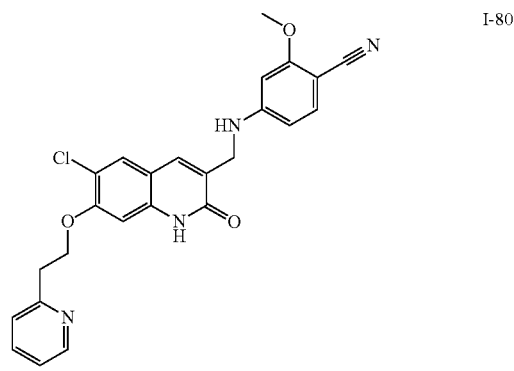
I-80
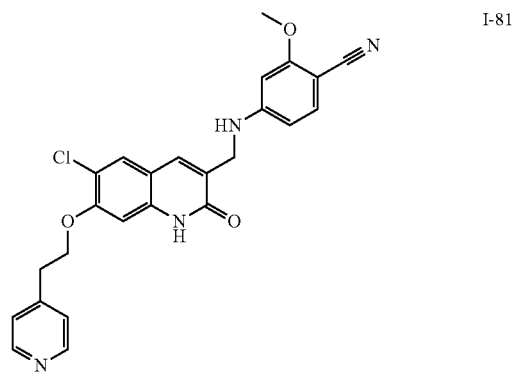
I-81
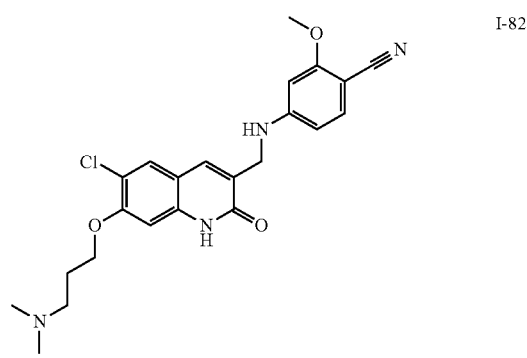
I-82
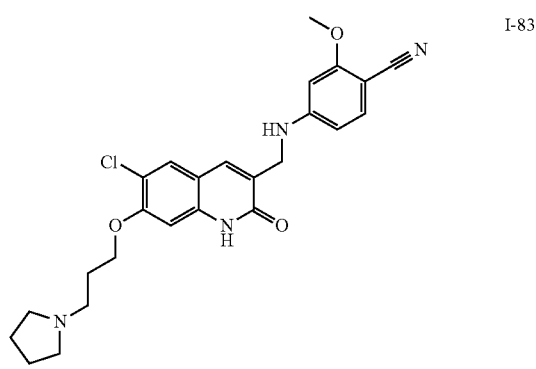
I-83
TABLE 7-continued
The compounds listed in Table 7 were prepared using methods similar to the ones described for the preparation of 1-58-1-60 and 1-62.
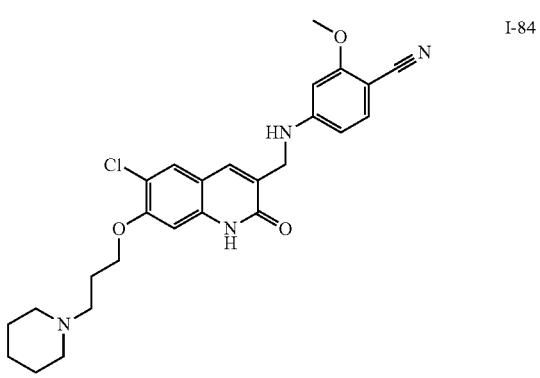
I-84
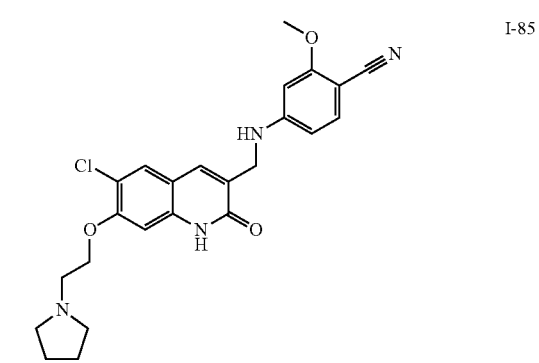
I-85
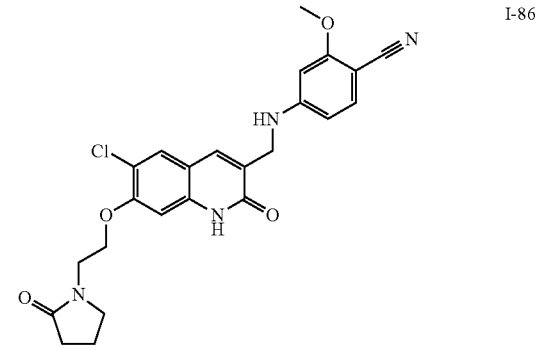
I-86
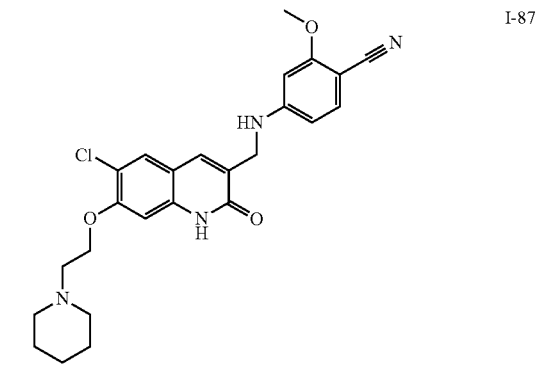
I-87

TABLE 7-continued
The compounds listed in Table 7 were prepared using methods similar to the ones described for the preparation of 1-58-1-60 and 1-62.
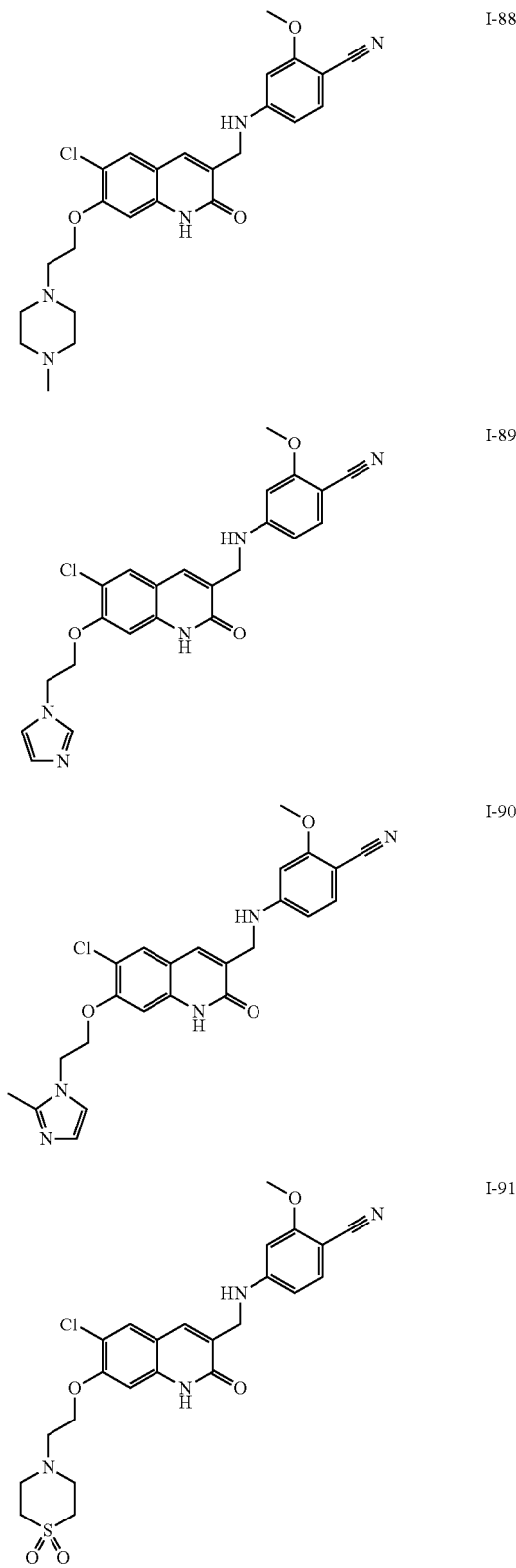
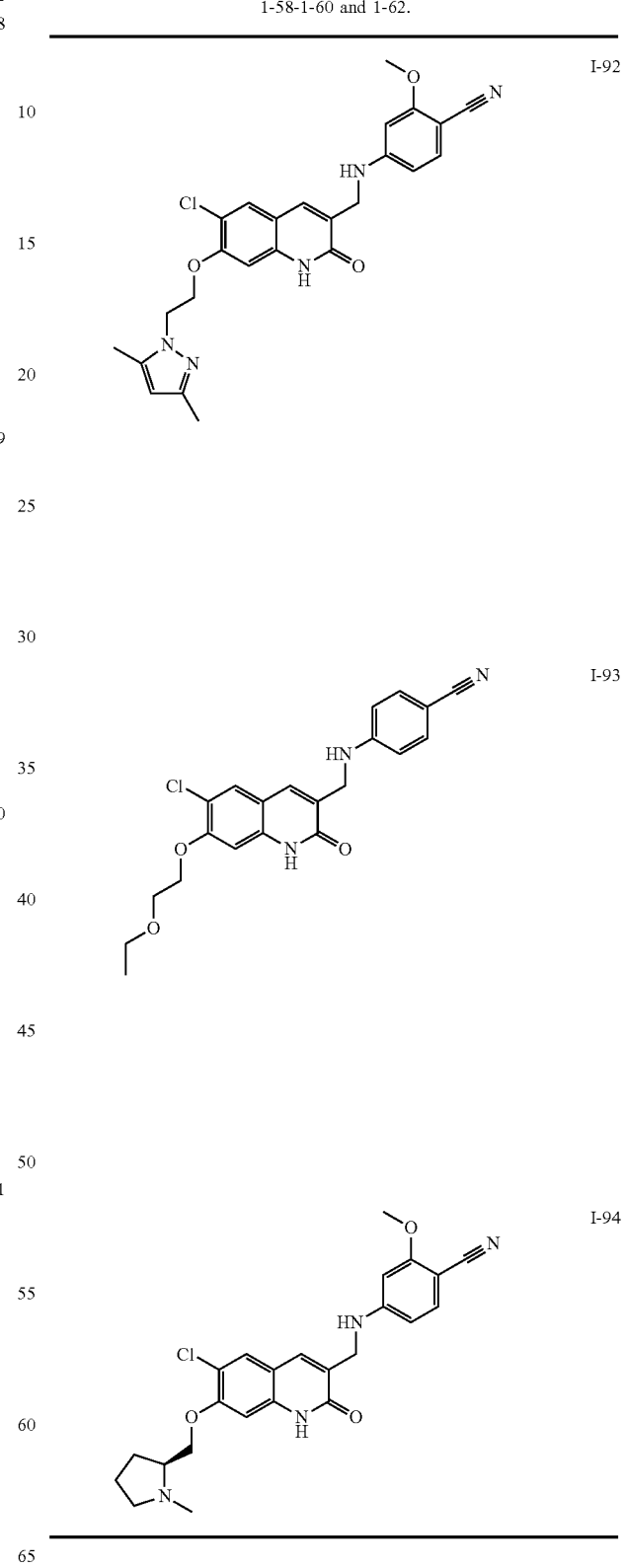

TABLE 8

LCMS signal and chemical names of each compound listed in Table 7

| Cmpd No | LCMS[a] | Chemical Name |
|---|---|---|
| I-57 | m/z: 356.09 (M + H)+<br>Rt (min): 1.17 | 4-{[(6-chloro-7-hydroxy-2-oxo-1,2-dihydroquinolin-3-yl)methyl]amino}-2-methoxybenzonitrile |
| I-58 | m/z: 447.07 (M + H)+<br>Rt (min): 1.37 | 4-({[6-chloro-2-oxo-7-(pyridin-2-ylmethoxy)-1,2-dihydroquinolin-3-yl]methyl}amino)-2-methoxybenzonitrile |
| I-59 | m/z: 499.16 (M + H)+<br>Rt (min): 0.91 | 4-[({6-chloro-7-[2-hydroxy-3-(morpholin-4-yl)propoxy]-2-oxo-1,2-dihydroquinolin-3-yl}methyl)amino]-2-methoxybenzonitrile |
| I-60 | m/z: 469.12 (M + H)+<br>Rt (min): 0.94 | 4-[({6-chloro-7-[2-(morpholin-4-yl)ethoxy]-2-oxo-1,2-dihydroquinolin-3-yl}methyl)amino]-2-methoxybenzonitrile |
| I-61 | m/z: 427.15 (M + H)+<br>Rt (min): 0.91 | 4-[({6-chloro-7-[2-(dimethylamino)ethoxy]-2-oxo-1,2-dihydroquinolin-3-yl}methyl)amino]-2-methoxybenzonitrile |
| I-62 | m/z: 447.05 (M + H)+<br>Rt (min): 1.23 | 4-({[6-chloro-2-oxo-7-(pyridin-3-ylmethoxy)-1,2-dihydroquinolin-3-yl]methyl}amino)-2-methoxybenzonitrile |
| I-63 | m/z: 454.09 (M + H)+<br>Rt (min): 1.42 | 4-({[6-chloro-7-(oxan-4-ylmethoxy)-2-oxo-1,2-dihydroquinolin-3-yl]methyl}amino)-2-methoxybenzonitrile |
| I-64 | m/z: 546.07 (M + H)+<br>Rt (min): 1.05 | 4-[({6-chloro-7-[2-(4-methanesulfonylpiperazin-1-yl)ethoxy]-2-oxo-1,2-dihydroquinolin-3-yl}methyl)amino]-2-methoxybenzonitrile |
| I-65 | m/z: 440.11 (M + H)+<br>Rt (min): 1.36 | 4-[({6-chloro-2-oxo-7-[(3S)-oxolan-3-ylmethoxy]-1,2-dihydroquinolin-3-yl}methyl)amino]-2-methoxybenzonitrile |
| I-66 | m/z: 453.14 (M + H)+<br>Rt (min): 0.97 | 4-[({6-chloro-7-[(1-methylpiperidin-4-yl)oxy]-2-oxo-1,2-dihydroquinolin-3-yl}methyl)amino]-2-methoxybenzonitrile |
| I-67 | m/z: 441.12 (M + H)+<br>Rt (min): 1.16 | 2-[(6-chloro-3-{[(4-cyano-3-methoxyphenyl)amino]methyl}-2-oxo-1,2-dihydroquinolin-7-yl)oxy]-N,N-dimethylacetamide |
| I-68 | m/z: 413.09 (M + H)+<br>Rt (min): 1.09 | 2-[(6-chloro-3-{[(4-cyano-3-methoxyphenyl)amino]methyl}-2-oxo-1,2-dihydroquinolin-7-yl)oxy]acetamide |
| I-69 | m/z: 483.13 (M + H)+<br>Rt (min): 1.17 | 4-[({6-chloro-7-[2-(morpholin-4-yl)-2-oxoethoxy]-2-oxo-1,2-dihydroquinolin-3-yl}methyl)amino]-2-methoxybenzonitrile |
| I-70 | m/z: 464.03 (M + H)+<br>Rt (min): 1.32 | 4-[({6-chloro-7-[(1,5-dimethyl-1H-pyrazol-3-yl)methoxy]-2-oxo-1,2-dihydroquinolin-3-yl}methyl)amino]-2-methoxybenzonitrile |
| I-71 | m/z: 446.02 (M + H)+<br>Rt (min): 1.6 | 4-({[7-(benzyloxy)-6-chloro-2-oxo-1,2-dihydroquinolin-3-yl]methyl}amino)-2-methoxybenzonitrile |
| I-72 | m/z: 467.10 (M + H)+<br>Rt (min): 0.98 | 4-[({6-chloro-7-[(1-methylpiperidin-2-yl)methoxy]-2-oxo-1,2-dihydroquinolin-3-yl}methyl)amino]-2-methoxybenzonitrile |
| I-73 | m/z: 461.12 (M + H)+<br>Rt (min): 1.04 | 4-[({6-chloro-7-[(2-methylpyridin-4-yl)methoxy]-2-oxo-1,2-dihydroquinolin-3-yl}methyl)amino]-2-methoxybenzonitrile |
| I-74 | m/z: 447.08 (M + H)+<br>Rt (min): 1.13 | 4-({[6-chloro-2-oxo-7-(pyridin-4-ylmethoxy)-1,2-dihydroquinolin-3-yl]methyl}amino)-2-methoxybenzonitrile |
| I-75 | m/z: 502.03 (M + H)+<br>Rt (min): 1.25 | 4-[({6-chloro-7-[(1,1-dioxo-1$\lambda^6$-thian-4-yl)methoxy]-2-oxo-1,2-dihydroquinolin-3-yl}methyl)amino]-2-methoxybenzonitrile |
| I-76 | m/z: 447.97 (M + H)+<br>Rt (min): 1.22 | 4-({[6-chloro-2-oxo-7-(pyrazin-2-ylmethoxy)-1,2-dihydroquinolin-3-yl]methyl}amino)-2-methoxybenzonitrile |
| I-77 | m/z: 450.08 (M + H)+<br>Rt (min): 0.98 | 4-[({6-chloro-7-[(1-methyl-1H-imidazol-5-yl)methoxy]-2-oxo-1,2-dihydroquinolin-3-yl}methyl)amino]-2-methoxybenzonitrile |
| I-78 | m/z: 450.08 (M + H)+<br>Rt (min): 1.03 | 4-[({6-chloro-7-[(1-methyl-1H-imidazol-2-yl)methoxy]-2-oxo-1,2-dihydroquinolin-3-yl}methyl)amino]-2-methoxybenzonitrile |
| I-79 | m/z: 480.99 (M + H)+<br>Rt (min): 1.14 | 5-{[(6-chloro-3-{[(4-cyano-3-methoxyphenyl)amino]methyl}-2-oxo-1,2-dihydroquinolin-7-yl)oxy]methyl}-1,2,4-oxadiazole-3-carboxamide |
| I-80 | m/z: 461.03 (M + H)+<br>Rt (min): 1.21 | 4-[({6-chloro-2-oxo-7-[2-(pyridin-2-yl)ethoxy]-1,2-dihydroquinolin-3-yl}methyl)amino]-2-methoxybenzonitrile |
| I-81 | m/z: 461.13 (M + H)+<br>Rt (min): 1.18 | 4-[({6-chloro-2-oxo-7-[2-(pyridin-4-yl)ethoxy]-1,2-dihydroquinolin-3-yl}methyl)amino]-2-methoxybenzonitrile |

TABLE 8-continued

LCMS signal and chemical names of each compound listed in Table 7

| Cmpd No | LCMS[a] | Chemical Name |
|---|---|---|
| I-82 | m/z: 441.10 (M + H)+<br>Rt (min): 0.96 | 4-[({6-chloro-7-[3-(dimethylamino)propoxy]-2-oxo-1,2-dihydroquinolin-3-yl}methyl)amino]-2-methoxybenzonitrile |
| I-83 | m/z: 467.17 (M + H)+<br>Rt (min): 1.01 | 4-[({6-chloro-2-oxo-7-[3-(pyrrolidin-1-yl)propoxy]-1,2-dihydroquinolin-3-yl}methyl)amino]-2-methoxybenzonitrile |
| I-84 | m/z: 481.16 (M + H)+<br>Rt (min): 1.05 | 4-[({6-chloro-2-oxo-7-[3-(piperidin-1-yl)propoxy]-1,2-dihydroquinolin-3-yl}methyl)amino]-2-methoxybenzonitrile |
| I-85 | m/z: 453.13 (M + H)+<br>Rt (min): 0.98 | 4-[({6-chloro-2-oxo-7-[2-(pyrrolidin-1-yl)ethoxy]-1,2-dihydroquinolin-3-yl}methyl)amino]-2-methoxybenzonitrile |
| I-86 | m/z: 467.04 (M + H)+<br>Rt (min): 1.24 | 4-[({6-chloro-2-oxo-7-[2-(2-oxopyrrolidin-1-yl)ethoxy]-1,2-dihydroquinolin-3-yl}methyl)amino]-2-methoxybenzonitrile |
| I-87 | m/z: 467.14 (M + H)+<br>Rt (min): 1.03 | 4-[({6-chloro-2-oxo-7-[2-(piperidin-1-yl)ethoxy]-1,2-dihydroquinolin-3-yl}methyl)amino]-2-methoxybenzonitrile |
| I-88 | m/z: 482.16 (M + H)+<br>Rt (min): 0.95 | 4-[({6-chloro-7-[2-(4-methylpiperazin-1-yl)ethoxy]-2-oxo-1,2-dihydroquinolin-3-yl}methyl)amino]-2-methoxybenzonitrile |
| I-89 | m/z: 450.11 (M + H)+<br>Rt (min): 0.94 | 4-[({6-chloro-7-[2-(1H-imidazol-1-yl)ethoxy]-2-oxo-1,2-dihydroquinolin-3-yl}methyl)amino]-2-methoxybenzonitrile |
| I-90 | m/z: 464.13 (M + H)+<br>Rt (min): 0.96 | 4-[({6-chloro-7-[2-(2-methyl-1H-imidazol-1-yl)ethoxy]-2-oxo-1,2-dihydroquinolin-3-yl}methyl)amino]-2-methoxybenzonitrile |
| I-91 | m/z: 517.04 (M + H)+<br>Rt (min): 1.2 | 4-[({6-chloro-7-[2-(1,1-dioxo-1$\lambda^6$,4-thiomorpholin-4-yl)ethoxy]-2-oxo-1,2-dihydroquinolin-3-yl}methyl)amino]-2-methoxybenzonitrile |
| I-92 | m/z: 478.12 (M + H)+<br>Rt (min): 1.42 | 4-[({6-chloro-7-[2-(3,5-dimethyl-1H-pyrazol-1-yl)ethoxy]-2-oxo-1,2-dihydroquinolin-3-yl}methyl)amino]-2-methoxybenzonitrile |
| I-93 | m/z: 428.11 (M + H)+<br>Rt (min): 1.42 | 4-({[6-chloro-7-(2-ethoxyethoxy)-2-oxo-1,2-dihydroquinolin-3-yl]methyl}amino)-2-methoxybenzonitrile |
| I-94 | m/z: 453.13 (M + H)+<br>Rt (min): 0.96 | 4-{[(6-chloro-7-{[(2S)-1-methylpyrrolidin-2-yl]methoxy}-2-oxo-1,2-dihydroquinolin-3-yl)methyl]amino}-2-methoxybenzonitrile |

[a]LCMS data are determined by Method 4.

Example 25—4-((6-chloro-8-methyl-2-oxo-1,2-dihydroquinolin-3-yl)methylamino)-2-methoxybenzonitrile (I-95)

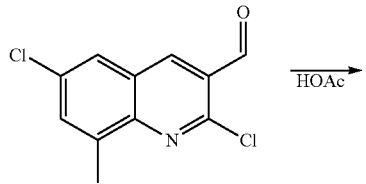

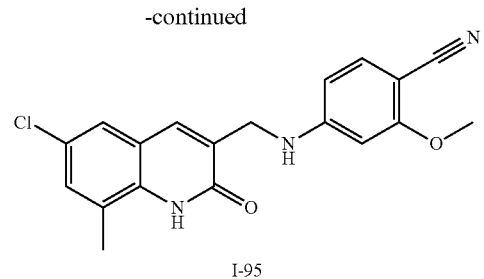

I-95

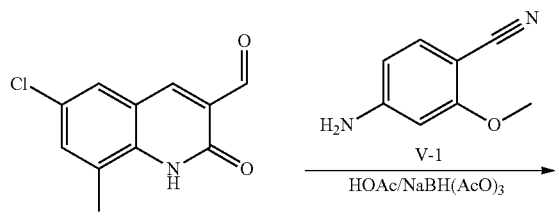

Step-1: 6-chloro-8-methyl-2-oxo-1,2-dihydroquinoline-3-carbaldehyde

A suspension of 2,6-dichloro-8-methylquinoline-3-carbaldehyde (0.25 g, 1.041 mmol) in AcOH (10.41 ml) was heated to 110° C. for 3 h then at 100° C. for 16 h. The reaction mixture was cooled down to 0° C. The yellow precipitate was filtered off and washed with water to give 6-chloro-8-methyl-2-oxo-1,2-dihydroquinoline-3-carbaldehyde (0.152 g, 0.686 mmol, 65.9% yield). The crude material was used in the next step without further purification.

Step-2: 4-(((6-chloro-8-methyl-2-oxo-1,2-dihydro-quinolin-3-yl)methyl)amino)-2-methoxy benzonitrile (I-95)

To a mixture of 6-chloro-8-methyl-2-oxo-1,2-dihydroquinoline-3-carbaldehyde (0.152 g, 0.686 mmol), 4-amino-2-methoxybenzonitrile (0.122 g, 0.823 mmol) and acetic acid (0.196 ml, 3.43 mmol) in DCM (12.25 ml) was added sodium triacetoxyborohydride (0.189 g, 0.892 mmol). The reaction mixture was stirred at room temperature for 16 h. Water (20 mL) was added to the reaction mixture and the product was extracted into EtOAc (3×25 mL). The combined organic extracts were dried over MgSO$_4$. The crude material was purified by reverse phase preparative HPLC (20 mL/min, 10 min gradient 15%-85% AcCN, 0.01% HCO2H on an XTerra Prep MS C18 OBD 5 μm, 19×100 mm column) to yield 4-((6-chloro-8-methyl-2-oxo-1,2-dihydro quinolin-3-yl)methylamino)-2-methoxybenzonitrile (I-95) (7.3 mg, 0.021 mmol, 3.0% yield). $^1$H NMR (300 MHz, DMSO-d$_6$) δ ppm 11.24 (s, 1H), 7.71 (s, 1H), 7.62 (d, J=2.05 Hz, 1H), 7.37 (d, J=2.05 Hz, 1H), 7.27 (d, J=8.50 Hz, 1H), 7.23-7.14 (m, 1H), 6.30 (br d, J=1.47 Hz, 1H), 6.26-6.15 (m, 1H), 4.26-4.20 (m, 2H), 3.76 (s, 2H), 2.40 (s, 3H). Rt 1.42 min, m/z 354.10 [M+H]$^+$.

Example 26—4-((6-chloro-8-methoxy-2-oxo-1,2-dihydroquinolin-3-yl)methylamino)-2-methoxybenzonitrile (I-97)

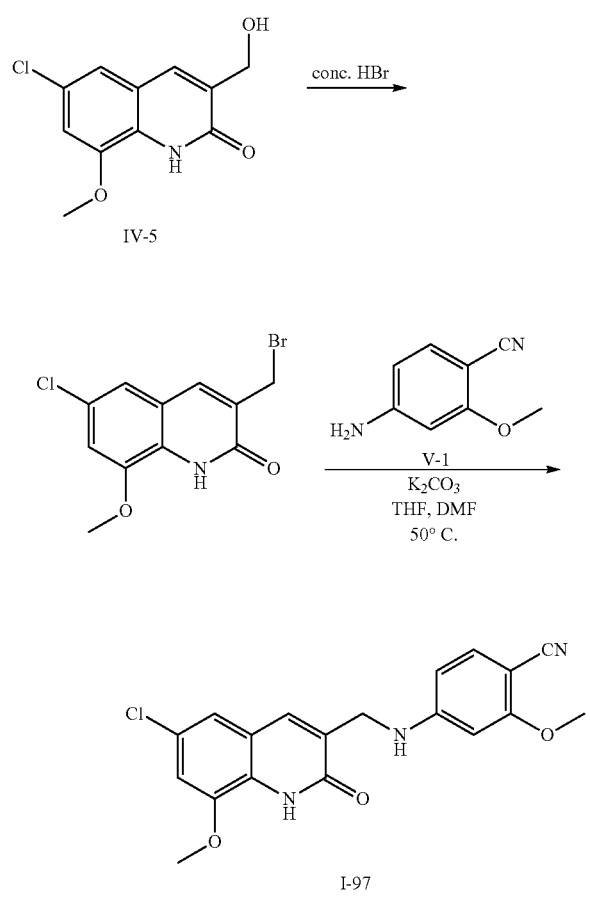

Step 1: 3-(bromomethyl)-6-chloro-8-methoxyquinolin-2(1H)-one

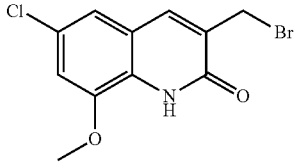 [SMILES: COc1cc(Cl)cc2cc(CBr)c(=O)[nH]c12]

6-Chloro-3-(hydroxymethyl)-8-methoxyquinolin-2(1H)-one IV-5 (239.3 mg, 0.999 mmol) was treated with 48% hydrobromic acid (10.0 mL, 87 mmol) and stirred at 100° C., resulting in precipitation. LCMS at 40 minutes showed an 85:15 ratio of product to starting material. At 1.5 hours, the reaction was allowed to cool. The mixture was poured into water (150 mL). The tan precipitate was collected on a Buchner funnel and washed with water (250 mL). The filter cake was suspended in a few milliliters of heptane, then the heptane was removed by evaporation under reduced pressure to provide 3-(bromomethyl)-6-chloro-8-methoxyquinolin-2(1H)-one, contaminated with ~10% alcohol starting material. The material was dried further by addition of EtOAc and heptane and evaporation under reduced pressure to provide a cream-colored solid (285.6 mg, 0.944 mmol, 86% yield). $^1$H NMR (300 MHz, DMSO-d$_6$): δ ppm 11.39 (s, 1H), 8.10 (s, 1H), 7.38 (d, J=2.05 Hz, 1H), 7.22 (d, J=2.05 Hz, 1H), 4.56 (s, 2H), 3.92 (s, 3H). LCMS (Method 1): Rt 2.40 min., m/z 303.8 [M+H]$^+$.

Step 2: 4-((6-chloro-8-methoxy-2-oxo-1,2-dihydro-quinolin-3-yl)methylamino)-2-methoxybenzonitrile (I-97)

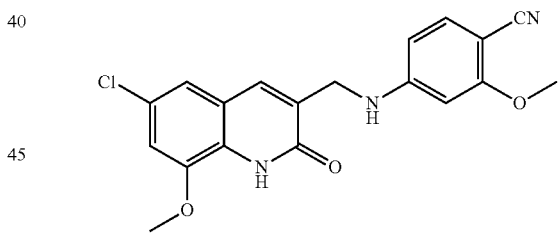

A suspension of 3-(bromomethyl)-6-chloro-8-methoxyquinolin-2(1H)-one (38.9 mg, 0.129 mmol), 4-amino-2-methoxybenzonitrile (21 mg, 0.142 mmol), and K$_2$CO$_3$ (35 mg, 0.253 mmol) in THF (1.5 ml) was stirred at 50° C. for 2.5 hours, during which most of the material went into solution. LCMS at 45 minutes showed no reaction. The solvent was evaporated under reduced pressure, then replaced with DMF (1.5 ml). The reaction was stirred at 50° C. overnight. LCMS showed product formation, and complete consumption of the bromide starting material. The solvent was evaporated under reduced pressure at 60° C. The residue was readily dissolved in a few mL DCM/MeOH, except for some residual material that appeared to be inorganic salts. The solution was removed from the solid by pipet, treated with silica gel, and evaporated under reduced pressure. The material was chromatographed by Biotage MPLC (10 g silica gel snap column, 0 to 100% EtOAc in hexanes, with isocratic elution at 93% EtOAc to provide the title compound (I-97) (19.3 mg, 0.051 mmol, 39.8% yield, HPLC purity >99% at 220 nm) as a slightly yellow solid. $^{1}$H NMR (300 MHz, DMSO-$d_6$): δ ppm 11.30 (s, 1H), 7.69 (s, 1H), 7.37 (d, J=2.05 Hz, 1H), 7.29 (d, J=8.50 Hz, 1H), 7.23-7.15 (m, 2H), 6.32 (m, 1H), 6.27-6.19 (m, 1H), 4.24 (d, J=5.90 Hz, 2H), 3.91 (s, 3H), 3.78 (s, 3H). LCMS (Method 4): Rt 1.37 min., m/z 370.0 [M+H]$^{+}$.

Example 27—4-((6-chloro-8-(2-morpholinoethoxy)-2-oxo-1,2-dihydroquinolin-3-yl)methyl amino)-2-methoxybenzonitrile (I-99)

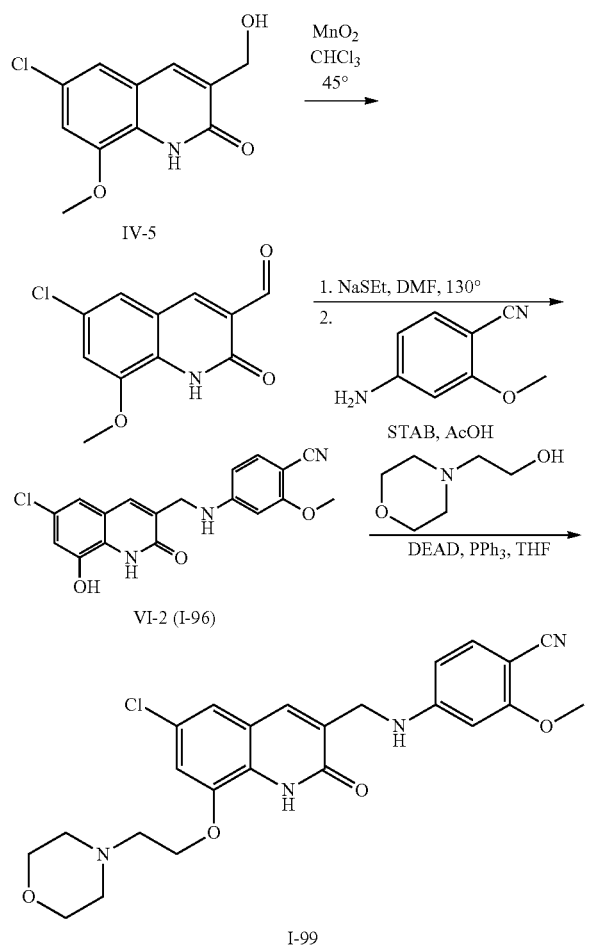

Step 1: 6-chloro-8-methoxy-2-oxo-1,2-dihydroquinoline-3-carbaldehyde

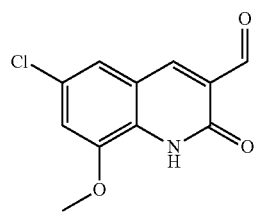

A suspension of 6-chloro-3-(hydroxymethyl)-8-methoxyquinolin-2(1H)-one "II-14" (479.2 mg, 2.000 mmol) and manganese dioxide (526.4 mg) in chloroform (20 ml) was stirred at 45° C. one day. More MnO$_2$ (438.2 mg) was added and the mixture was stirred further at 45° C. for 1.5 days, then at room temperature for 1 day. The mixture was diluted with 1:1 DCM-MeOH (100 mL), then filtered through Celite 545 on a Buchner funnel, and the filter cake was washed with more 1:1 DCM-MeOH. The filtrate was evaporated to provide impure 6-chloro-8-methoxy-2-oxo-1,2-dihydroquinoline-3-carbaldehyde (0.48 g, 2.020 mmol, 101% yield) as a yellow solid. The crude material was used without further purification. $^{1}$H NMR (300 MHz, DMSO-$d_6$): δ ppm 11.69 (br s, 1H), 10.23 (s, 1H), 8.44 (s, 1H), 7.62 (d, J=2.05 Hz, 1H), 7.32 (d, J=1.76 Hz, 1H), 3.93 (s, 3H). LCMS (Method 1): Rt 2.00 min., m/z 237.9 [M+H]$^{+}$.

Step 2: 4-((6-chloro-8-hydroxy-2-oxo-1,2-dihydroquinolin-3-yl)methylamino)-2-methoxybenzonitrile (I-96)

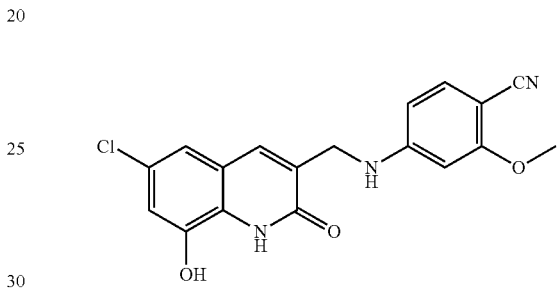

A suspension of 6-chloro-8-methoxy-2-oxo-1,2-dihydroquinoline-3-carbaldehyde (158.3 mg, 0.666 mmol) and sodium ethanethiolate (72.0 mg, 0.856 mmol) in DMF (1.6 ml) was heated at 130° C. with stirring. At 2 hours a spatula-tip more sodium ethanethiolate was added. LCMS at 3.25 hours indicated the reaction had gone to completion. The mixture was allowed to cool, then diluted with 3.6% HCl (aq, 3.2 mL). The solids were collected on a Hirsch funnel, washed with water (~25 mL) and air-dried on the funnel. The filter cake was treated with heptane (10 mL), evaporated under reduced pressure, then evaporated further under high vacuum at 60° C. to provide very impure 6-chloro-8-hydroxy-2-oxo-1,2-dihydroquinoline-3-carbaldehyde (109.1 mg, m/z 224 [M+H]$^{+}$) as a yellow solid. The sample was suspended with 4-amino-2-methoxybenzonitrile (100 mg, 0.675 mmol) in MeOH (7.5 mL) and DCM (2.0 mL). The mixture was treated with AcOH (27.2 µL) and stirred at room temperature 1.5 hours, then at 50° C. for 4 hours. Toluene (4 mL) was added, and the solvents were evaporated under reduced pressure. A second aliquot of toluene (4 mL) was added and then evaporated under reduced pressure. The residue was suspended in chloroform (7.5 mL) and treated with acetic acid (130.6 µl, 2.281 mmol). The mixture was stirred 5 minutes, then sodium triacetoxyborohydride (156.6 mg, 0.739 mmol) was added and the reaction was stirred at room temperature in the dark overnight. LCMS showed consumption of the aldehyde starting material. The mixture was diluted with EtOAc and MeOH, treated with silica gel, and evaporated under reduced pressure. The material was chromatographed by Biotage MPLC (10 g silica gel column, 0 to 5% MeOH in DCM, with isocratic elution when peaks came off) to provide 4-((6-chloro-8-hydroxy-2-oxo-1,2-dihydroquinolin-3-yl)methylamino)-2-methoxybenzonitrile I-96 (28.9 mg, 0.081 mmol, 12% yield) as a yellow solid. NMR chemical shifts are shown in the procedure for intermediate VI-2. LCMS (Method 1): Rt 2.26 min., m/z 355.9 [M+H]⁺.

Step 3: 4-((6-chloro-8-(2-morpholinoethoxy)-2-oxo-1,2-dihydroquinolin-3-yl)methylamino)-2-methoxy-benzonitrile (I-99)

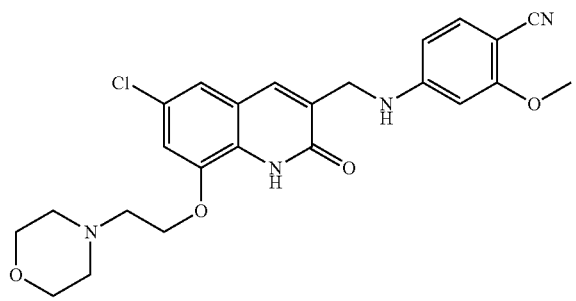 [SMILES: COc1cc(NCc2cc3cc(Cl)cc(OCCN4CCOCC4)c3[nH]c2=O)ccc1C#N]

A solution of 4-((6-chloro-8-hydroxy-2-oxo-1,2-dihydroquinolin-3-yl)methylamino)-2-methoxybenzonitrile VII-2 (27.6 mg, 0.078 mmol) and triphenylphosphine (30.5 mg, 0.116 mmol) in THF (1.8 mL) was treated with 103.0 μL of a solution of 10% (v/v) 2-morpholinoethanol in THF. The solution was treated with DEAD (18.6 μl, 0.117 mmol), placed under nitrogen, and stirred at room temperature overnight. LCMS showed the reaction had gone to completion. Silica gel was added and the mixture was evaporated under reduced pressure. The residue was chromatographed by Biotage MPLC (10 g silica gel column, 0 to 5% MeOH in DCM, with isocratic elution at 3% MeOH) to give impure product. The material was purified further by reverse phase preparative HPLC on Gilson to provide the title compound (I-99) (1.9 mg, 4.05 μmol, 5.2% yield) as a white solid. ¹H NMR (300 MHz, METHANOL-d₄): δ ppm 7.72 (s, 1H), 7.25 (d, J=8.50 Hz, 1H), 7.22-7.19 (m, 1H), 7.14-7.11 (m, 1H), 6.31-6.31 (m, 1H), 6.27-6.21 (m, 1H), 4.38-4.33 (m, 2H), 4.28 (dd, J=5.00, 5.00 Hz, 2H), 3.85-3.76 (m, 7H), 2.92 (dd, J=5.00, 5.00 Hz, 2H), 2.68-2.55 (m, 4H). LCMS (Method 4): Rt 1.05 min., m/z 469.1 [M+H]⁺.

TABLE 9

The compounds listed in Table 9 were prepared using methods similar to those described for the preparation of 1-95-1-97 and 99.

I-95

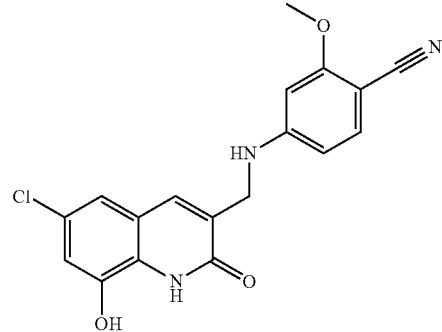 [SMILES: COc1cc(NCc2cc3cc(Cl)cc(O)c3[nH]c2=O)ccc1C#N]

TABLE 9-continued

The compounds listed in Table 9 were prepared using methods similar to those described for the preparation of 1-95-1-97 and 99.

I-96

I-97

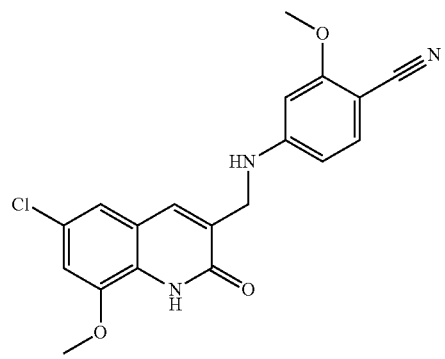 [SMILES: COc1cc(NCc2cc3cc(Cl)cc(OC)c3[nH]c2=O)ccc1C#N]

I-98

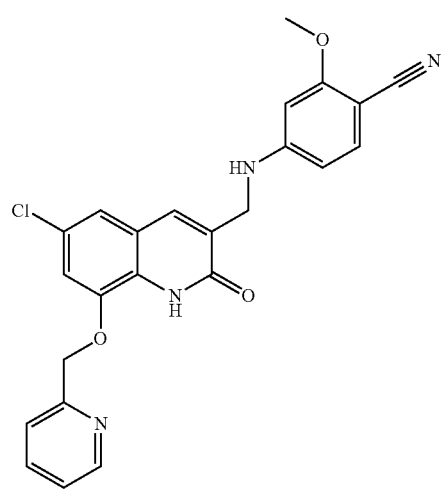 [SMILES: COc1cc(NCc2cc3cc(Cl)cc(OCc4ccccn4)c3[nH]c2=O)ccc1C#N]

TABLE 9-continued

The compounds listed in Table 9 were prepared using methods similar to those described for the preparation of 1-95-1-97 and 99.

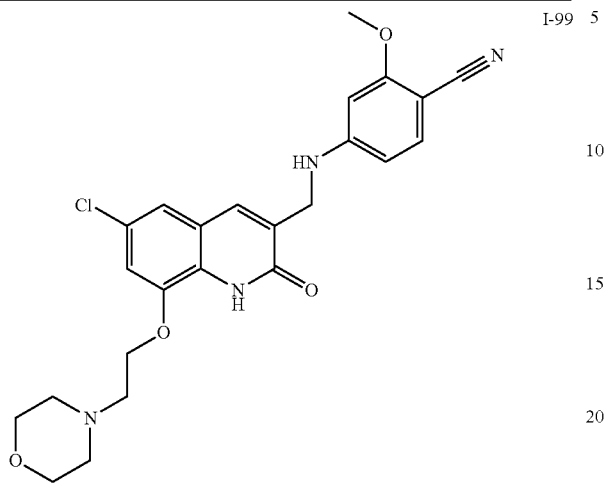

I-99

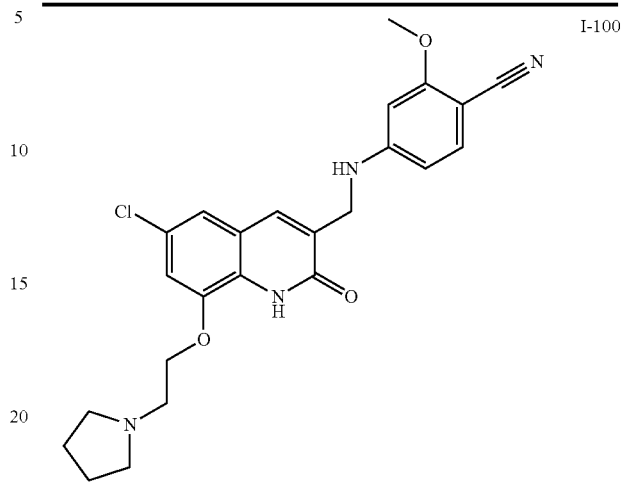

I-100

TABLE 10

LCMS signal and NMR chemical shifts of each compound listed in Table 9.

| Cmpd No | LCMS[a] | $^1$H NMR (300 MHz) δ ppm | Chemical Name |
|---|---|---|---|
| I-95 | m/z: 354.10 (M + H)+ Rt (min): 1.42 | $^1$H NMR (300 MHz, DMSO-d$_6$) δ ppm 11.24 (s, 1 H), 7.71 (s, 1 H), 7.62 (d, J = 2.05 Hz, 1 H), 7.37 (d, J = 2.05 Hz, 1 H), 7.27 (d, J = 8.50 Hz, 1 H), 7.23-7.14 (m, 1 H), 6.30 (br d, J = 1.47 Hz, 1 H), 6.15-6.26 (m, 1 H), 4.26-4.20 (m, 2 H), 3.76 (s, 2 H), 2.40 (s, 3 H) | 4-{[(6-chloro-8-methyl-2-oxo-1,2-dihydroquinolin-3-yl)methyl]amino}-2-methoxybenzonitrile |
| I-96 | m/z: 356.02 (M + H)+ Rt (min): 1.22 | 1H NMR (300 MHz, DMSO-d6): δ ppm 10.96 (br s, 2 H), 7.66 (s, 1 H), 7.29 (d, J = 8.50 Hz, 1 H), 7.24-7.14 (m, 2 H), 6.87 (d, J = 2.05 Hz, 1 H), 6.32 (s, 1 H), 6.27-6.18 (m, 1 H), 4.23 (d, J = 5.90 Hz, 2 H), 3.78 (s, 3 H). | 4-{[(6-chloro-8-hydroxy-2-oxo-1,2-dihydroquinolin-3-yl)methyl]amino}-2-methoxybenzonitrile |
| I-97 | m/z: 370.03 (M + H)+ Rt (min): 1.37 | 1H NMR (300 MHz, DMSO-d6): δ ppm 11.30 (s, 1 H), 7.69 (s, 1 H), 7.37 (d, J = 2.05 Hz, 1 H), 7.29 (d, J = 8.50 Hz, 1 H), 7.23-7.15 (m, 2 H), 6.32 (m, 1 H), 6.27-6.19 (m, 1 H), 4.24 (d, J = 5.90 Hz, 2 H), 3.91 (s, 3 H), 3.78 (s, 3 H). | 4-{[(6-chloro-8-methoxy-2-oxo-1,2-dihydroquinolin-3-yl)methyl]amino}-2-methoxybenzonitrile |
| I-98 | m/z: 447.03 (M + H)+ Rt (min): 1.38 | | 4-({[6-chloro-2-oxo-8-(pyridin-2-ylmethoxy)-1,2-dihydroquinolin-3-yl]methyl}amino)-2-methoxybenzonitrile |
| I-99 | m/z: 469.09 (M + H)+ Rt (min): 1.05 | 1H NMR (300 MHz, METHANOL-d4): δ ppm 7.72 (s, 1 H), 7.25 (d, J = 8.50 Hz, 1 H), 7.22-7.19 (m, 1 H), 7.14-7.11 (m, 1 H), 6.31-6.28 (m, 1 H), 6.27-6.21 (m, 1 H), 4.38-4.33 (m, 2 H), 4.28 (dd, J = 5.00, 5.00 Hz, 2 H), 3.76-3.85 (m, 7 H), 2.92 (dd, J = 5.00, 5.00 Hz, 2 H), 2.68-2.55 (m, 4 H). | 4-[({6-chloro-8-[2-(morpholin-4-yl)ethoxy]-2-oxo-1,2-dihydroquinolin-3-yl}methyl)amino]-2-methoxybenzonitrile |
| I-100 | m/z: 453.07 (M + H)+ Rt (min): 1.03 | | 4-[({6-chloro-2-oxo-8-[2-(pyrrolidin-1-yl)ethoxy]-1,2-dihydroquinolin-3-yl}methyl)amino]-2-methoxybenzonitrile |

[a]LCMS data are determined by Method 4.

Example 28—IDH1-R132H and IDH1-R132C Enzymatic Assay

Assays were performed in a 384-well black plate. An aliquot of 250 nL of compound was incubated with 10 μL of 30 nM IDH1-R132H or 10 nM IDH1-R132C recombinant protein in assay buffer (50 mM Tris pH=7.5, 150 mM NaCl, 5 mM $MgCl_2$, 0.1% (w/v) Bovine Serum Albumin, and 0.01% Triton X-100) in each well at 25° C. for 15 minutes. After the plate was centrifuged briefly, an aliquot of 10 μL of 2 mM α-ketoglutarate and 20 μM NADPH solution prepared in assay buffer was then added to each well and the reaction was maintained at 25° C. for 45 minutes. An aliquot of 10 μL of diaphorase solution (0.15 U/mL diaphorase and 30 μM Resazurin in assay buffer) was added to each well. The plate was maintained at 25° C. for 15 minutes and then read on a plate reader with excitation and emission wavelengths at 535 nm and 590 nm, respectively. The $IC_{50}$ of a given compound was calculated by fitting the dose response curve of inhibition of NADPH consumption at a given concentration with the four parameter logistic equation.

Example 29—Cellular 2-HG Assay Using HCT116 Mutant IDH1 Cells

HCT116 isogenic IDH1-R132H and IDH1-R132C mutant cells were cultured in growth media (McCoy's 5A, 10% fetal bovine serum, 1× antibiotic-antimycotic solution and 0.3 mg/mL G418) in 5% $CO_2$ in an incubator at 37° C. To prepare the assay, cells were trypsinized and resuspended in assay media (McCoy's 5A with no L-glutamine, 10% fetal bovine serum, 1× antibiotic-antimycotic solution and 0.3 mg/mL G418). An aliquot of 10,000 cells/100 μL was transferred to each well of a clear 96-well tissue culture plate. The cells were incubated in 5% $CO_2$ at 37° C. in an incubator overnight to allow for proper cell attachment. An aliquot of 50 μL of compound containing assay media were then added to each well and the assay plate was kept in 5% $CO_2$ at 37° C. in an incubator for 24 hours. The media was then removed from each well and 150 μL of a methanol/water mixture (80/20 v/v) was added to each well. The plates were kept at −80° C. freezer overnight to allow for complete cell lysis. An aliquot of 125 μL of extracted supernatant was analyzed by RapidFire high-throughout-mass spectrometry (Agilent) to determine the cellular 2-HG level. The $IC_{50}$ of a given compound was calculated by fitting the dose response curve of cellular 2-HG inhibition at a given concentration with the four parameter logistic equation.

For HCT116 IDH1 R132H and HCT116 IDH1 R132C, "++++" indicates an inhibition at a concentration <0.01 μM; "+++" indicates inhibition at a concentration between 0.01 μM and 0.1 μM of the disclosed compound; "++" indicates inhibition at a concentration from 0.1 μM to 1 μM of the disclosed compound; and "+" indicates inhibition at a concentration >1 μM.

TABLE 11

Results of the illustrative compounds of Formula I in IDH1-R132H, IDH1-R132C, IDH1-MS-HTC116-R132H, and IDH1-MS-HTC116-R132C assays.

| Compounds | Enzyme IDH1 R132H $IC_{50}$ Range | Enzyme IDH1 R132C $IC_{50}$ Range | HCT116 IDH1 R132H $IC_{50}$ Range | HCT116 IDH1 R132C $IC_{50}$ Range |
|---|---|---|---|---|
| I-1 | +++ | +++ | | |
| I-2 | +++ | ++ | ++++ | ++ |
| I-3 | + | | | |
| I-4 | + | | | |
| I-5 | +++ | ++ | | |
| I-6 | + | | | |
| I-7 | ++ | + | ++ | + |
| I-8 | ++ | + | | |
| I-9 | ++ | + | | |
| I-10 | ++ | + | | |
| I-11 | ++ | | | |
| I-12 | + | | | |
| I-13 | ++ | | | |
| I-14 | + | | | |
| I-15 | + | | | |
| I-16 | ++ | + | | |
| I-17 | + | | | |
| I-18 | + | | | |
| I-19 | + | | | |
| I-20 | ++ | | | |
| I-21 | ++ | ++ | | |
| I-22 | ++ | + | | |
| I-23 | +++ | | | |
| I-24 | +++ | + | | |
| I-25 | +++ | + | | |
| I-26 | +++ | + | | |
| I-27 | + | + | | |
| I-28 | ++ | | | |
| I-29 | ++ | | | |
| I-30 | ++ | + | | |
| I-31 | + | | | |
| I-32 | ++ | + | | |
| I-33 | ++ | + | | |
| I-34 | ++ | | | |
| I-35 | ++ | | | |
| I-36 | ++ | + | | |
| I-37 | ++ | | | |
| I-38 | ++ | + | | |
| I-39 | + | | | |
| I-40 | + | | | |
| I-41 | + | | | |
| I-42 | + | | | |
| I-43 | + | | | |
| I-44 | + | | | |
| I-45 | + | | | |
| I-46 | + | | | |
| I-47 | ++ | + | | |
| I-48 | + | | | |
| I-49 | + | | | |
| I-50 | ++ | | | |
| I-51 | + | | | |
| I-52 | ++ | | | |
| I-53 | + | | | |
| I-54 | ++ | | | |
| I-55 | ++ | | | |
| I-56 | ++ | | | |
| I-57 | +++ | | | |
| I-58 | +++ | ++ | | |
| I-59 | ++ | + | | |
| I-60 | +++ | ++ | | |
| I-61 | +++ | + | | |
| I-62 | +++ | + | | |
| I-63 | +++ | + | | |
| I-64 | +++ | ++ | | |
| I-65 | +++ | + | | |
| I-66 | +++ | + | | |
| I-67 | +++ | + | | |
| I-68 | +++ | ++ | | |
| I-69 | +++ | + | | |
| I-70 | +++ | ++ | | |
| I-71 | +++ | + | | |
| I-72 | +++ | + | | |
| I-73 | +++ | | | |
| I-74 | ++ | + | | |

TABLE 11-continued

Results of the illustrative compounds of Formula I in IDH1-R132H, IDH1-R132C, IDH1-MS-HTC116-R132H, and IDH1-MS-HTC116-R132C assays.

| Compounds | Enzyme IDH1 R132H IC$_{50}$ Range | Enzyme IDH1 R132C IC$_{50}$ Range | HCT116 IDH1 R132H IC$_{50}$ Range | HCT116 IDH1 R132C IC$_{50}$ Range |
|---|---|---|---|---|
| I-75 | ++ | + | | |
| I-76 | +++ | + | | |
| I-77 | +++ | ++ | | |
| I-78 | +++ | ++ | | |
| I-79 | +++ | ++ | | |
| I-80 | +++ | + | | |
| I-81 | +++ | + | | |
| I-82 | ++ | + | | |
| I-83 | +++ | + | | |
| I-84 | ++ | + | | |
| I-85 | ++ | + | | |
| I-86 | +++ | + | | |
| I-87 | +++ | + | | |
| I-88 | +++ | + | | |
| I-89 | +++ | + | | |
| I-90 | +++ | ++ | | |
| I-91 | ++ | + | | |
| I-92 | ++ | + | | |
| I-93 | ++ | | | |
| I-94 | +++ | + | | |
| I-95 | ++ | + | | |
| I-96 | ++ | | | |
| I-97 | ++ | + | | |
| I-98 | +++ | + | | |
| I-99 | ++ | + | | |
| I-100 | ++ | + | | |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of formula I:

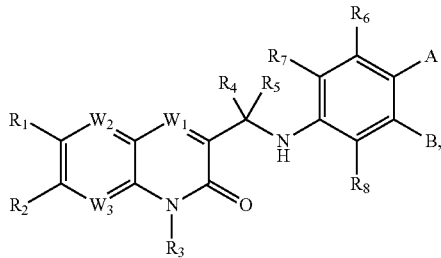

or pharmaceutically acceptable salt thereof, wherein:

$W_1$ and $W_2$ are CH;

$W_3$ is $CR_2$;

A is CN;

B is H or $C_1$-$C_6$ alkoxy;

$R_1$ is halogen;

$R_2$ is H;

$R_3$ is H;

$R_4$ and $R_5$ are independently H or $C_1$-$C_3$ alkyl;

$R_6$, $R_7$, and $R_8$ are independently H or $C_1$-$C_6$ alkoxy.

2. The compound of claim 1, wherein B is methoxy.

3. The compound of claim 2, wherein $R_4$ is H and $R_5$ is methyl.

4. The compound of claim 3, wherein $R_4$ is H and $R_5$ is (S)-methyl.

5. The compound of claim 4, wherein $R_1$ is chloro.

6. The compound of claim 1 having the formula Ia:

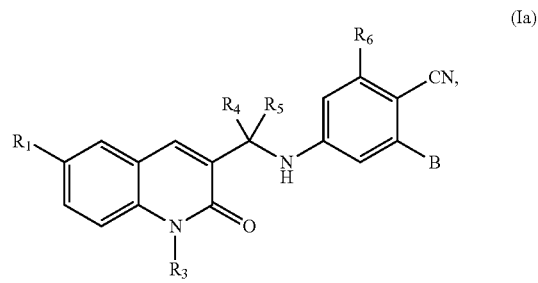

or pharmaceutically acceptable salt thereof.

7. A pharmaceutical composition comprising (S)-4-((1-(6-chloro-2-oxo-1,2-dihydroquinolin-3-yl)ethyl)amino)-2-methoxybenzonitrile, or a pharmaceutically acceptable salt thereof and pharmaceutically acceptable carrier.

8. A mixture comprising (S)-3-(1-aminoethyl)-6-chloro-quinolin-2(1H)-one hydrochloride and 4-fluoro-2-methoxy-benzonitrile.

9. The mixture of claim 8, further comprising (S)-4-((1-(6-chloro-2-oxo-1,2-dihydroquinolin-3-yl)ethyl)amino)-2-methoxybenzonitrile, or a pharmaceutically acceptable salt thereof and pharmaceutically acceptable carrier.

* * * * *